(12) United States Patent
Medlin et al.

(10) Patent No.: US 10,294,533 B2
(45) Date of Patent: May 21, 2019

(54) MICROARRAY SLIDE FOR DETECTING TOXIC ALGAE, BARCODES OF DNA, HYBRIDISATION SOLUTION AND METHOD OF DETECTING TOXIC ALGAE

(71) Applicant: MICROBIA ENVIRONNEMENT, Saint Jean de Lasseille (FR)

(72) Inventors: Linda Medlin, Plymouth (GB); Marina Montresor, Naples (IT); Edna Graneli, Kalmar (SE); Beatriz Reguera, Vigo (ES); Robin Raine, Galway (IE); Bente Edvardsen, Oslo (NO); Jane Lewis, London (GB)

(73) Assignee: MICROBIA ENVIRONNEMENT, Saint Jean de Lasseille (FR)

( * ) Notice: Subject to any disclaimer, the term of this patent is extended or adjusted under 35 U.S.C. 154(b) by 275 days.

(21) Appl. No.: 14/904,393

(22) PCT Filed: Jul. 19, 2013

(86) PCT No.: PCT/GB2013/051938
§ 371 (c)(1),
(2) Date: Jan. 11, 2016

(87) PCT Pub. No.: WO2015/008011
PCT Pub. Date: Jan. 22, 2015

(65) Prior Publication Data
US 2016/0281178 A1   Sep. 29, 2016

(51) Int. Cl.
*C12Q 1/6895* (2018.01)
*C12Q 1/6827* (2018.01)
*C12Q 1/6837* (2018.01)

(52) U.S. Cl.
CPC ......... *C12Q 1/6895* (2013.01); *C12Q 1/6837* (2013.01); *C12Q 2600/158* (2013.01); *C12Q 2600/166* (2013.01)

(58) Field of Classification Search
CPC .......................... C12Q 1/6837; C12Q 1/6895
See application file for complete search history.

(56) References Cited

FOREIGN PATENT DOCUMENTS

WO      03/053855 A2    7/2003

OTHER PUBLICATIONS

Kegel, J. et al. Environ Sci Pollut Res 20:6690 (2013; online Nov. 22, 2012).*
Shang, S. et al. Pediatric Research 58(1):143 (2005).*
International Search Report from International Application No. PCT/GB2013/051938, dated Dec. 2, 2013.
Anderson et al., "Estimated Annual Economic Impacts from Harmful Algal Bloom (HABs) in the United States", Woods Hole Oceanographic Institution—Technical Report, Sep. 2000, pp. 1-97.
Anderson et al., "Fibre optic microarrays for the detection and enumeration of harmful algal bloom species", African Journal of Marine Science (2006), v 28, n 2, pp. 231-235.
Browne et al., "Status of Irish Aquaculture 2007", MERC Consultants—Report (2008), pp. 1-144.
Dittami et al., "GPR-Analyzer: a simple tool for quantitative analysis of hierarchical multispecies microarrays", Environmental Science & Pollution Research (2013), vol. 20, pp. 6808-6815.
Dittami et al., "Microarray testing for the presence of toxic algae monitoring programme in Galicia (NW Spain)", Environmental Science & Pollution Research (2013), vol. 20, pp. 6778-6793.
Ebenezer et al., "Molecular Detection, Quantification, and Diversity Evaluation of Microalgae", Marine Biotechnology (2012), vol. 14, pp. 129-142.
Edvardsen et al., "Molecular probes and microarrays for the detection of toxic algae in the genera *Dinophysis* and *Phalacroma* (Dinophyta)", Environmental Science & Pollution Research (2013), vol. 20, pp. 6733-6750.
Food and Agriculture Organization of the United Nations, "Marine Biotoxins", FAO Food and Nutrition Paper—Rome (2004), pp. 1-281.
Galluzzi et al., "Development of an oligonucleotide microarray for the detection and monitoring of marine dinoflagellates", Journal of Microbiological Methods (2011), vol. 84, pp. 234-242.
Gescher et al., "The ALEX CHIP—Development of a DNA chip for identification and monitoring of Alexandrium", Harmful Algae (2008), vol. 7, pp. 485-494.
Ki et al., "A low-density oligonucleotide array study for parallel detection of harmful algal species using hybridization of consensus PCR products of LSU rDNA D2 domain", Biosensors and Bioelectronics (2006), vol. 21, pp. 1812-1821.
Lewis et al., "MIDTAL (Microarrays for the Detection of Toxic Algae)", Phytotaxa (2013), v 127, n 1, pp. 201-210.
Ludwig et al., "ARB: a software environment for sequence data", Nucleic Acids Research (2004), v 32, n 4, pp. 1363-1371.
Medlin, Linda K., "Note: steps taken to optimise probe specificity and signal intensity prior to field validation of the MIDTAL (Microarray for the Detection of Toxic Algae)", Environmental Science & Pollution Research (2013), vol. 20, pp. 6686-6689.
Medlin et al., "Methods to Estimate the Diversity in the Marine Photosynthetic Protist Community with Illustrations from Case Studies: A Review", Diversity (2010), vol. 2, pp. 973-1014.
Metfies et al., "Feasibility of Transferring Fluorescent in Situ Hybridization Probes to an 18S rRNA Gene Phylochip and Mapping of Signal Intensities", Applied and Environmental Microbiology (2008), v 74, n 9, pp. 2814-2821.

(Continued)

*Primary Examiner* — Diana B Johannsen
(74) *Attorney, Agent, or Firm* — Greer, Burns & Crain, Ltd.

(57) ABSTRACT

An array system is provided including a microarray slide configured to detect simultaneously a plurality of organisms in a sample, wherein the microarray slide includes nucleic acid probes having fragments of 18S or 28S RNA sequence unique to each organism or taxonomical group thereof. The present microarray slide is useful for detecting different species of toxic algae.

4 Claims, 12 Drawing Sheets
Specification includes a Sequence Listing.

(56) References Cited

OTHER PUBLICATIONS

Metfies et al., Laboratory and Field Applications of Ribosomal RNA Probes to Aid the Detection and Monitoring of Harmful Algae (2006), vol. 189, pp. 311-325.

Touzet et al., PSP toxin analysis and discrimination of the naturally co-occurring Alexandrium tamarense and A. minutum (Dinophyceae) in Cork Harbour, Ireland (2008), vol. 51, pp. 285-299.

* cited by examiner

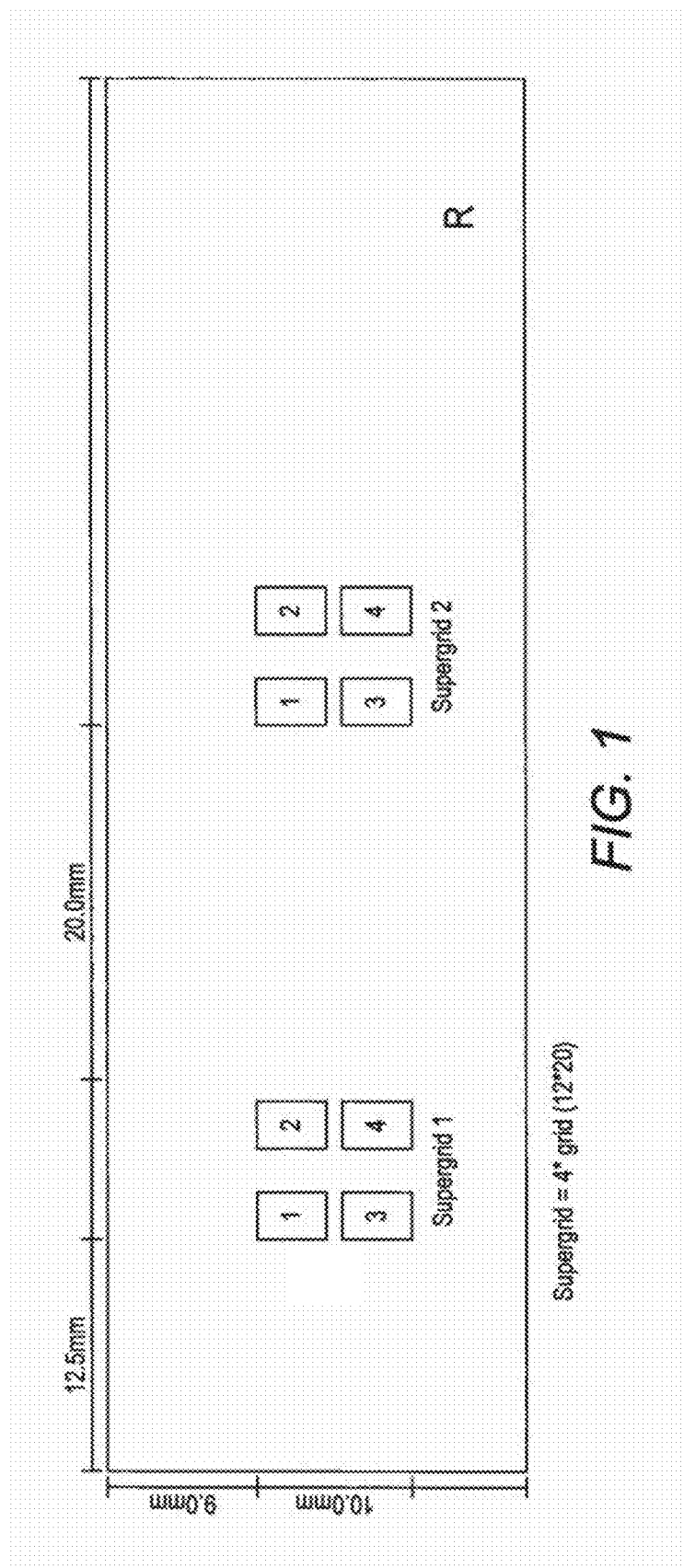

Grid 1

|   | 1 | 2 | 3 | 4 | 5 | 6 | 7 | 8 | 9 | 10 | 11 | 12 |
|---|---|---|---|---|---|---|---|---|---|----|----|----|
| A | M002 | M002 | M001 | M001 | M003 | M003 | M004 | M004 | M006 | M006 | M008 | M008 |
| B | M002 | M002 | M001 | M001 | M003 | M003 | M004 | M004 | M006 | M006 | M008 | M008 |
| C | M010 | M010 | M012 | M012 | M014 | M014 | M016 | M016 | M018 | M018 | M020 | M020 |
| D | M010 | M010 | M012 | M012 | M014 | M014 | M016 | M016 | M018 | M018 | M020 | M020 |
| E | M040 | M040 | M042 | M042 | 3XSSC | 3XSSC | M046 | M046 | M048 | M048 | M050 | M050 |
| F | M040 | M040 | M042 | M042 | 3XSSC | 3XSSC | M046 | M046 | M048 | M048 | M050 | M050 |
| G | M052 | M052 | M054 | M054 | M056 | M056 | M058 | M058 | M060 | M060 | M062 | M062 |
| H | M052 | M052 | M054 | M054 | M056 | M056 | M058 | M058 | M060 | M060 | M062 | M062 |
| I | M068 | M068 | M090 | M090 | M092 | M092 | M094 | M094 | M096 | M096 | M098 | M098 |
| J | M068 | M068 | M090 | M090 | M092 | M092 | M094 | M094 | M096 | M096 | M098 | M098 |
| K | M100 | M100 | M102 | M102 | M104 | M104 | M106 | M106 | M108 | M108 | M110 | M110 |
| L | M100 | M100 | M102 | M102 | M104 | M104 | M106 | M106 | M108 | M108 | M110 | M110 |
| M | M027 | M027 | M029 | M029 | M031 | M031 | M033 | M033 | M035 | M035 | M037 | M037 |
| N | M027 | M027 | M029 | M029 | M031 | M031 | M033 | M033 | M035 | M035 | M037 | M037 |
| O | M039 | M039 | M041 | M041 | 3XSSC | 3XSSC | M045 | M045 | M047 | M047 | M049 | M049 |
| P | M039 | M039 | M041 | M041 | 3XSSC | 3XSSC | M045 | M045 | M047 | M047 | M049 | M049 |
| Q | M075 | M075 | M077 | M077 | M079 | M079 | M081 | M081 | M083 | M083 | M085 | M085 |
| R | M075 | M075 | M077 | M077 | M079 | M079 | M081 | M081 | M083 | M083 | M085 | M085 |
| S | 3XSSC | 3XSSC | M089 | M089 | M091 | M091 | M093 | M093 | M001 | M001 | M002 | M002 |
| T | 3XSSC | 3XSSC | M089 | M089 | M091 | M091 | M093 | M093 | M001 | M001 | M002 | M002 |

*FIG. 1* Cont'd

Grid 2

|   | 1 | 2 | 3 | 4 | 5 | 6 | 7 | 8 | 9 | 10 | 11 | 12 |
|---|---|---|---|---|---|---|---|---|---|----|----|----|
| A | M002 | M002 | M001 | M001 | M003 | M003 | M005 | M005 | M007 | M007 | M009 | M009 |
| B | M002 | M002 | M001 | M001 | M003 | M003 | M005 | M005 | M007 | M007 | M009 | M009 |
| C | M011 | M011 | M013 | M013 | M015 | M015 | M017 | M017 | M019 | M019 | M021 | M021 |
| D | M011 | M011 | M013 | M013 | M015 | M015 | M017 | M017 | M019 | M019 | M021 | M021 |
| E | M041 | M041 | 3XSSC | 3XSSC | M045 | M045 | M047 | M047 | M049 | M049 | M051 | M051 |
| F | M041 | M041 | 3XSSC | 3XSSC | M045 | M045 | M047 | M047 | M049 | M049 | M051 | M051 |
| G | M053 | M053 | M055 | M055 | M057 | M057 | M059 | M059 | M061 | M061 | M063 | M063 |
| H | M053 | M053 | M055 | M055 | M057 | M057 | M059 | M059 | M061 | M061 | M063 | M063 |
| I | M089 | M089 | M091 | M091 | M093 | M093 | M095 | M095 | M097 | M097 | M099 | M099 |
| J | M089 | M089 | M091 | M091 | M093 | M093 | M095 | M095 | M097 | M097 | M099 | M099 |
| K | M101 | M101 | M103 | M103 | M105 | M105 | M107 | M107 | M109 | M109 | M111 | M111 |
| L | M101 | M101 | M103 | M103 | M105 | M105 | M107 | M107 | M109 | M109 | M111 | M111 |
| M | M028 | M028 | M030 | M030 | M032 | M032 | M034 | M034 | M036 | M036 | M038 | M038 |
| N | M028 | M028 | M030 | M030 | M032 | M032 | M034 | M034 | M036 | M036 | M038 | M038 |
| O | M040 | M040 | M042 | M042 | 3XSSC | 3XSSC | M046 | M046 | M048 | M048 | M050 | M050 |
| P | M040 | M040 | M042 | M042 | 3XSSC | 3XSSC | M046 | M046 | M048 | M048 | M050 | M050 |
| Q | M076 | M076 | M078 | M078 | M080 | M080 | M082 | M082 | M084 | M084 | M086 | M086 |
| R | M076 | M076 | M078 | M078 | M080 | M080 | M082 | M082 | M084 | M084 | M086 | M086 |
| S | M088 | M088 | M090 | M090 | M092 | M092 | M094 | M094 | M001 | M001 | M002 | M002 |
| T | M088 | M088 | M090 | M090 | M092 | M092 | M094 | M094 | M001 | M001 | M002 | M002 |

*FIG. 1* Cont'd

Grid 3

|   | 1 | 2 | 3 | 4 | 5 | 6 | 7 | 8 | 9 | 10 | 11 | 12 |
|---|---|---|---|---|---|---|---|---|---|----|----|----|
| A | M002 | M002 | M001 | M001 | M003 | M003 | M022 | M022 | M024 | M024 | M026 | M026 |
| B | M002 | M002 | M001 | M001 | M003 | M003 | M022 | M022 | M024 | M024 | M026 | M026 |
| C | M028 | M028 | M030 | M030 | M032 | M032 | M034 | M034 | M036 | M036 | M038 | M038 |
| D | M028 | M028 | M030 | M030 | M032 | M032 | M034 | M034 | M036 | M036 | M038 | M038 |
| E | M064 | M064 | M066 | M066 | M068 | M068 | M070 | M070 | M072 | M072 | M074 | M074 |
| F | M064 | M064 | M066 | M066 | M068 | M068 | M070 | M070 | M072 | M072 | M074 | M074 |
| G | M076 | M076 | M078 | M078 | M080 | M080 | M082 | M082 | M084 | M084 | M086 | M086 |
| H | M076 | M076 | M078 | M078 | M080 | M080 | M082 | M082 | M084 | M084 | M086 | M086 |
| I | M112 | M112 | M005 | M005 | M007 | M007 | M009 | M009 | M011 | M011 | M013 | M013 |
| J | M112 | M112 | M005 | M005 | M007 | M007 | M009 | M009 | M011 | M011 | M013 | M013 |
| K | M015 | M015 | M017 | M017 | M019 | M019 | M021 | M021 | M023 | M023 | M025 | M025 |
| L | M015 | M015 | M017 | M017 | M019 | M019 | M021 | M021 | M023 | M023 | M025 | M025 |
| M | M051 | M051 | M053 | M053 | M055 | M055 | M057 | M057 | M059 | M059 | M061 | M061 |
| N | M051 | M051 | M053 | M053 | M055 | M055 | M057 | M057 | M059 | M059 | M061 | M061 |
| O | M063 | M063 | M065 | M065 | M067 | M067 | M069 | M069 | M071 | M071 | M073 | M073 |
| P | M063 | M063 | M065 | M065 | M067 | M067 | M069 | M069 | M071 | M071 | M073 | M073 |
| Q | M095 | M095 | M097 | M097 | M099 | M099 | M101 | M101 | M103 | M103 | M105 | M105 |
| R | M095 | M095 | M097 | M097 | M099 | M099 | M101 | M101 | M103 | M103 | M105 | M105 |
| S | M107 | M107 | M109 | M109 | M111 | M111 | 3XSSC | 3XSSC | M001 | M001 | M002 | M002 |
| T | M107 | M107 | M109 | M109 | M111 | M111 | 3XSSC | 3XSSC | M001 | M001 | M002 | M002 |

*FIG. 1* Cont'd

Grid 4

|   | 1 | 2 | 3 | 4 | 5 | 6 | 7 | 8 | 9 | 10 | 11 | 12 |
|---|---|---|---|---|---|---|---|---|---|----|----|----|
| A | M002 | M002 | M001 | M001 | M003 | M003 | M023 | M023 | M025 | M025 | M027 | M027 |
| B | M002 | M002 | M001 | M001 | M003 | M003 | M023 | M023 | M025 | M025 | M027 | M027 |
| C | M029 | M029 | M031 | M031 | M033 | M033 | M035 | M035 | M037 | M037 | M039 | M039 |
| D | M029 | M029 | M031 | M031 | M033 | M033 | M035 | M035 | M037 | M037 | M039 | M039 |
| E | M065 | M065 | M067 | M067 | M069 | M069 | M071 | M071 | M073 | M073 | M075 | M075 |
| F | M065 | M065 | M067 | M067 | M069 | M069 | M071 | M071 | M073 | M073 | M075 | M075 |
| G | M077 | M077 | M079 | M079 | M081 | M081 | M083 | M083 | M085 | M085 | 3XSSC | 3XSSC |
| H | M077 | M077 | M079 | M079 | M081 | M081 | M083 | M083 | M085 | M085 | 3XSSC | 3XSSC |
| I | M004 | M004 | M006 | M006 | M008 | M008 | M010 | M010 | M012 | M012 | M014 | M014 |
| J | M004 | M004 | M006 | M006 | M008 | M008 | M010 | M010 | M012 | M012 | M014 | M014 |
| K | M016 | M016 | M018 | M018 | M020 | M020 | M022 | M022 | M024 | M024 | M026 | M026 |
| L | M016 | M016 | M018 | M018 | M020 | M020 | M022 | M022 | M024 | M024 | M026 | M026 |
| M | M052 | M052 | M054 | M054 | M056 | M056 | M058 | M058 | M060 | M060 | M062 | M062 |
| N | M052 | M052 | M054 | M054 | M056 | M056 | M058 | M058 | M060 | M060 | M062 | M062 |
| O | M064 | M064 | M066 | M066 | M068 | M068 | M070 | M070 | M072 | M072 | M074 | M074 |
| P | M064 | M064 | M066 | M066 | M068 | M068 | M070 | M070 | M072 | M072 | M074 | M074 |
| Q | M096 | M096 | M098 | M098 | M100 | M100 | M102 | M102 | M104 | M104 | M106 | M106 |
| R | M096 | M096 | M098 | M098 | M100 | M100 | M102 | M102 | M104 | M104 | M106 | M106 |
| S | M108 | M108 | M110 | M110 | M112 | M112 | 3XSSC | 3XSSC | M001 | M001 | M002 | M002 |
| T | M108 | M108 | M110 | M110 | M112 | M112 | 3XSSC | 3XSSC | M001 | M001 | M002 | M002 |

*FIG. 1* Cont'd

| | Mostra_60_1_c_2012_05_16_3ªxene.gpr - MIDTAL GPR analyser v1.27 |
|---|---|

File  Tools  About

| Probe | Species ▾ | S/N | Norm. |
|---|---|---|---|
| PpungcalS01_25_dT | Pseudo-nitzchia spp. | 2.9 | 0.9053 |
| Pdel4D03_25_dT | Pseudo-nitzchia spp. | 25.03 | 24.9726 |
| PgalaD04_25_dT | Pseudo-nitzchia spp. | 1.53 | 0.4064 |
| PmultcalD01_25_dT | Pseudo-nitzchia spp. | 24.98 | 19.2793 |
| PmulaD03_25_dT | Pseudo-nitzchia spp. | 21.4 | 8.2144 |
| PfraucalD02_25_dT | Pseudo-nitzchia spp. | 17.16 | 7.5439 |
| PcaciD02_25_dT | Pseudo-nitzchia spp. | 2.07 | 0.4526 |
| PmanD01_25_dT | Pseudo-nitzchia spp. | 1.43 | 0.1557 |
| PSN_FragS01 | Pseudo-nitzchia spp. | 42.64 | 16.4109 |
| Pman2D05_25_dT | Pseudo-nitzchia spp. | 2.37 | 0.4588 |
| Pdel4D02_25_dT | Pseudo-nitzchia spp. | 4.66 | 1.7279 |
| PlimaD01_25_dT | Pseudo-nitzchia spp. | 1.29 | 0.0848 |
| PdeliD02_25_dT | Pseudo-nitzchia spp. | 2.23 | 0.2869 |
| PmulausD01_25_dT | Pseudo-nitzchia spp. | 44.47 | 17.3773 |
| PcaserausD03_25_dT | Pseudo-nitzchia seriata/australis (with hierarchy) | 42.17 | 13.7046 |
| PpdaD02_25_dT | Pseudo-nitzchia pseudodelicatissima (with hierarchy) | 3.63 | 1.4206 |
| Pdel3B_25_dT | Pseudo-nitzchia delicatissima Clade3 (with hierarchy) | 1.15 | 0.0493 |
| Pcal1D01_25_dT | Pseudo-nitzchia calliantha (with hierarchy) | 2.44 | 0.5302 |
| PcaciD01_25_dT | Pseudo-nitzchia calliantha (with hierarchy) | 1.64 | 0.2107 |
| PgalaD02_25_dT | Pseudo-nitzchia alaxiae (with hierarchy) | 1.19 | 0.0688 |
| CompPdel3_25_dT | Pseudo-nitzchia | 5.97 | 2.4677 |
| PverD01_25_dT | Pseudochattonella verruclosa | 1.52 | 0.1901 |
| PschGS04_25_dT | Pseudochattonella spp. | 10.47 | 3.5379 |
| PschGS01_25_dT | Pseudochattonella spp. | 1.79 | 0.2816 |
| PschGS05_25_dT | Pseudochattonella spp. | 1.17 | 0.0478 |
| PrymS01_25_dT | Prymnesium spp. | 3.34 | 0.4866 |
| PrymS02_25_dT | Prymnesium spp. | 20.17 | 7.5218 |
| PrymS03_25_dT | Prymnesium spp. | 1.51 | 0.1536 |
| CpolyS01_25_dT | Prymnesium polylepis | 1.01 | -0.0139 |

Spots:

| Probe | Block | Column | Row | Fmean |
|---|---|---|---|---|
| Pcal1D01_25_dT | 3 | 5 | 7 | 201 |
| Pcal1D01_25_dT | 3 | 6 | 7 | 198 |
| Pcal1D01_25_dT | 3 | 5 | 8 | 219 |
| Pcal1D01_25_dT | 3 | 6 | 8 | 188 |
| Pcal1D01_25_dT | 8 | 1 | 9 | 238 |
| Pcal1D01_25_dT | 8 | 2 | 9 | 242 |
| Pcal1D01_25_dT | 8 | 1 | 10 | 250 |
| Pcal1D01_25_dT | 8 | 2 | 10 | 263 |

MICROARRAYS FOR THE DETECTION OF TOXIC ALGAE

*FIG. 6*

| Cells/L | Hierarchy |
|---|---|
| | |
| | |
| | |
| 5476280 | |
| 15087858 | |
| | |
| | |
| 4411648 | |
| | |
| | |
| 7270833 | |
| | 100% (passed: PsnGS02_25_dT) |
| | 50% (failed: PpdeD01_25_dT; passed: PsnGS02_25_dT) |
| 1325569 | 100% (passed: PcaserausD03_25_dT, PmultcaiD03_25_dT, PpungcalS... |
| <852936 | |
| | |
| <212585 | |
| | 0% (failed: PschGS05_25_dT, PschGS01_25_dT) |
| | |
| | |
| | 0% (failed: PrymS03_25_dT) |
| | |
| | |
| <311299 | |

| Bmean | S/N | Total | Active |
|---|---|---|---|
| 77 | 2.61 | 1402406 | ☑ |
| 77 | 2.57 | 1368477 | ☑ |
| 78 | 2.81 | 1594671 | ☑ |
| 83 | 2.27 | 1187521 | ☑ |
| 76 | 3.13 | 1832175 | ☑ |
| 126 | 1.92 | 1311928 | ☑ |
| 103 | 2.43 | 1662529 | ☑ |
| 147 | 1.79 | 1311928 | ☑ |

*FIG. 6* Cont'd

SEQUENCE LISTING

```
<160> NUMBER OF SEQ ID NOS: 252

<210> SEQ ID NO 1
<211> LENGTH: 40
<212> TYPE: DNA
<213> ORGANISM: Artificial sequence
<220> FEATURE:
<223> OTHER INFORMATION: Eukaryotes TATA box protein - positive control

<400> SEQUENCE: 1
tttttttttt ttttttttta attatggccg atgaggaacg                          40

<210> SEQ ID NO 2
<211> LENGTH: 37
<212> TYPE: DNA
<213> ORGANISM: Artificial sequence
<220> FEATURE:
<223> OTHER INFORMATION: Negative control

<400> SEQUENCE: 2
tttttttttt tttttttttt cccccgggta tggccgc                             37

<210> SEQ ID NO 3
<211> LENGTH: 40
<212> TYPE: DNA
<213> ORGANISM: Artificial sequence
<220> FEATURE:
<223> OTHER INFORMATION: Negative control

<400> SEQUENCE: 3
tttttttttt tttttaggaa ggaaggaagg aaggaaggaa                          40

<210> SEQ ID NO 4
<211> LENGTH: 40
<212> TYPE: DNA
<213> ORGANISM: Artificial sequence
<220> FEATURE:
<223> OTHER INFORMATION: Negative control

<400> SEQUENCE: 4
tttttttttt tttttagaga gagagagaga gagagagaga                          40

<210> SEQ ID NO 5
<211> LENGTH: 40
<212> TYPE: DNA
<213> ORGANISM: Artificial sequence
<220> FEATURE:
<223> OTHER INFORMATION: Poly-Thymine sequencce labelled with
      Cyanine-5 - spotting control
<220> FEATURE:
```

```
<221> NAME/KEY: misc_feature
<222> LOCATION: (30)..(30)
<223> OTHER INFORMATION: Other: Cyanine-5 (Cy5) labelled thymine residue

<400> SEQUENCE: 5
tttttttttt tttttttttt ttttttttttn tttttttttt                              40

<210> SEQ ID NO 6
<211> LENGTH: 32
<212> TYPE: DNA
<213> ORGANISM: Artificial sequence
<220> FEATURE:
<223> OTHER INFORMATION: Poly-Adenine sequence - blocking probe

<400> SEQUENCE: 6
aaaaaaaaaa aaaaaaaaaa aaaaaaaaaa aa                                       32

<210> SEQ ID NO 7
<211> LENGTH: 40
<212> TYPE: DNA
<213> ORGANISM: Artificial sequence
<220> FEATURE:
<223> OTHER INFORMATION: Dunaliella

<400> SEQUENCE: 7
tttttttttt ttttttaccaa aggctgaccg ctacaaccca                              40

<210> SEQ ID NO 8
<211> LENGTH: 40
<212> TYPE: DNA
<213> ORGANISM: Artificial sequence
<220> FEATURE:
<223> OTHER INFORMATION: Dunaliella

<400> SEQUENCE: 8
tttttttttt tttttttgata ccgatccaaa cacttcacca                              40

<210> SEQ ID NO 9
<211> LENGTH: 40
<212> TYPE: DNA
<213> ORGANISM: Artificial sequence
<220> FEATURE:
<223> OTHER INFORMATION: Eukaryotes

<400> SEQUENCE: 9
tttttttttt tttttttgact actggcagga tcaaccaggt                              40

<210> SEQ ID NO 10
<211> LENGTH: 40
<212> TYPE: DNA
<213> ORGANISM: Artificial sequence
<220> FEATURE:
<223> OTHER INFORMATION: Eukaryotes

<400> SEQUENCE: 10
tttttttttt tttttaacat ctaagggcat cacagacctg                               40

<210> SEQ ID NO 11
<211> LENGTH: 40
<212> TYPE: DNA
<213> ORGANISM: Artificial sequence
<220> FEATURE:
<223> OTHER INFORMATION: Prymnesiophyta

<400> SEQUENCE: 11
tttttttttt tttttaaaca tccctggcaa atgctttcgc                               40
```

```
<210> SEQ ID NO 12
<211> LENGTH: 40
<212> TYPE: DNA
<213> ORGANISM: Artificial sequence
<220> FEATURE:
<223> OTHER INFORMATION: Prymnesiophyceae

<400> SEQUENCE: 12
tttttttttt tttttgtgt caggattcgg gcaatttacg                              40

<210> SEQ ID NO 13
<211> LENGTH: 40
<212> TYPE: DNA
<213> ORGANISM: Artificial sequence
<220> FEATURE:
<223> OTHER INFORMATION: Dinophyceae (incl. Apicomplexa)

<400> SEQUENCE: 13
tttttttttt tttttctgtt attgcctcaa acttccttgc                              40

<210> SEQ ID NO 14
<211> LENGTH: 40
<212> TYPE: DNA
<213> ORGANISM: Artificial sequence
<220> FEATURE:
<223> OTHER INFORMATION: Dinophyceae (incl. Apicomplexa)

<400> SEQUENCE: 14
tttttttttt tttttgtcgg aagctgatag gtcagaaact                              40

<210> SEQ ID NO 15
<211> LENGTH: 42
<212> TYPE: DNA
<213> ORGANISM: Artificial sequence
<220> FEATURE:
<223> OTHER INFORMATION: Raphidophceae class

<400> SEQUENCE: 15
tttttttttt tttttcgatt cgcacagtta ctatgattca cc                           42

<210> SEQ ID NO 16
<211> LENGTH: 40
<212> TYPE: DNA
<213> ORGANISM: Artificial sequence
<220> FEATURE:
<223> OTHER INFORMATION: Raphidophceae class

<400> SEQUENCE: 16
tttttttttt tttttgcaag aaccggattg tcaccgtcca                              40

<210> SEQ ID NO 17
<211> LENGTH: 38
<212> TYPE: DNA
<213> ORGANISM: Artificial sequence
<220> FEATURE:
<223> OTHER INFORMATION: Dinophysiaceae (Dinophysis + Phalacroma) not
      D. acuta

<400> SEQUENCE: 17
tttttttttt tttttaggc caataccgta ccgtcgga                                 38

<210> SEQ ID NO 18
<211> LENGTH: 40
<212> TYPE: DNA
<213> ORGANISM: Artificial sequence
```

```
<220> FEATURE:
<223> OTHER INFORMATION: Dinophysiaceae (Dinophysis + Phalacroma)

<400> SEQUENCE: 18
tttttttttt tttttcaata ccgtaccgtc ggaagctgat                              40

<210> SEQ ID NO 19
<211> LENGTH: 40
<212> TYPE: DNA
<213> ORGANISM: Artificial sequence
<220> FEATURE:
<223> OTHER INFORMATION: Prorocentrum planktonic clade

<400> SEQUENCE: 19
tttttttttt tttttttcaa ggcgtaagcc tgcttgaaac                              40

<210> SEQ ID NO 20
<211> LENGTH: 40
<212> TYPE: DNA
<213> ORGANISM: Artificial sequence
<220> FEATURE:
<223> OTHER INFORMATION: Prorocentrum benthic clade

<400> SEQUENCE: 20
tttttttttt tttttgatgc ccagatcaag ccagatgctc                              40

<210> SEQ ID NO 21
<211> LENGTH: 40
<212> TYPE: DNA
<213> ORGANISM: Artificial sequence
<220> FEATURE:
<223> OTHER INFORMATION: Prorocentrum benthic clade

<400> SEQUENCE: 21
tttttttttt tttttccaac tatccccatt gaccattacc                              40

<210> SEQ ID NO 22
<211> LENGTH: 36
<212> TYPE: DNA
<213> ORGANISM: Artificial sequence
<220> FEATURE:
<223> OTHER INFORMATION: Prymnesium

<400> SEQUENCE: 22
tttttttttt tttttggact tccgccgatc cctagt                                  36

<210> SEQ ID NO 23
<211> LENGTH: 40
<212> TYPE: DNA
<213> ORGANISM: Artificial sequence
<220> FEATURE:
<223> OTHER INFORMATION: all Dinophysis and Phalacroma

<400> SEQUENCE: 23
tttttttttt tttttgtagg ccaataccgt accgtcggaa                              40

<210> SEQ ID NO 24
<211> LENGTH: 40
<212> TYPE: DNA
<213> ORGANISM: Artificial sequence
<220> FEATURE:
<223> OTHER INFORMATION: Prymnesium B1 clade

<400> SEQUENCE: 24
tttttttttt tttttactca gcacgcaacc ggcaagccgg                              40
```

<210> SEQ ID NO 25
<211> LENGTH: 40
<212> TYPE: DNA
<213> ORGANISM: Artificial sequence
<220> FEATURE:
<223> OTHER INFORMATION: Chattonella antiqua/marina/ovata clade

<400> SEQUENCE: 25
tttttttttt tttttcccga gagttaactc ggcattggtt    40

<210> SEQ ID NO 26
<211> LENGTH: 40
<212> TYPE: DNA
<213> ORGANISM: Artificial sequence
<220> FEATURE:
<223> OTHER INFORMATION: Chattonella antiqua/marina/ovata clade

<400> SEQUENCE: 26
tttttttttt tttttaaaga tggggagaat cgcaacccgt    40

<210> SEQ ID NO 27
<211> LENGTH: 40
<212> TYPE: DNA
<213> ORGANISM: Artificial sequence
<220> FEATURE:
<223> OTHER INFORMATION: Chattonella antiqua/marina/ovata clade

<400> SEQUENCE: 27
tttttttttt tttttgggg agaatcgcaa cccgtaagcg    40

<210> SEQ ID NO 28
<211> LENGTH: 40
<212> TYPE: DNA
<213> ORGANISM: Artificial sequence
<220> FEATURE:
<223> OTHER INFORMATION: Gambierdiscus carrpenteri+caribaeus clade

<400> SEQUENCE: 28
tttttttttt tttttcctct ttcgtccaga attgggcaag    40

<210> SEQ ID NO 29
<211> LENGTH: 40
<212> TYPE: DNA
<213> ORGANISM: Artificial sequence
<220> FEATURE:
<223> OTHER INFORMATION: Gambierdiscus carrpenteri+caribaeus clade

<400> SEQUENCE: 29
tttttttttt tttttccag aattgggcaa gttgcgcgcc    40

<210> SEQ ID NO 30
<211> LENGTH: 40
<212> TYPE: DNA
<213> ORGANISM: Artificial sequence
<220> FEATURE:
<223> OTHER INFORMATION: Gambierdiscus carrpenteri+caribaeus clade

<400> SEQUENCE: 30
tttttttttt tttttggcag attgcccaac ctctccaggg    40

<210> SEQ ID NO 31
<211> LENGTH: 40
<212> TYPE: DNA
<213> ORGANISM: Artificial sequence
<220> FEATURE:
<223> OTHER INFORMATION: Gambierdiscus carolinianus +polynesiensis

<400> SEQUENCE: 31
tttttttttt tttttccag aattgggcaa gttgcgcgcc                    40

<210> SEQ ID NO 32
<211> LENGTH: 40
<212> TYPE: DNA
<213> ORGANISM: Artificial sequence
<220> FEATURE:
<223> OTHER INFORMATION: Gambierdiscus carolinianus +polynesiensis

<400> SEQUENCE: 32
tttttttttt tttttccctg tttcacctttt ccagctccag                   40

<210> SEQ ID NO 33
<211> LENGTH: 39
<212> TYPE: DNA
<213> ORGANISM: Artificial sequence
<220> FEATURE:
<223> OTHER INFORMATION: Gambierdiscus carolinianus+carpenteri

<400> SEQUENCE: 33
tttttttttt ttttcctctt tcgtccagaa ttgggcaag                     39

<210> SEQ ID NO 34
<211> LENGTH: 39
<212> TYPE: DNA
<213> ORGANISM: Artificial sequence
<220> FEATURE:
<223> OTHER INFORMATION: Gambierdiscus carolinianus+carpenteri

<400> SEQUENCE: 34
tttttttttt ttttctgtgc tgctccatga ctggatgct                     39

<210> SEQ ID NO 35
<211> LENGTH: 39
<212> TYPE: DNA
<213> ORGANISM: Artificial sequence
<220> FEATURE:
<223> OTHER INFORMATION: Gambierdiscus carolinianus+carpenteri

<400> SEQUENCE: 35
tttttttttt ttttccctgt tcacctttc cagctccag                      39

<210> SEQ ID NO 36
<211> LENGTH: 39
<212> TYPE: DNA
<213> ORGANISM: Artificial sequence
<220> FEATURE:
<223> OTHER INFORMATION: Gambierdiscus toxicua and pacificus

<400> SEQUENCE: 36
tttttttttt ttttggcgga ccaggcatcc ccagcagag                     39

<210> SEQ ID NO 37
<211> LENGTH: 39
<212> TYPE: DNA
<213> ORGANISM: Artificial sequence
<220> FEATURE:
<223> OTHER INFORMATION: Gambierdiscus toxicua and pacificus

<400> SEQUENCE: 37
tttttttttt ttttacctgt cacagccaca gcaggccac                     39

<210> SEQ ID NO 38

```
<211> LENGTH: 39
<212> TYPE: DNA
<213> ORGANISM: Artificial sequence
<220> FEATURE:
<223> OTHER INFORMATION: Gambierdiscus toxicua and pacificus

<400> SEQUENCE: 38
tttttttttt ttttgtcaat cccacttgtg ccaggacct                    39

<210> SEQ ID NO 39
<211> LENGTH: 39
<212> TYPE: DNA
<213> ORGANISM: Artificial sequence
<220> FEATURE:
<223> OTHER INFORMATION: Ostreopsis ovata Clade

<400> SEQUENCE: 39
tttttttttt ttttgcatgc agctttgata gcactgtgc                    39

<210> SEQ ID NO 40
<211> LENGTH: 39
<212> TYPE: DNA
<213> ORGANISM: Artificial sequence
<220> FEATURE:
<223> OTHER INFORMATION: Ostreopsis ovata Clade

<400> SEQUENCE: 40
tttttttttt ttttggacaa agcaggcaca cacacatga                    39

<210> SEQ ID NO 41
<211> LENGTH: 39
<212> TYPE: DNA
<213> ORGANISM: Artificial sequence
<220> FEATURE:
<223> OTHER INFORMATION: Ostreopsis ovata Clade

<400> SEQUENCE: 41
tttttttttt ttttggacaa agctggtggg tacataagg                    39

<210> SEQ ID NO 42
<211> LENGTH: 40
<212> TYPE: DNA
<213> ORGANISM: Artificial sequence
<220> FEATURE:
<223> OTHER INFORMATION: Pseudo-nitzschia

<400> SEQUENCE: 42
tttttttttt tttttagtac agcgcaatca ctcaaagagc                   40

<210> SEQ ID NO 43
<211> LENGTH: 40
<212> TYPE: DNA
<213> ORGANISM: Artificial sequence
<220> FEATURE:
<223> OTHER INFORMATION: Pseudo-nitzschia + Fragilariopsis

<400> SEQUENCE: 43
tttttttttt tttttcagat tccacccaaa catggcagac                   40

<210> SEQ ID NO 44
<211> LENGTH: 40
<212> TYPE: DNA
<213> ORGANISM: Artificial sequence
<220> FEATURE:
<223> OTHER INFORMATION: Pseudo-nitzschia + Fragilariopsis

<400> SEQUENCE: 44
```
tttttttttt tttttattcc acccaaacat ggcagaccag                         40

<210> SEQ ID NO 45
<211> LENGTH: 41
<212> TYPE: DNA
<213> ORGANISM: Artificial sequence
<220> FEATURE:
<223> OTHER INFORMATION: Pseudo-nitzschia no P. pungens

<400> SEQUENCE: 45
tttttttttt tttttatgc tgtgctattt gcaggcaggg g                        41

<210> SEQ ID NO 46
<211> LENGTH: 39
<212> TYPE: DNA
<213> ORGANISM: Artificial sequence
<220> FEATURE:
<223> OTHER INFORMATION: Pseudo-nitzschia + some Fragilariopsis

<400> SEQUENCE: 46
tttttttttt ttttgcaaa ggccgactgg acacaccac                           39

<210> SEQ ID NO 47
<211> LENGTH: 40
<212> TYPE: DNA
<213> ORGANISM: Artificial sequence
<220> FEATURE:
<223> OTHER INFORMATION: Pseudo-nitzschia fraudulenta, P.
      subfraudulenta, P calliantha+P. australis+P. delicatissima+P.
      galaxiae (clade1)+P. multiseries

<400> SEQUENCE: 47
tttttttttt tttttctac caggcggacg ggagtttcac                          40

<210> SEQ ID NO 48
<211> LENGTH: 41
<212> TYPE: DNA
<213> ORGANISM: Artificial sequence
<220> FEATURE:
<223> OTHER INFORMATION: Pseudo-nitzschia fraudulenta+P.
      subfraudulenta+P. multistriata+P. galaxiae (clade1)+P. australis+
      P. multiseries+P. delicatissima

<400> SEQUENCE: 48
tttttttttt tttttacggg agtttcaccc tctcagctgt c                       41

<210> SEQ ID NO 49
<211> LENGTH: 37
<212> TYPE: DNA
<213> ORGANISM: Artificial sequence
<220> FEATURE:
<223> OTHER INFORMATION: Pseudo-nitzschia multistriata + P. calliantha+
      P. australis+P. mutliseries+P. fraudulenta+P. cf. delicatissima
      clade4

<400> SEQUENCE: 49
tttttttttt ttttacagc gcccaagcca caagtgg                             37

<210> SEQ ID NO 50
<211> LENGTH: 41
<212> TYPE: DNA
<213> ORGANISM: Artificial sequence
<220> FEATURE:
<223> OTHER INFORMATION: Karenia

<400> SEQUENCE: 50 ttttttttttt tttttcagta tcgcatccag atcaaaacct g    41

<210> SEQ ID NO 51
<211> LENGTH: 40
<212> TYPE: DNA
<213> ORGANISM: Artificial sequence
<220> FEATURE:
<223> OTHER INFORMATION: Alexandrium

<400> SEQUENCE: 51
tttttttttt tttttttacc acccactttg cattccaatg    40

<210> SEQ ID NO 52
<211> LENGTH: 39
<212> TYPE: DNA
<213> ORGANISM: Artificial sequence
<220> FEATURE:
<223> OTHER INFORMATION: Dinophysis in part

<400> SEQUENCE: 52
tttttttttt ttttttacttg cgttgtggca gcaaccaat    39

<210> SEQ ID NO 53
<211> LENGTH: 39
<212> TYPE: DNA
<213> ORGANISM: Artificial sequence
<220> FEATURE:
<223> OTHER INFORMATION: Dinophysis

<400> SEQUENCE: 53
tttttttttt tttttgcag ccagacaaac actaaagct    39

<210> SEQ ID NO 54
<211> LENGTH: 40
<212> TYPE: DNA
<213> ORGANISM: Artificial sequence
<220> FEATURE:
<223> OTHER INFORMATION: Pseudochattonella (genus)

<400> SEQUENCE: 54
tttttttttt tttttaatg accacccttc gaatcgcttc    40

<210> SEQ ID NO 55
<211> LENGTH: 40
<212> TYPE: DNA
<213> ORGANISM: Artificial sequence
<220> FEATURE:
<223> OTHER INFORMATION: Pseudochattonella (genus)

<400> SEQUENCE: 55
tttttttttt tttttcgtga aaacgcccgg cattgttatt    40

<210> SEQ ID NO 56
<211> LENGTH: 40
<212> TYPE: DNA
<213> ORGANISM: Artificial sequence
<220> FEATURE:
<223> OTHER INFORMATION: Pseudochattonella (genus)

<400> SEQUENCE: 56
tttttttttt ttttttacgac ccacgttcac agattaccca    40

<210> SEQ ID NO 57
<211> LENGTH: 42
<212> TYPE: DNA
<213> ORGANISM: Artificial sequence

```
<220> FEATURE:
<223> OTHER INFORMATION: Dinophysis genus sensu stricto

<400> SEQUENCE: 57
tttttttttt tttttcacga tgtgatttaa cacagattac cc                          42

<210> SEQ ID NO 58
<211> LENGTH: 40
<212> TYPE: DNA
<213> ORGANISM: Artificial sequence
<220> FEATURE:
<223> OTHER INFORMATION: Dinophysis genus sensu stricto

<400> SEQUENCE: 58
tttttttttt tttttcggag tcggattgtt gggcatgtat                             40

<210> SEQ ID NO 59
<211> LENGTH: 40
<212> TYPE: DNA
<213> ORGANISM: Artificial sequence
<220> FEATURE:
<223> OTHER INFORMATION: all Dinophysis

<400> SEQUENCE: 59
tttttttttt tttttatcgc cagttggtac catgcaattc                             40

<210> SEQ ID NO 60
<211> LENGTH: 40
<212> TYPE: DNA
<213> ORGANISM: Artificial sequence
<220> FEATURE:
<223> OTHER INFORMATION: Karlodinium genus

<400> SEQUENCE: 60
tttttttttt tttttggaac gtgactctta gaaagcacac                             40

<210> SEQ ID NO 61
<211> LENGTH: 40
<212> TYPE: DNA
<213> ORGANISM: Artificial sequence
<220> FEATURE:
<223> OTHER INFORMATION: Karenia genus

<400> SEQUENCE: 61
tttttttttt tttttcggt tgctggtgca gatatcccag                              40

<210> SEQ ID NO 62
<211> LENGTH: 42
<212> TYPE: DNA
<213> ORGANISM: Artificial sequence
<220> FEATURE:
<223> OTHER INFORMATION: Azadinium Genus

<400> SEQUENCE: 62
tttttttttt tttttcaatc tcatcaagaa cactggttcc at                          42

<210> SEQ ID NO 63
<211> LENGTH: 40
<212> TYPE: DNA
<213> ORGANISM: Artificial sequence
<220> FEATURE:
<223> OTHER INFORMATION: Azadinium Genus

<400> SEQUENCE: 63
tttttttttt tttttaagac aagaaacacc acgcacatct                             40
```

<210> SEQ ID NO 64
<211> LENGTH: 37
<212> TYPE: DNA
<213> ORGANISM: Artificial sequence
<220> FEATURE:
<223> OTHER INFORMATION: Azadinium Genus

<400> SEQUENCE: 64
tttttttttt tttttccttc cacagagtcg ggtatgg                                37

<210> SEQ ID NO 65
<211> LENGTH: 39
<212> TYPE: DNA
<213> ORGANISM: Artificial sequence
<220> FEATURE:
<223> OTHER INFORMATION: Azadinium Genus + Karenia. mikimoitoi

<400> SEQUENCE: 65
tttttttttt tttttaaccc ttccacagag tcgggtatg                              39

<210> SEQ ID NO 66
<211> LENGTH: 40
<212> TYPE: DNA
<213> ORGANISM: Artificial sequence
<220> FEATURE:
<223> OTHER INFORMATION: Prorocentrum

<400> SEQUENCE: 66
tttttttttt tttttctcca ttggcgatgc atctcgagac                             40

<210> SEQ ID NO 67
<211> LENGTH: 40
<212> TYPE: DNA
<213> ORGANISM: Artificial sequence
<220> FEATURE:
<223> OTHER INFORMATION: Chattonella genus

<400> SEQUENCE: 67
tttttttttt tttttctcct tgcgaagccg accgatcact                             40

<210> SEQ ID NO 68
<211> LENGTH: 40
<212> TYPE: DNA
<213> ORGANISM: Artificial sequence
<220> FEATURE:
<223> OTHER INFORMATION: Chattonella genus

<400> SEQUENCE: 68
tttttttttt tttttgcag actccttgcg aagccgaccg                              40

<210> SEQ ID NO 69
<211> LENGTH: 40
<212> TYPE: DNA
<213> ORGANISM: Artificial sequence
<220> FEATURE:
<223> OTHER INFORMATION: Chattonella genus

<400> SEQUENCE: 69
tttttttttt tttttaagcg ccttccccaa ggatggcaag                             40

<210> SEQ ID NO 70
<211> LENGTH: 40
<212> TYPE: DNA
<213> ORGANISM: Artificial sequence
<220> FEATURE:
<223> OTHER INFORMATION: Alexandrium NA,WE,TA,

<400> SEQUENCE: 70
tttttttttt ttttgtatt caaggccaaa cacctgcttg                                40

<210> SEQ ID NO 71
<211> LENGTH: 40
<212> TYPE: DNA
<213> ORGANISM: Alexandrium minutum

<400> SEQUENCE: 71
tttttttttt tttttccttt ccaggcaagg ttgcaaactc                                40

<210> SEQ ID NO 72
<211> LENGTH: 40
<212> TYPE: DNA
<213> ORGANISM: Artificial sequence
<220> FEATURE:
<223> OTHER INFORMATION: Alexandrium tamarense (NA)

<400> SEQUENCE: 72
tttttttttt tttttcaagt gcaacactcc caccaagcaa                                40

<210> SEQ ID NO 73
<211> LENGTH: 40
<212> TYPE: DNA
<213> ORGANISM: Artificial sequence
<220> FEATURE:
<223> OTHER INFORMATION: Alexandrium tamarense (NA)

<400> SEQUENCE: 73
tttttttttt tttttagtgc aacactccca ccaagcaaat                                40

<210> SEQ ID NO 74
<211> LENGTH: 40
<212> TYPE: DNA
<213> ORGANISM: Artificial sequence
<220> FEATURE:
<223> OTHER INFORMATION: Alexandrium tamarense (TA)

<400> SEQUENCE: 74
tttttttttt tttttgcaag cactacaatc tcactgagga                                40

<210> SEQ ID NO 75
<211> LENGTH: 40
<212> TYPE: DNA
<213> ORGANISM: Alexandrium ostenfeldii

<400> SEQUENCE: 75
tttttttttt tttttcattc caatgcccac aggcaaatta                                40

<210> SEQ ID NO 76
<211> LENGTH: 40
<212> TYPE: DNA
<213> ORGANISM: Alexandrium ostenfeldii

<400> SEQUENCE: 76
tttttttttt tttttgaatc accaaggttc caagcagagc                                40

<210> SEQ ID NO 77
<211> LENGTH: 40
<212> TYPE: DNA
<213> ORGANISM: Artificial sequence
<220> FEATURE:
<223> OTHER INFORMATION: Prymnesium (= Chrysochromulina) polylepis

<400> SEQUENCE: 77
tttttttttt tttttttatag tttcccataa ggtgccgacg                                40

<210> SEQ ID NO 78
<211> LENGTH: 34
<212> TYPE: DNA
<213> ORGANISM: Prymnesium parvum

<400> SEQUENCE: 78
tttttttttt tttttcagc cgacgccgag cgcg                                        34

<210> SEQ ID NO 79
<211> LENGTH: 40
<212> TYPE: DNA
<213> ORGANISM: Prymnesium parvum

<400> SEQUENCE: 79
tttttttttt tttttaagaa gtgctcgcca acgaggtgtt                                 40

<210> SEQ ID NO 80
<211> LENGTH: 40
<212> TYPE: DNA
<213> ORGANISM: Artificial sequence
<220> FEATURE:
<223> OTHER INFORMATION: Karenia mikimotoi and some Karenia brevis

<400> SEQUENCE: 80
tttttttttt tttttagcag aagatcgcag gcaagcacac                                 40

<210> SEQ ID NO 81
<211> LENGTH: 40
<212> TYPE: DNA
<213> ORGANISM: Karenia brevis

<400> SEQUENCE: 81
tttttttttt tttttagcag aagattgcaa gcaagcacac                                 40

<210> SEQ ID NO 82
<211> LENGTH: 40
<212> TYPE: DNA
<213> ORGANISM: Karenia brevis

<400> SEQUENCE: 82
tttttttttt tttttacatg ctcctggcac tagcaacctt                                 40

<210> SEQ ID NO 83
<211> LENGTH: 40
<212> TYPE: DNA
<213> ORGANISM: Artificial sequence
<220> FEATURE:
<223> OTHER INFORMATION: competitor Karenia brevis

<400> SEQUENCE: 83
tttttttttt tttttacatg ctcctggcac tagcaccctt                                 40

<210> SEQ ID NO 84
<211> LENGTH: 40
<212> TYPE: DNA
<213> ORGANISM: Karenia mikimotoi

<400> SEQUENCE: 84
tttttttttt tttttcttca tgcagagcag aagatcgcag                                 40

<210> SEQ ID NO 85
<211> LENGTH: 40
<212> TYPE: DNA
<213> ORGANISM: Karlodinium veneficium

<400> SEQUENCE: 85
tttttttttt tttttaattc aagcccagag ggcccaattt                40

<210> SEQ ID NO 86
<211> LENGTH: 40
<212> TYPE: DNA
<213> ORGANISM: Karlodinium veneficium

<400> SEQUENCE: 86
tttttttttt tttttggaaa tcagtttaga catgagttct                40

<210> SEQ ID NO 87
<211> LENGTH: 40
<212> TYPE: DNA
<213> ORGANISM: Karlodinium veneficium

<400> SEQUENCE: 87
tttttttttt tttttagag ttttcctcaa atctgaaccg                 40

<210> SEQ ID NO 88
<211> LENGTH: 40
<212> TYPE: DNA
<213> ORGANISM: Karlodinium veneficium

<400> SEQUENCE: 88
tttttttttt tttttcagag ggcccaattt ccaagctgag                40

<210> SEQ ID NO 89
<211> LENGTH: 40
<212> TYPE: DNA
<213> ORGANISM: Karlodinium veneficium

<400> SEQUENCE: 89
tttttttttt tttttgcgac gagtaacaga agctacaagc                40

<210> SEQ ID NO 90
<211> LENGTH: 40
<212> TYPE: DNA
<213> ORGANISM: Karlodinium veneficium

<400> SEQUENCE: 90
tttttttttt tttttgaaag actacaattc aagcccagag                40

<210> SEQ ID NO 91
<211> LENGTH: 40
<212> TYPE: DNA
<213> ORGANISM: Karenia brevis

<400> SEQUENCE: 91
tttttttttt tttttcgttc aggatctgaa cactgcggca                40

<210> SEQ ID NO 92
<211> LENGTH: 40
<212> TYPE: DNA
<213> ORGANISM: Karenia brevis

<400> SEQUENCE: 92
tttttttttt tttttcaacg ttcaggatct gaacactgcg                40

```
<210> SEQ ID NO 93
<211> LENGTH: 40
<212> TYPE: DNA
<213> ORGANISM: Artificial sequence
<220> FEATURE:
<223> OTHER INFORMATION: Karenia brevis+ Karenia mikimotoi

<400> SEQUENCE: 93
tttttttttt tttttgcagt gcgaccagac acacagtgag                               40

<210> SEQ ID NO 94
<211> LENGTH: 40
<212> TYPE: DNA
<213> ORGANISM: Artificial sequence
<220> FEATURE:
<223> OTHER INFORMATION: Karenia brevis+ Karenia mikimotoi

<400> SEQUENCE: 94 ttttttttttt tttttcggag cagtgcgacc agacacacag                             40

<210> SEQ ID NO 95
<211> LENGTH: 40
<212> TYPE: DNA
<213> ORGANISM: Artificial sequence
<220> FEATURE:
<223> OTHER INFORMATION: Prorocentrum planktonic clade

<400> SEQUENCE: 95 ttttttttttt ttttttgcaa tcagaaccca tcctagtcct                             40

<210> SEQ ID NO 96
<211> LENGTH: 40
<212> TYPE: DNA
<213> ORGANISM: Prorocentrum lima

<400> SEQUENCE: 96 ttttttttttt tttttagct ctagcatttc cacgggtatc                              40

<210> SEQ ID NO 97
<211> LENGTH: 40
<212> TYPE: DNA
<213> ORGANISM: Prorocentrum lima

<400> SEQUENCE: 97 ttttttttttt tttttacac cccaattgcc tcgtaggcag                              40

<210> SEQ ID NO 98
<211> LENGTH: 40
<212> TYPE: DNA
<213> ORGANISM: Prorocentrum minimum

<400> SEQUENCE: 98 ttttttttttt tttttccgc aaatgagttc tgccaaggct                              40

<210> SEQ ID NO 99
<211> LENGTH: 40
<212> TYPE: DNA
<213> ORGANISM: Artificial sequence
<220> FEATURE:
<223> OTHER INFORMATION: Prorocentrum belizaneum & P. maculosum

<400> SEQUENCE: 99 ttttttttttt ttttattta tcgccagcgg acgccatacg                              40
```

```
<210> SEQ ID NO 100
<211> LENGTH: 40
<212> TYPE: DNA
<213> ORGANISM: Prorocentrum maculosum

<400> SEQUENCE: 100
tttttttttt ttttttcccc cgttcattcg cgcattactg                           40

<210> SEQ ID NO 101
<211> LENGTH: 47
<212> TYPE: DNA
<213> ORGANISM: Artificial sequence
<220> FEATURE:
<223> OTHER INFORMATION: Prororocentrum maculosum 2

<400> SEQUENCE: 101
tttttttttt tttttggtg ccctttatcc aagaggcccg cacctgc                    47

<210> SEQ ID NO 102
<211> LENGTH: 40
<212> TYPE: DNA
<213> ORGANISM: Artificial sequence
<220> FEATURE:
<223> OTHER INFORMATION: Prorocentrum rathymum and P. mexicanum

<400> SEQUENCE: 102
tttttttttt tttttgacaa gaagcgctgc aaccagacac                           40

<210> SEQ ID NO 103
<211> LENGTH: 40
<212> TYPE: DNA
<213> ORGANISM: Artificial sequence
<220> FEATURE:
<223> OTHER INFORMATION: Prorocentrum rathymum and P. mexicanum

<400> SEQUENCE: 103
tttttttttt tttttgtgt cagggaagcg cccagtcacc                            40

<210> SEQ ID NO 104
<211> LENGTH: 40
<212> TYPE: DNA
<213> ORGANISM: Artificial sequence
<220> FEATURE:
<223> OTHER INFORMATION: Dinophysis acuminata+ D. dens+D. sacculus

<400> SEQUENCE: 104
tttttttttt tttttatgct catcgcaacc acagcaaagc                           40

<210> SEQ ID NO 105
<211> LENGTH: 40
<212> TYPE: DNA
<213> ORGANISM: Artificial sequence
<220> FEATURE:
<223> OTHER INFORMATION: Dinophysis acuta+D.fortii

<400> SEQUENCE: 105
tttttttttt tttttcatcg caaccacaag tcctgcttga                           40

<210> SEQ ID NO 106
<211> LENGTH: 40
<212> TYPE: DNA
<213> ORGANISM: Dinophysis acuminata

<400> SEQUENCE: 106
tttttttttt ttttttcac cagactttcc acggcaacgc                            40
```

<210> SEQ ID NO 107
<211> LENGTH: 40
<212> TYPE: DNA
<213> ORGANISM: Dinophysis acuta

<400> SEQUENCE: 107
tttttttttt tttttcagac tttccacggc aacaattagg                        40

<210> SEQ ID NO 108
<211> LENGTH: 40
<212> TYPE: DNA
<213> ORGANISM: Dinophysis norvegica

<400> SEQUENCE: 108
tttttttttt tttttccac ggcaacgttc aggaactaaa                         40

<210> SEQ ID NO 109
<211> LENGTH: 40
<212> TYPE: DNA
<213> ORGANISM: Phalacroma rotundatum

<400> SEQUENCE: 109
tttttttttt tttttggcaa cgctcaggaa ctaaacactg                        40

<210> SEQ ID NO 110
<211> LENGTH: 40
<212> TYPE: DNA
<213> ORGANISM: Artificial sequence
<220> FEATURE:
<223> OTHER INFORMATION: Pseudo-nitzschia australis, P. seriata, P.
      multiseries

<400> SEQUENCE: 110
tttttttttt tttttgctct tccaaaggat tcaaccaacc                        40

<210> SEQ ID NO 111
<211> LENGTH: 40
<212> TYPE: DNA
<213> ORGANISM: Artificial sequence
<220> FEATURE:
<223> OTHER INFORMATION: Pseudo-nitzschia australis & P. multistriata

<400> SEQUENCE: 111
tttttttttt ttttttgac aaatgactca ctccaccagg                         40

<210> SEQ ID NO 112
<211> LENGTH: 40
<212> TYPE: DNA
<213> ORGANISM: Artificial sequence
<220> FEATURE:
<223> OTHER INFORMATION: Pseudo-nitzschia australis & P. seriata, P.
      delicatissima, P. calliantha, P. multiseries

<400> SEQUENCE: 112
tttttttttt tttttgactg cgctcttcca aaggattcaa                        40

<210> SEQ ID NO 113
<211> LENGTH: 39
<212> TYPE: DNA
<213> ORGANISM: Artificial sequence
<220> FEATURE:
<223> OTHER INFORMATION: Pseudo-nitzschia australis & P. seriata, P.
      calliantha

<400> SEQUENCE: 113
tttttttttt tttttgccca aaccacaagt ggccgggga                                39

<210> SEQ ID NO 114
<211> LENGTH: 40
<212> TYPE: DNA
<213> ORGANISM: Artificial sequence
<220> FEATURE:
<223> OTHER INFORMATION: Pseudo-nitzschia caciantha + P. australis

<400> SEQUENCE: 114
tttttttttt tttttttcgt ctgatagagt caaacccagt                               40

<210> SEQ ID NO 115
<211> LENGTH: 40
<212> TYPE: DNA
<213> ORGANISM: Artificial sequence
<220> FEATURE:
<223> OTHER INFORMATION: Pseudo-nitzschia calliantha

<400> SEQUENCE: 115
tttttttttt tttttattcg gcaccaaaaa gtgcagattt                               40

<210> SEQ ID NO 116
<211> LENGTH: 40
<212> TYPE: DNA
<213> ORGANISM: Artificial sequence
<220> FEATURE:
<223> OTHER INFORMATION: Pseudo-nitzschia calliantha

<400> SEQUENCE: 116
tttttttttt tttttgtcta ctcaagtcaa acccagtgct                               40

<210> SEQ ID NO 117
<211> LENGTH: 40
<212> TYPE: DNA
<213> ORGANISM: Artificial sequence
<220> FEATURE:
<223> OTHER INFORMATION: Pseudo-nitzschia mannii+P. australis

<400> SEQUENCE: 117
tttttttttt tttttggcgc ttaaacagcg cagatttaca                               40

<210> SEQ ID NO 118
<211> LENGTH: 40
<212> TYPE: DNA
<213> ORGANISM: Artificial sequence
<220> FEATURE:
<223> OTHER INFORMATION: Pseudo-nitzschia mannii

<400> SEQUENCE: 118
tttttttttt tttttaacg ccaaagtctt cagaccacaa                                40

<210> SEQ ID NO 119
<211> LENGTH: 41
<212> TYPE: DNA
<213> ORGANISM: Artificial sequence
<220> FEATURE:
<223> OTHER INFORMATION: Pseudo-nitzschia mannii+P. australis

<400> SEQUENCE: 119
tttttttttt tttttcttca gaccacaatt cggcgcttaa a                             41

<210> SEQ ID NO 120
<211> LENGTH: 41
<212> TYPE: DNA
<213> ORGANISM: Artificial sequence

```
<220> FEATURE:
<223> OTHER INFORMATION: Pseudo-nitzschia mannii

<400> SEQUENCE: 120
tttttttttt tttttatttc gtctgctcga gtcaaaacca g          41

<210> SEQ ID NO 121
<211> LENGTH: 40
<212> TYPE: DNA
<213> ORGANISM: Artificial sequence
<220> FEATURE:
<223> OTHER INFORMATION: Pseudo-nitzschia delicatissima + P. austalis

<400> SEQUENCE: 121
tttttttttt tttttttccaa ccactgttac tttcattacg           40

<210> SEQ ID NO 122
<211> LENGTH: 40
<212> TYPE: DNA
<213> ORGANISM: Artificial sequence
<220> FEATURE:
<223> OTHER INFORMATION: Pseudo-nitzschia cf. delicatissima Clade4+P.
      galaxiae (clade2)+P. australis

<400> SEQUENCE: 122
tttttttttt ttttttgac aacgactcac tctaccaggc             40

<210> SEQ ID NO 123
<211> LENGTH: 40
<212> TYPE: DNA
<213> ORGANISM: Artificial sequence
<220> FEATURE:
<223> OTHER INFORMATION: Pseudo-nitzschia cf. delicatissima Clade4

<400> SEQUENCE: 123
tttttttttt tttttgattg tgcaaatatc caaccactgt            40

<210> SEQ ID NO 124
<211> LENGTH: 39
<212> TYPE: DNA
<213> ORGANISM: Artificial sequence
<220> FEATURE:
<223> OTHER INFORMATION: Pseudo-nitzschia cf. delicatissima Clade4+P.
      galaxiae (clade2)+P. australis

<400> SEQUENCE: 124
tttttttttt tttttgaca acgactcact ctaccaggc              39

<210> SEQ ID NO 125
<211> LENGTH: 40
<212> TYPE: DNA
<213> ORGANISM: Artificial sequence
<220> FEATURE:
<223> OTHER INFORMATION: Pseudo-nitzschia dolorosa +P. micropora

<400> SEQUENCE: 125
tttttttttt tttttaatg ttaaagtcta tagaccacaa             40

<210> SEQ ID NO 126
<211> LENGTH: 40
<212> TYPE: DNA
<213> ORGANISM: Artificial sequence
<220> FEATURE:
<223> OTHER INFORMATION: Pseudo-nitzschia dolorosa+P. micropora+P.
      australis

<400> SEQUENCE: 126
```
tttttttttt tttttgacaa aaactcactc taccaggcgg                        40

<210> SEQ ID NO 127
<211> LENGTH: 40
<212> TYPE: DNA
<213> ORGANISM: Artificial sequence
<220> FEATURE:
<223> OTHER INFORMATION: competitor Pseudo-nitzschia dolorosa

<400> SEQUENCE: 127
tttttttttt tttttgacaa gaactcactc taccaggcgg                        40

<210> SEQ ID NO 128
<211> LENGTH: 39
<212> TYPE: DNA
<213> ORGANISM: Artificial sequence
<220> FEATURE:
<223> OTHER INFORMATION: Pseudo-nitzschia arenysensis+ P. multistriata+
      P. australis+P. galaxiae (clade2)

<400> SEQUENCE: 128
tttttttttt ttttttgac aacgactcac tccaccagg                          39

<210> SEQ ID NO 129
<211> LENGTH: 40
<212> TYPE: DNA
<213> ORGANISM: Artificial sequence
<220> FEATURE:
<223> OTHER INFORMATION: Pseudo-nitzschia delicatissima +P calliantha

<400> SEQUENCE: 129
tttttttttt tttttccact gttactttca ttacgcaccg                        40

<210> SEQ ID NO 130
<211> LENGTH: 41
<212> TYPE: DNA
<213> ORGANISM: Artificial sequence
<220> FEATURE:
<223> OTHER INFORMATION: Pseudo-nitzschia galaxiae, all clades

<400> SEQUENCE: 130
tttttttttt tttttccaca tcacaagtga caagggaaat a                      41

<210> SEQ ID NO 131
<211> LENGTH: 40
<212> TYPE: DNA
<213> ORGANISM: Artificial sequence
<220> FEATURE:
<223> OTHER INFORMATION: Pseudo-nitzschia galaxiae, all clades

<400> SEQUENCE: 131
tttttttttt tttttccaaa ggaatcaacc aaagcaaacc                        40

<210> SEQ ID NO 132
<211> LENGTH: 40
<212> TYPE: DNA
<213> ORGANISM: Artificial sequence
<220> FEATURE:
<223> OTHER INFORMATION: Pseudo-nitzschia galaxiae, all clades

<400> SEQUENCE: 132
tttttttttt tttttttcgt ctgcttaagt caaaaccagt                        40

<210> SEQ ID NO 133
<211> LENGTH: 39

```
<212> TYPE: DNA
<213> ORGANISM: Artificial sequence
<220> FEATURE:
<223> OTHER INFORMATION: Pseudo-nitzschia multiseries+P. australis

<400> SEQUENCE: 133
tttttttttt tttttgatc cgtcgccgcc aaaaggcat                    39

<210> SEQ ID NO 134
<211> LENGTH: 40
<212> TYPE: DNA
<213> ORGANISM: Artificial sequence
<220> FEATURE:
<223> OTHER INFORMATION: Pseudo-nitzschia multiseries+P. australis

<400> SEQUENCE: 134
tttttttttt tttttttgac aaatgactca ctctgccagg                  40

<210> SEQ ID NO 135
<211> LENGTH: 39
<212> TYPE: DNA
<213> ORGANISM: Artificial sequence
<220> FEATURE:
<223> OTHER INFORMATION: Pseudo-nitzschia multiseries+P. calliantha+P.
      australis

<400> SEQUENCE: 135
tttttttttt tttttaccca aactcacgca agcccacag                   39

<210> SEQ ID NO 136
<211> LENGTH: 39
<212> TYPE: DNA
<213> ORGANISM: Artificial sequence
<220> FEATURE:
<223> OTHER INFORMATION: Pseudo-nitzschia multiseries+P. calliantha

<400> SEQUENCE: 136
tttttttttt tttttgcgcc caagccacaa gtggctagg                   39

<210> SEQ ID NO 137
<211> LENGTH: 40
<212> TYPE: DNA
<213> ORGANISM: Artificial sequence
<220> FEATURE:
<223> OTHER INFORMATION: Pseudo-nitzschiamultiseries+ P. calliantha+P.
      australis

<400> SEQUENCE: 137
tttttttttt tttttaaatg actcactctg ccaggcggac                  40

<210> SEQ ID NO 138
<211> LENGTH: 40
<212> TYPE: DNA
<213> ORGANISM: Artificial sequence
<220> FEATURE:
<223> OTHER INFORMATION: Pseudo-nitzschia multistriata+P. australis

<400> SEQUENCE: 138
tttttttttt tttttaaccc aaactcacga aagctcacag                  40

<210> SEQ ID NO 139
<211> LENGTH: 40
<212> TYPE: DNA
<213> ORGANISM: Artificial sequence
<220> FEATURE:
<223> OTHER INFORMATION: Pseudo-nitzschia pseudodelicatissima+P.
      cuspidata
```

<400> SEQUENCE: 139
tttttttttt ttttttttcca aagggatcaa ccaagacaaa            40

<210> SEQ ID NO 140
<211> LENGTH: 40
<212> TYPE: DNA
<213> ORGANISM: Artificial sequence
<220> FEATURE:
<223> OTHER INFORMATION: Pseudo-nitzschia pseudodelicatissima+P.
      cuspidata

<400> SEQUENCE: 140
tttttttttt tttttcccgg cagataacgt caaggtctat            40

<210> SEQ ID NO 141
<211> LENGTH: 39
<212> TYPE: DNA
<213> ORGANISM: Artificial sequence
<220> FEATURE:
<223> OTHER INFORMATION: Pseudo-nitzschia pungens+P. calliantha

<400> SEQUENCE: 141
tttttttttt tttttatggg caccctcagt acgacaact             39

<210> SEQ ID NO 142
<211> LENGTH: 38
<212> TYPE: DNA
<213> ORGANISM: Artificial sequence
<220> FEATURE:
<223> OTHER INFORMATION: Pseudo-nitzschia pungens+ P. calliantha+P.
      multiseries+P. australis

<400> SEQUENCE: 142
tttttttttt tttttctcac gcaagtccac agcgccca              38

<210> SEQ ID NO 143
<211> LENGTH: 39
<212> TYPE: DNA
<213> ORGANISM: Artificial sequence
<220> FEATURE:
<223> OTHER INFORMATION: Pseudo-nitzschia pungens+P. calliantha+P.
      australis

<400> SEQUENCE: 143
tttttttttt tttttactca ctttaccagg cggacggga             39

<210> SEQ ID NO 144
<211> LENGTH: 40
<212> TYPE: DNA
<213> ORGANISM: Artificial sequence
<220> FEATURE:
<223> OTHER INFORMATION: Pseudo-nitzschia seriata, P. calliantha, P.
      multiseries, P. australis+P. multistriata

<400> SEQUENCE: 144
tttttttttt tttttgacaa atgactcact ctaccaggcg            40

<210> SEQ ID NO 145
<211> LENGTH: 45
<212> TYPE: DNA
<213> ORGANISM: Chloromorum toxicum

<400> SEQUENCE: 145
tttttttttt tttttttacga acaacacaat acacaatccg ctagg     45

<210> SEQ ID NO 146
<211> LENGTH: 41
<212> TYPE: DNA
<213> ORGANISM: Artificial sequence
<220> FEATURE:
<223> OTHER INFORMATION: Chloromorum toxicum, Karenia mikimoitoi,
      Gymnodinium catenatum

<400> SEQUENCE: 146
tttttttttt tttttgatga ggatcgcaac accaacaacc t                    41

<210> SEQ ID NO 147
<211> LENGTH: 40
<212> TYPE: DNA
<213> ORGANISM: Chloromorum toxicum

<400> SEQUENCE: 147
tttttttttt tttttctagg aaaggatcgg cggctcatac                      40

<210> SEQ ID NO 148
<211> LENGTH: 43
<212> TYPE: DNA
<213> ORGANISM: Chloromorum toxicum

<400> SEQUENCE: 148
tttttttttt tttttccac cgaaatggtc aggagtttat gca                   43

<210> SEQ ID NO 149
<211> LENGTH: 45
<212> TYPE: DNA
<213> ORGANISM: Gymnodonium catenatum

<400> SEQUENCE: 149
tttttttttt tttttgcatt tttaaaagat tacccaatcc tgtcg                45

<210> SEQ ID NO 150
<211> LENGTH: 42
<212> TYPE: DNA
<213> ORGANISM: Gymnodonium catenatum

<400> SEQUENCE: 150
tttttttttt tttttcgtat agttaacggc ctccaatctc ta                   42

<210> SEQ ID NO 151
<211> LENGTH: 39
<212> TYPE: DNA
<213> ORGANISM: Gymnodonium catenatum

<400> SEQUENCE: 151
tttttttttt tttttttaca tctacgcccc tgctggcag                       39

<210> SEQ ID NO 152
<211> LENGTH: 39
<212> TYPE: DNA
<213> ORGANISM: Gymnodonium catenatum

<400> SEQUENCE: 152
tttttttttt tttttcaccg ccccgctttc gctggaata                       39

<210> SEQ ID NO 153
<211> LENGTH: 40
<212> TYPE: DNA
<213> ORGANISM: Heterosigma akashiwo

<400> SEQUENCE: 153
tttttttttt tttttcgac cgaagtcgat tcgcacagtt                40

<210> SEQ ID NO 154
<211> LENGTH: 40
<212> TYPE: DNA
<213> ORGANISM: Heterosigma akashiwo

<400> SEQUENCE: 154
tttttttttt tttttcttga atgaaccatc gaccgaagtc                40

<210> SEQ ID NO 155
<211> LENGTH: 40
<212> TYPE: DNA
<213> ORGANISM: Heterosigma akashiwo

<400> SEQUENCE: 155
tttttttttt tttttatgtt gaaacgctcc aggccccacg                40

<210> SEQ ID NO 156
<211> LENGTH: 40
<212> TYPE: DNA
<213> ORGANISM: Heterosigma akashiwo

<400> SEQUENCE: 156
tttttttttt tttttggacc acgactgagc acgcaccttt                40

<210> SEQ ID NO 157
<211> LENGTH: 40
<212> TYPE: DNA
<213> ORGANISM: Heterosigma akashiwo

<400> SEQUENCE: 157
tttttttttt tttttggagc aaaggtcctc cgtcctaacc                40

<210> SEQ ID NO 158
<211> LENGTH: 40
<212> TYPE: DNA
<213> ORGANISM: Heterosigma akashiwo

<400> SEQUENCE: 158
tttttttttt tttttaccag catacccgag agaggaacgc                40

<210> SEQ ID NO 159
<211> LENGTH: 40
<212> TYPE: DNA
<213> ORGANISM: Heterosigma akashiwo

<400> SEQUENCE: 159
tttttttttt tttttggacc ccaggcaaga accggattgt                40

<210> SEQ ID NO 160
<211> LENGTH: 39
<212> TYPE: DNA
<213> ORGANISM: Heterosigma akashiwo

<400> SEQUENCE: 160
tttttttttt tttttactcg tcggaaacgg ctcgtacgc                39

<210> SEQ ID NO 161
<211> LENGTH: 40
<212> TYPE: DNA
<213> ORGANISM: Pseudochattonella verruculosa

<400> SEQUENCE: 161
tttttttttt tttttaagca actcgactcc attagcacgg        40

<210> SEQ ID NO 162
<211> LENGTH: 40
<212> TYPE: DNA
<213> ORGANISM: Pseudochattonella farcimen

<400> SEQUENCE: 162
tttttttttt tttttaagca actcgactcc actaggacgg        40

<210> SEQ ID NO 163
<211> LENGTH: 40
<212> TYPE: DNA
<213> ORGANISM: Vulcanodinium rugosum

<400> SEQUENCE: 163
tttttttttt ttttttttac ccacccgcga actcgcacat        40

<210> SEQ ID NO 164
<211> LENGTH: 40
<212> TYPE: DNA
<213> ORGANISM: Vulcanodinium rugosum

<400> SEQUENCE: 164
tttttttttt ttttcaatt cagggccaat ggccccaatt        40

<210> SEQ ID NO 165
<211> LENGTH: 40
<212> TYPE: DNA
<213> ORGANISM: Vulcanodinium rugosum

<400> SEQUENCE: 165
tttttttttt tttttggcaa gcgggattgt caccctcgct        40

<210> SEQ ID NO 166
<211> LENGTH: 40
<212> TYPE: DNA
<213> ORGANISM: Fibrocapsa japonica

<400> SEQUENCE: 166
tttttttttt tttttgggta acgaaacgcc acccagattt        40

<210> SEQ ID NO 167
<211> LENGTH: 40
<212> TYPE: DNA
<213> ORGANISM: Fibrocapsa japonica

<400> SEQUENCE: 167
tttttttttt tttttccgaa ccacgacatg ccacagggtt        40

<210> SEQ ID NO 168
<211> LENGTH: 40
<212> TYPE: DNA
<213> ORGANISM: Fibrocapsa japonica

<400> SEQUENCE: 168
tttttttttt ttttttgtc accgtccacg atgccccgtt        40

<210> SEQ ID NO 169
<211> LENGTH: 42
<212> TYPE: DNA

```
<213> ORGANISM: Artificial sequence
<220> FEATURE:
<223> OTHER INFORMATION: Dino New Genus

<400> SEQUENCE: 169
tttttttttt tttttgtaca cacctgagtc cctacaagca ca                          42

<210> SEQ ID NO 170
<211> LENGTH: 40
<212> TYPE: DNA
<213> ORGANISM: Artificial sequence
<220> FEATURE:
<223> OTHER INFORMATION: Dino New Genus

<400> SEQUENCE: 170
tttttttttt tttttgagca accccgcgga gaagcgtcgt                             40

<210> SEQ ID NO 171
<211> LENGTH: 40
<212> TYPE: DNA
<213> ORGANISM: Chattonella subsalsa

<400> SEQUENCE: 171
tttttttttt tttttggacg aggaaccctc atccagattt                             40

<210> SEQ ID NO 172
<211> LENGTH: 40
<212> TYPE: DNA
<213> ORGANISM: Chattonella subsalsa

<400> SEQUENCE: 172
tttttttttt tttttgggtt atcaccgtcc atgacactgt                             40

<210> SEQ ID NO 173
<211> LENGTH: 40
<212> TYPE: DNA
<213> ORGANISM: Chattonella subsalsa

<400> SEQUENCE: 173
tttttttttt tttttcagtc caagccacga cagagaatgt                             40

<210> SEQ ID NO 174
<211> LENGTH: 40
<212> TYPE: DNA
<213> ORGANISM: Artificial sequence
<220> FEATURE:
<223> OTHER INFORMATION: Gambierdiscus clade2 with caribaeus,
      carpenteri, austalis

<400> SEQUENCE: 174
tttttttttt tttttatcct ccgtcacctg tcactgccac                             40

<210> SEQ ID NO 175
<211> LENGTH: 40
<212> TYPE: DNA
<213> ORGANISM: Artificial sequence
<220> FEATURE:
<223> OTHER INFORMATION: Gambierdiscus toxicua and pacificus, belizeanus

<400> SEQUENCE: 175
tttttttttt tttttatcct ccgtcacctg tcacagccac                             40

<210> SEQ ID NO 176
<211> LENGTH: 40
<212> TYPE: DNA
```

<213> ORGANISM: Artificial sequence
<220> FEATURE:
<223> OTHER INFORMATION: Alexandrium spp.

<400> SEQUENCE: 176
tttttttttt tttttatcct ccgtcacctg tcattgccac                40

<210> SEQ ID NO 177
<211> LENGTH: 40
<212> TYPE: DNA
<213> ORGANISM: Artificial sequence
<220> FEATURE:
<223> OTHER INFORMATION: Gambierdiscus polynesiensus to use with clade
      probe

<400> SEQUENCE: 177
tttttttttt tttttatcct ccgtcacctg ttactgccac                40

<210> SEQ ID NO 178
<211> LENGTH: 40
<212> TYPE: DNA
<213> ORGANISM: Gambierdiscus polynesiensus

<400> SEQUENCE: 178
tttttttttt tttttgggcc aggcaatgcc tgcattggtt                40

<210> SEQ ID NO 179
<211> LENGTH: 40
<212> TYPE: DNA
<213> ORGANISM: Gambierdiscus polynesiensus

<400> SEQUENCE: 179
tttttttttt tttttaccag ctgatgcacc acaagccgtt                40

<210> SEQ ID NO 180
<211> LENGTH: 40
<212> TYPE: DNA
<213> ORGANISM: Gambierdiscus polynesiensus

<400> SEQUENCE: 180
tttttttttt tttttaggtt agccagattg cccagcccctt                40

<210> SEQ ID NO 181
<211> LENGTH: 38
<212> TYPE: DNA
<213> ORGANISM: Artificial sequence
<220> FEATURE:
<223> OTHER INFORMATION: Gambierdiscus clade2 with caribaeus,
      carpenteri, austalis, polynesiensis

<400> SEQUENCE: 181
tttttttttt ttttgcattg atccatcccc atcacgac                38

<210> SEQ ID NO 182
<211> LENGTH: 39
<212> TYPE: DNA
<213> ORGANISM: Gambierdiscus belizeanus

<400> SEQUENCE: 182
tttttttttt ttttgccatg cacagcacca ttgtgggat                39

<210> SEQ ID NO 183
<211> LENGTH: 39
<212> TYPE: DNA
<213> ORGANISM: Gambierdiscus belizeanus

```
<400> SEQUENCE: 183
tttttttttt ttttgccatg cacagcacca ttgtgggat                              39

<210> SEQ ID NO 184
<211> LENGTH: 39
<212> TYPE: DNA
<213> ORGANISM: Gambierdiscus belizeanus

<400> SEQUENCE: 184
tttttttttt ttttgaagat gcttccaagc attgcctgc                              39

<210> SEQ ID NO 185
<211> LENGTH: 39
<212> TYPE: DNA
<213> ORGANISM: Gambierdiscus austalis

<400> SEQUENCE: 185
tttttttttt ttttccacga cccaggttgt ggctgtttt                              39

<210> SEQ ID NO 186
<211> LENGTH: 39
<212> TYPE: DNA
<213> ORGANISM: Gambierdiscus austalis

<400> SEQUENCE: 186
tttttttttt ttttcggacc agcaatctcc agcagaaat                              39

<210> SEQ ID NO 187
<211> LENGTH: 39
<212> TYPE: DNA
<213> ORGANISM: Gambierdiscus austalis

<400> SEQUENCE: 187
tttttttttt ttttcaacaa ccacaactca ccacaggtg                              39

<210> SEQ ID NO 188
<211> LENGTH: 39
<212> TYPE: DNA
<213> ORGANISM: Artificial sequence
<220> FEATURE:
<223> OTHER INFORMATION: Gambierdiscus new species clade

<400> SEQUENCE: 188
tttttttttt ttttattgca accaggcatc gcctgcatt                              39

<210> SEQ ID NO 189
<211> LENGTH: 39
<212> TYPE: DNA
<213> ORGANISM: Artificial sequence
<220> FEATURE:
<223> OTHER INFORMATION: Gambierdiscus new species clade

<400> SEQUENCE: 189
tttttttttt ttttgaatgc tgcaacaggg ccaaactgt                              39

<210> SEQ ID NO 190
<211> LENGTH: 39
<212> TYPE: DNA
<213> ORGANISM: Artificial sequence
<220> FEATURE:
<223> OTHER INFORMATION: Gambierdiscus new species clade

<400> SEQUENCE: 190
```

```
tttttttttt ttttcccctc tggaaaagaa tgcttgggt                                39
```

<210> SEQ ID NO 191
<211> LENGTH: 42
<212> TYPE: DNA
<213> ORGANISM: Gambierdiscus pacificus

<400> SEQUENCE: 191

```
tttttttttt ttttaccatc ccctttggac actgtcttca ct                           42
```

<210> SEQ ID NO 192
<211> LENGTH: 39
<212> TYPE: DNA
<213> ORGANISM: Gambierdiscus pacificus

<400> SEQUENCE: 192

```
tttttttttt ttttgccttc gccctagttc atccttgac                               39
```

<210> SEQ ID NO 193
<211> LENGTH: 40
<212> TYPE: DNA
<213> ORGANISM: Gambierdiscus pacificus

<400> SEQUENCE: 193

```
tttttttttt ttttccatca cggtgcagat ttcaaaagat                              40
```

<210> SEQ ID NO 194
<211> LENGTH: 39
<212> TYPE: DNA
<213> ORGANISM: Gambierdiscus carolinianus

<400> SEQUENCE: 194

```
tttttttttt ttttgctcca ggcatagcct gcgttagtt                               39
```

<210> SEQ ID NO 195
<211> LENGTH: 39
<212> TYPE: DNA
<213> ORGANISM: Gambierdiscus carolinianus

<400> SEQUENCE: 195

```
tttttttttt ttttggacca gccaacccca gcagaaatt                               39
```

<210> SEQ ID NO 196
<211> LENGTH: 39
<212> TYPE: DNA
<213> ORGANISM: Gambierdiscus carolinianus

<400> SEQUENCE: 196

```
tttttttttt ttttgaccac aatccacagc tgaactgct                               39
```

<210> SEQ ID NO 197
<211> LENGTH: 39
<212> TYPE: DNA
<213> ORGANISM: Artificial sequence
<220> FEATURE:
<223> OTHER INFORMATION: Gambierdiscus yasumotoi+fuetzleri

<400> SEQUENCE: 197

```
tttttttttt ttttccctcc agaaatatgc tcaggctgt                               39
```

<210> SEQ ID NO 198
<211> LENGTH: 39
<212> TYPE: DNA
<213> ORGANISM: Artificial sequence

```
<220> FEATURE:
<223> OTHER INFORMATION: Gambierdiscus yasumotoi+fuetzleri

<400> SEQUENCE: 198 ttttttttttt ttttccagcc attccaggca agatggaat                          39

<210> SEQ ID NO 199
<211> LENGTH: 40
<212> TYPE: DNA
<213> ORGANISM: Artificial sequence
<220> FEATURE:
<223> OTHER INFORMATION: Gambierdiscus yasumotoi+fuetzleri

<400> SEQUENCE: 199 ttttttttttt ttttgtgtta tccaagaact gagtgccact                         40

<210> SEQ ID NO 200
<211> LENGTH: 39
<212> TYPE: DNA
<213> ORGANISM: Artificial sequence
<220> FEATURE:
<223> OTHER INFORMATION: Gambierdiscus yasumotoi+fuetzleri

<400> SEQUENCE: 200 ttttttttttt ttttaaggtg ccgaaggagt catccgagt                          39

<210> SEQ ID NO 201
<211> LENGTH: 41
<212> TYPE: DNA
<213> ORGANISM: Gambierdiscus carpenteri

<400> SEQUENCE: 201 ttttttttttt ttttaatatg cttagggtgc accagatgct c                       41

<210> SEQ ID NO 202
<211> LENGTH: 40
<212> TYPE: DNA
<213> ORGANISM: Gambierdiscus carpenteri

<400> SEQUENCE: 202 ttttttttttt ttttagtggc actcagttct tggataacac                         40

<210> SEQ ID NO 203
<211> LENGTH: 39
<212> TYPE: DNA
<213> ORGANISM: Gambierdiscus carpenteri

<400> SEQUENCE: 203 ttttttttttt ttttcatggg cggaccggcc atcctctgc                          39

<210> SEQ ID NO 204
<211> LENGTH: 43
<212> TYPE: DNA
<213> ORGANISM: Gambierdiscus caribaeus

<400> SEQUENCE: 204 ttttttttttt ttttgcggac caggcatcct ctgcagaaat cca                     43

<210> SEQ ID NO 205
<211> LENGTH: 42
<212> TYPE: DNA
<213> ORGANISM: Gambierdiscus caribaeus

<400> SEQUENCE: 205
```
tttttttttt tttttttagg aaatatgctc aggctgcacc ag          42

<210> SEQ ID NO 206
<211> LENGTH: 40
<212> TYPE: DNA
<213> ORGANISM: Gambierdiscus caribaeus

<400> SEQUENCE: 206
tttttttttt ttttcttctg tatgcacagc acacacttgc            40

<210> SEQ ID NO 207
<211> LENGTH: 38
<212> TYPE: DNA
<213> ORGANISM: Gambierdiscus toxicus

<400> SEQUENCE: 207
tttttttttt tttttccatg tgcatcaacc atccacct              38

<210> SEQ ID NO 208
<211> LENGTH: 39
<212> TYPE: DNA
<213> ORGANISM: Gambierdiscus toxicus

<400> SEQUENCE: 208
tttttttttt ttttcctaac gacgaagttt gccagccat             39

<210> SEQ ID NO 209
<211> LENGTH: 39
<212> TYPE: DNA
<213> ORGANISM: Gambierdiscus toxicus

<400> SEQUENCE: 209
tttttttttt ttttcttctg cattcaaggc aaagcctgc             39

<210> SEQ ID NO 210
<211> LENGTH: 39
<212> TYPE: DNA
<213> ORGANISM: Ostreopsis siamensis

<400> SEQUENCE: 210
tttttttttt ttttaaagcc agtacgcaca ctcagtggt             39

<210> SEQ ID NO 211
<211> LENGTH: 39
<212> TYPE: DNA
<213> ORGANISM: Ostreopsis siamensis

<400> SEQUENCE: 211
tttttttttt ttttcagtgc atgatcacag ttggtgcgt             39

<210> SEQ ID NO 212
<211> LENGTH: 39
<212> TYPE: DNA
<213> ORGANISM: Ostreopsis siamensis

<400> SEQUENCE: 212
tttttttttt ttttcagtgc acacatggag cacaccaat             39

<210> SEQ ID NO 213
<211> LENGTH: 39
<212> TYPE: DNA
<213> ORGANISM: Ostreopsis lenticularis

<400> SEQUENCE: 213

```
tttttttttt ttttcaagtt ggatgcagct cctctgctt                             39

<210> SEQ ID NO 214
<211> LENGTH: 39
<212> TYPE: DNA
<213> ORGANISM: Ostreopsis lenticularis

<400> SEQUENCE: 214
tttttttttt ttttgtgctc attggtagca gcatgccat                             39

<210> SEQ ID NO 215
<211> LENGTH: 39
<212> TYPE: DNA
<213> ORGANISM: Ostreopsis lenticularis

<400> SEQUENCE: 215
tttttttttt ttttgactct cacattccat gctcctctg                             39

<210> SEQ ID NO 216
<211> LENGTH: 39
<212> TYPE: DNA
<213> ORGANISM: Artificial sequence
<220> FEATURE:
<223> OTHER INFORMATION: Ostreopsis sp. Cf. Ovata

<400> SEQUENCE: 216
tttttttttt ttttggcaat agcctgccaa gaacgcttt                             39

<210> SEQ ID NO 217
<211> LENGTH: 39
<212> TYPE: DNA
<213> ORGANISM: Artificial sequence
<220> FEATURE:
<223> OTHER INFORMATION: Ostreopsis sp. Cf. Ovata

<400> SEQUENCE: 217
tttttttttt ttttcgggta ggtctggtcc tggtaattt                             39

<210> SEQ ID NO 218
<211> LENGTH: 39
<212> TYPE: DNA
<213> ORGANISM: Artificial sequence
<220> FEATURE:
<223> OTHER INFORMATION: Ostreopsis sp. Cf. Ovata

<400> SEQUENCE: 218
tttttttttt ttttgcagtt tccaggttgc cacaccatt                             39

<210> SEQ ID NO 219
<211> LENGTH: 39
<212> TYPE: DNA
<213> ORGANISM: Artificial sequence
<220> FEATURE:
<223> OTHER INFORMATION: Ostreopsis sp. 24

<400> SEQUENCE: 219
tttttttttt ttttattggt gggagatgca ccagtgtgt                             39

<210> SEQ ID NO 220
<211> LENGTH: 39
<212> TYPE: DNA
<213> ORGANISM: Artificial sequence
<220> FEATURE:
<223> OTHER INFORMATION: Ostreopsis sp. 24
```

```
<400> SEQUENCE: 220
tttttttttt ttttaacatt ggtgggagat gcaccagtg                              39

<210> SEQ ID NO 221
<211> LENGTH: 39
<212> TYPE: DNA
<213> ORGANISM: Artificial sequence
<220> FEATURE:
<223> OTHER INFORMATION: Ostreopsis sp. 24

<400> SEQUENCE: 221
tttttttttt ttttagcatg agtctgccac acagaagtg                              39

<210> SEQ ID NO 222
<211> LENGTH: 39
<212> TYPE: DNA
<213> ORGANISM: Artificial sequence
<220> FEATURE:
<223> OTHER INFORMATION: Ostreopsis sp. Middle clade in Ost. Ovata

<400> SEQUENCE: 222
tttttttttt ttttgcaagt gcaaggacaa gcttcacag                              39

<210> SEQ ID NO 223
<211> LENGTH: 39
<212> TYPE: DNA
<213> ORGANISM: Artificial sequence
<220> FEATURE:
<223> OTHER INFORMATION: Ostreopsis sp. Middle clade in Ost. Ovata

<400> SEQUENCE: 223
tttttttttt ttttctccca acctgacgca gtattccac                              39

<210> SEQ ID NO 224
<211> LENGTH: 39
<212> TYPE: DNA
<213> ORGANISM: Artificial sequence
<220> FEATURE:
<223> OTHER INFORMATION: Ostreopsis sp. Middle clade in Ost. Ovata

<400> SEQUENCE: 224
tttttttttt ttttcggatt cccctttgc gcttcagtt                               39

<210> SEQ ID NO 225
<211> LENGTH: 39
<212> TYPE: DNA
<213> ORGANISM: Artificial sequence
<220> FEATURE:
<223> OTHER INFORMATION: Ostreopsis sp. Middle clade in Ost. Ovata
      competitor

<400> SEQUENCE: 225
tttttttttt ttttcggatt cccctttgc gcttcagtt                               39

<210> SEQ ID NO 226
<211> LENGTH: 39
<212> TYPE: DNA
<213> ORGANISM: Artificial sequence
<220> FEATURE:
<223> OTHER INFORMATION: Ostreopsis sp. Middle bottom clade

<400> SEQUENCE: 226
tttttttttt tttttaacgg tgttttccac acagatgaa                              39

<210> SEQ ID NO 227
```

<210> SEQ ID NO 227
<211> LENGTH: 39
<212> TYPE: DNA
<213> ORGANISM: Artificial sequence
<220> FEATURE:
<223> OTHER INFORMATION: Ostreopsis sp. Middle bottom clade

<400> SEQUENCE: 227
tttttttttt ttttaacaac tgttgttgtg caggcccga                              39

<210> SEQ ID NO 228
<211> LENGTH: 39
<212> TYPE: DNA
<213> ORGANISM: Artificial sequence
<220> FEATURE:
<223> OTHER INFORMATION: Ostrepsis sp. Missing middle clade

<400> SEQUENCE: 228
tttttttttt ttttaagttg ccacagcaag caccagcat                              39

<210> SEQ ID NO 229
<211> LENGTH: 39
<212> TYPE: DNA
<213> ORGANISM: Artificial sequence
<220> FEATURE:
<223> OTHER INFORMATION: Ostrepsis sp. Missing middle clade

<400> SEQUENCE: 229
tttttttttt ttttcccgct gatcaaccca agcccgttc                              39

<210> SEQ ID NO 230
<211> LENGTH: 39
<212> TYPE: DNA
<213> ORGANISM: Artificial sequence
<220> FEATURE:
<223> OTHER INFORMATION: Ostrepsis sp. Missing middle clade

<400> SEQUENCE: 230
tttttttttt ttttccccgc tgatcaaccc aagcccgtt                              39

<210> SEQ ID NO 231
<211> LENGTH: 39
<212> TYPE: DNA
<213> ORGANISM: Artificial sequence
<220> FEATURE:
<223> OTHER INFORMATION: ostreopsis sp. Subset of top & bottom clade,
      top only

<400> SEQUENCE: 231
tttttttttt ttttgccaca gcaaacacta gcatcacag                              39

<210> SEQ ID NO 232
<211> LENGTH: 39
<212> TYPE: DNA
<213> ORGANISM: Artificial sequence
<220> FEATURE:
<223> OTHER INFORMATION: Ostreopsis sp. Middle lower clade

<400> SEQUENCE: 232
tttttttttt ttttgcactc tttgctatgc aagagagcc                              39

<210> SEQ ID NO 233
<211> LENGTH: 39
<212> TYPE: DNA
<213> ORGANISM: Artificial sequence
<220> FEATURE:
<223> OTHER INFORMATION: Ostreopsis sp. lower clade

<400> SEQUENCE: 233
tttttttttt ttttgcccaa caactgttac tctgcagtc                                  39

<210> SEQ ID NO 234
<211> LENGTH: 39
<212> TYPE: DNA
<213> ORGANISM: Coolia monotis

<400> SEQUENCE: 234
tttttttttt ttttcgccac ggtatgccaa gaccatacc                                  39

<210> SEQ ID NO 235
<211> LENGTH: 39
<212> TYPE: DNA
<213> ORGANISM: Coolia monotis

<400> SEQUENCE: 235
tttttttttt tttttcaccc gtcaacgcca cggtatgcc                                  39

<210> SEQ ID NO 236
<211> LENGTH: 39
<212> TYPE: DNA
<213> ORGANISM: Coolia monotis

<400> SEQUENCE: 236
tttttttttt ttttggtcca gcataaagct ggtgatggt                                  39

<210> SEQ ID NO 237
<211> LENGTH: 41
<212> TYPE: DNA
<213> ORGANISM: Artificial sequence
<220> FEATURE:
<223> OTHER INFORMATION: Coolia monotis clade 3 sequences

<400> SEQUENCE: 237
tttttttttt ttttcaaaac atacacatga cacatgggat t                               41

<210> SEQ ID NO 238
<211> LENGTH: 39
<212> TYPE: DNA
<213> ORGANISM: Artificial sequence
<220> FEATURE:
<223> OTHER INFORMATION: Gonyaulaux spinfera 2 spp

<400> SEQUENCE: 238
tttttttttt ttttcactca cagtaggttc agggcctttt                                 39

<210> SEQ ID NO 239
<211> LENGTH: 39
<212> TYPE: DNA
<213> ORGANISM: Artificial sequence
<220> FEATURE:
<223> OTHER INFORMATION: Gonyaulaux spinfera 2 spp

<400> SEQUENCE: 239
tttttttttt ttttaccata tccccccaaa agcatgcag                                  39

<210> SEQ ID NO 240
<211> LENGTH: 39
<212> TYPE: DNA
<213> ORGANISM: Artificial sequence
<220> FEATURE:
<223> OTHER INFORMATION: Gonyaulaux spinfera 2 spp

<400> SEQUENCE: 240 ttttttttttt tttttgcaaa ggcacgccat cagcaaact                              39

<210> SEQ ID NO 241
<211> LENGTH: 39
<212> TYPE: DNA
<213> ORGANISM: Artificial sequence
<220> FEATURE:
<223> OTHER INFORMATION: Gonyaulaux spinfera 2 spp + baltica

<400> SEQUENCE: 241
tttttttttt tttttcccaa gaagcacgac tcagaggtg                              39

<210> SEQ ID NO 242
<211> LENGTH: 39
<212> TYPE: DNA
<213> ORGANISM: Artificial sequence
<220> FEATURE:
<223> OTHER INFORMATION: Gonyaulaux spinfera 2 spp + baltica third spp

<400> SEQUENCE: 242
tttttttttt tttttcccaa gaagcacgac tcaggggtg                              39

<210> SEQ ID NO 243
<211> LENGTH: 42
<212> TYPE: DNA
<213> ORGANISM: Artificial sequence
<220> FEATURE:
<223> OTHER INFORMATION: Gonyaulaux spinifera 3 spp

<400> SEQUENCE: 243
tttttttttt ttttattcca atcacaagac acagatgccc ca                          42

<210> SEQ ID NO 244
<211> LENGTH: 39
<212> TYPE: DNA
<213> ORGANISM: Artificial sequence
<220> FEATURE:
<223> OTHER INFORMATION: Gonyaulaux spinifera 3 spp

<400> SEQUENCE: 244
tttttttttt ttttaggtac acacccaatg ggcagacca                              39

<210> SEQ ID NO 245
<211> LENGTH: 39
<212> TYPE: DNA
<213> ORGANISM: Artificial sequence
<220> FEATURE:
<223> OTHER INFORMATION: Gonyaulaux spinifera 3 spp

<400> SEQUENCE: 245
tttttttttt ttttgaacct ggcaatgcca ggaatggtt                              39

<210> SEQ ID NO 246
<211> LENGTH: 39
<212> TYPE: DNA
<213> ORGANISM: Artificial sequence
<220> FEATURE:
<223> OTHER INFORMATION: Gonyaulaux spinifera 4 spp

<400> SEQUENCE: 246
tttttttttt ttttagttct ggcagggcca gcattgatt                              39

<210> SEQ ID NO 247
<211> LENGTH: 39
<212> TYPE: DNA

```
<213> ORGANISM: Lingulodinium polyhedrum

<400> SEQUENCE: 247
tttttttttt ttttggcaaa caggactgtc accctcatt                              39

<210> SEQ ID NO 248
<211> LENGTH: 39
<212> TYPE: DNA
<213> ORGANISM: Lingulodinium polyhedrum

<400> SEQUENCE: 248
tttttttttt ttttggactg tcaccctcat tagtgctct                              39

<210> SEQ ID NO 249
<211> LENGTH: 39
<212> TYPE: DNA
<213> ORGANISM: Lingulodinium polyhedrum

<400> SEQUENCE: 249
tttttttttt ttttctgcac ccccattggc aacgcatct                              39

<210> SEQ ID NO 250
<211> LENGTH: 44
<212> TYPE: DNA
<213> ORGANISM: Protoceratium reticulatum

<400> SEQUENCE: 250
tttttttttt ttttctcacc ctcgttgatg cttttttccca aaag                       44

<210> SEQ ID NO 251
<211> LENGTH: 39
<212> TYPE: DNA
<213> ORGANISM: Protoceratium reticulatum

<400> SEQUENCE: 251
tttttttttt ttttatacac ccgcttcctc ttcagcaat                              39

<210> SEQ ID NO 252
<211> LENGTH: 42
<212> TYPE: DNA
<213> ORGANISM: Protoceratium reticulatum

<400> SEQUENCE: 252
tttttttttt ttttcatctt caaactacaa ttcaaggcca ga                          42
```

MICROARRAY SLIDE FOR DETECTING TOXIC ALGAE, BARCODES OF DNA, HYBRIDISATION SOLUTION AND METHOD OF DETECTING TOXIC ALGAE

REFERENCE TO AN ELECTRONIC SEQUENCE LISTING

The contents of the electronic sequence listing (RJ6766.txt; Size: 47.4 KB; and Date of Creation: Apr. 11, 2016) is herein incorporated by reference in its entirety and contains no new subject matter.

BACKGROUND

The present invention relates to a microarray slide for detecting, identifying and quantifying toxic algae. More specifically, the microarray, which comprises DNA barcodes for each toxic alga, is configured to detect and quantify an assemblage of toxic algae from marine environmental samples to a high confidence level to meet EU Directive 2002/225/EC for the quantification of toxic algae in marine coastal waters as a means of determining fishery closure. It provides an alternative to the mouse bioassay for fishery closure, which has been banned by the EU for ethical reasons since 2012. The need for invoking the more expensive HPLC method for toxin determination can be reduced with a reliable molecular method that can identify and quantify toxic algae.

The world's oceans cover 70 percent of the Earth's surface, and their dominant populations, both numerically and biomass-wise, belong to microscopic protests (including microalgae) and prokaryotes. Microalgae in marine and brackish waters of Europe regularly cause harmful effects, considered from the human perspective, in that they cause economic damage to fisheries and tourism and health issues. These episodes encompass a broad range of phenomena collectively referred to as <((harmful algal blooms)) (HABs) or red tides. For adequate management of these phenomena, monitoring of microalgae is essential and is required by EU directive 2002/225/EC for all European countries with a marine coastline.

The global scale of toxin producing micro-algae should not be underestimated. For example, the most serious would be the numbers of human intoxications with ciguatera, caused by the dinoflagellate *Gambierdiscus*, is currently estimated at some 50,000 per year. Every year, 1-2 human deaths are linked to the ingestion of PSP toxins caused by *Alexandrium*. Although these problems are restricted to the tropical/warm temperate sphere of the globe, it demonstrates the urgent need to be able to monitor and prevent toxic HAB events. With global warming warm water species are now moving into north temperate European waters. In Europe, this is affected through a series of directives that require coastal member states to monitor water for toxin producing species and their toxins in shellfish. Starting with the EU Shellfish Hygiene Directive 91/492/EEC, a series of Directives was issued to include newly discovered toxins, and stipulating the methods of analysis and maximum permitted levels in shellfish. The most important of these are 2002/225/EC and 2074/2005 (pertaining to toxin levels and analysis and methods) and more recently 15/2011 (analysis methods).

The natural occurrence of toxin producing algae, and the continual human demand for shellfish consumption, means that the need for their monitoring is here to stay.

The cost of this monitoring of plankton and toxins is enormous. Although there is limited 'hard' information on the economic impact of HABs, a relatively recent study in the US (Anderson et al., 2000) has estimated, on a national basis, that:
  the cost of monitoring is equivalent to 5% annual shellfish industry turnover
  the cost of lost harvest and damaged product caused by contamination with biotoxins is 5% of industry turnover
  the public health costs caused by lost working days, hospitalisations etc. add another 5% of annual turnover In Europe, similar information is also difficult to uncover, but the context is well set if one takes the case of Ireland where the shellfish aquaculture production currently runs at €47 million annually (Bowne et al., 2007) and the budget for the Irish National Biotoxin and Toxic Phytoplankton monitoring programme, carried out under the auspices of the Food Safety Authority of Ireland, and operated through the Irish Marine Institute, is €1.7 million, representing ~3.5% of annual industry turnover. Similarly, Scottish shellfish production is valued at ~£20 million, the most part of which is through culture of the edible mussel *Mytilus edulis*, and the monitoring programmes, run by the Food Standards Agency Scotland, has a budget of just under £2 million.

Clearly the development of an industry that is both natural and sustainable, but which has such a heavy financial burden, requires all possible assistance in order to overcome such 'natural hazards' as toxic HABs, because the (natural) problems caused by toxicity will never go away. Approximately 2000 water samples are analysed annually in Ireland as part of the National Monitoring Programme (NMP). This requires a staff of 4 people, augmented slightly during the busy summer months. Most samples are scanned for toxic/harmful species but samples from 10 sites (out of a total of ~60) are analysed for their total phytoplankton community. Light microscopy is the routine analysis method, each sample requiring ca. 2 hours on average to examine. Comparable figures for other monitoring programmes are annual throughputs of 1000 samples (Scotland), 5000 samples (REPHY, France), and 6000 samples (Galicia, Spain). These figures reflect a work rate of processing some 20 samples per week per person. The number of man-hours involved in the monitoring process is clearly enormous. Often the results are available up to 5 days after taking the sample making mitigation strategies almost impossible. This invention seeks, inter alia, to provide a solution to this problem.

Present day monitoring is time consuming and based on morphology as determined by light microscopy is insufficient to give definitive species and toxin attribution. Molecular techniques, which are faster and more reliable, would reduce the number of inevitable mistakes caused by human error that is an ever-present facet of this type of work. Of particular relevance are the situations with respect to *Pseudo-nitzschia*, which cannot be identified to species level using light microscopy, and *Alexandrium*, another genus with which it is also virtually impossible to identify accurately to species using this technique. Identification and quantification to a level of accuracy is essential if toxic blooms are to be accurately forecast to allow their mitigation and fishery closure enforced only when needed to avoid unnecessary economic loss and because toxic and non-toxic strains of the same species, i.e., *Alexandrium*, overlap in their distribution.

The advent of molecular biological techniques has greatly enhanced our ability to analyse all organisms. These techniques are slowing making inroads into monitoring for toxic algae in terms of monitoring for the presence of a species and the toxins they produce. One approach that is extensively used in such studies is to identify species by specific molecular probes or barcodes. In hybridisation experiments, these probes can therefore be used to identify species of interest by binding to the target's sequence and later detection by a probe-attached label. Calibration curves based on culture material can be generated to convert the probe signal intensity from its label to cell numbers, thus meeting EU requirements for toxic algal monitoring using cell numbers as the trigger level for fisheries closure or before initiating tests for toxins. The microarray presented here can be universally applied to monitor for toxic algae in any country with toxic algal blooms. In Japanese waters, the toxic algae causing the most problems will not the same as those along the western and eastern coasts of Australia and North America, or along the western coasts of Europe, thus it is advantageous to have universal barcodes that specifically detect all variations of each toxic algal species.

SUMMARY

According to a first aspect of the invention there is provided an array system comprising a microarray slide configured to simultaneously detect a plurality of organisms in a sample, wherein the microarray slide comprises nucleic acid probes having fragments of 18S or 28S RNA sequence unique to each organism or taxonomical group thereof.

According to a second aspect of the invention there is provided a method of detecting toxic algae in a sample comprising the steps of:
a) obtaining an environmental sample
b) extracting the RNA from algae cells present in the sample
c) fragmenting the RNA
d) labelling the RNA fragments with a fluorescent label
e) allowing the labelled RNA fragments to hybridise onto a microarray slide according to the first aspect of the invention
f) washing off un-hybridised labelled RNA fragments
g) scanning the microarray slide to detect labelled RNA fragments bound to the probe.

According to a third aspect of the invention there is provided a method of fabricating a microarray slide, comprising the steps of identifying 18S or 28S RNA sequences corresponding to a plurality of toxic algae of interest; selecting fragments of 18S or 28S RNA sequence unique to each algae and creating nucleic acid probes corresponding to said sequences; creating variant RNA fragments corresponding to the fragments of 18S or 28S RNA unique to each non-target with a one nucleotide mismatch in order to capture a one nucleotide mismatch; creating probes having said sequences; and immobilising said probes onto a microarray slide.

BRIEF DESCRIPTION OF THE DRAWINGS

FIG. 1. Spotting scheme for the first generation MIDTAL microarray. Each position in the grid represents a spot of c. 50 µm in diameter where a given probe (barcode) is immobilised. Each probe (barcodes) is spotted four times in one grid and the entire grid is repeated 3 times to give a pseudo replication of n=16. This generation of the microarray has 960 spots, covering 112 probes (barcodes) for toxic algal species and higher taxon levels, and various positive and negative control probes. Later generations of the microarray, which form the invention described here, have 252 probes (barcodes), when spotted with 4 replicates will produce an array of over 1000 spots.

FIG. 6 illustrates the output from the GPR analyser program (Dittami and Edvardsen 2012) showing the hierarchy tests for one hybridisation. *Pseudo-nitzschia calliantha* passed the hierarchy test and the signal was converted to cell numbers for monitoring purposes.

DEFINITIONS

Figure 2:
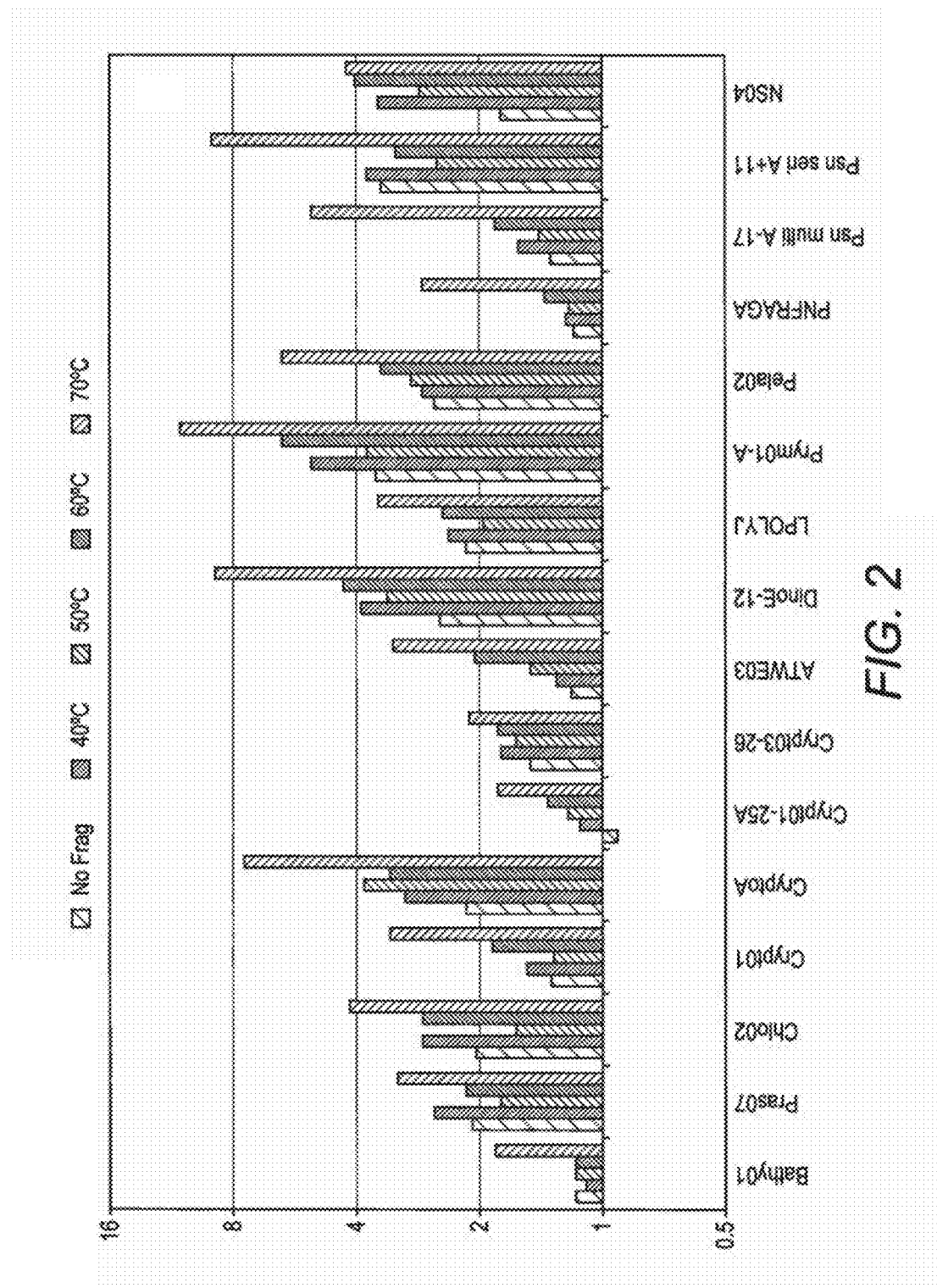
FIG. 2 is the hybridization of fragmented RNA in increasing incubation temperature to microarray. Probes (barcodes) with lower signals are enhanced by fragmentation of the RNA into smaller pieces to allow better binding of the barcode to its target sequence.

In describing the disclosed subject matter, the following terminology will be used in accordance with the definitions set forth below.

Algae refer to any photosynthetic cell without tissue differentiation into roots, stems and leaves. Toxic algae refers to microalgae belonging to either the dinoflagellates, diatoms, haptophyte, dictyophyte, chloromonophyte, or raphidophyte algal classes that produce toxin compounds that affect vertebrates, including humans, either causing death or serious gastrointestinal or neurological effects.

DNA and RNA refer to nucleic acids (2 base-sugar-phosphate combinations or more=oligonucleotides). The RNAs referred to here are ribosomal RNA, the small and the large subunits of eukaryotic organisms (SSU/18S or LSU/28S) and specifically excludes those of prokaryotic organisms (bacteria and archea). Arrays made for the detection of prokaryotic organisms can only measure actively growing bacteria and archea but this is not the case with eukaryotic organisms that retain a high proportion of rRNA throughout their growth cycle and thus arrays for eukaryotic organisms can be quantitative, whereas those for prokaryotic organisms cannot. Probes or barcodes are short oligonucleotides of normally 16-25 bp length that are 100% homologous only to a complementary sequence in a gene of the species of interest and differ by at least one position to all other organisms. A DNA microarray for species detection (also commonly known as a phylochip) and not for gene expression is a collection of microscopic DNA spots attached to a solid surface, such as glass, plastic or silicon chip forming an array. The affixed DNA oligonucleotides are known as probes or barcodes (although some sources will use different nomenclature), thousands of which can be used in a single DNA microarray. The barcodes are immobilised by chemical bonding of the probe to the surface of a specially coated microscope glass slide and in the present invention the barcodes are lifted above the surface of the microarray by a spacer region consisting of multiple thymine bases before the barcode begins. Hybridisation refers to the binding of the single-stranded barcode immobilised on the microarray to single stranded, fluorescently labelled rRNA extracted from the environmental sample to form a double helix along the short stretch of the target region of the rRNA. High salt and specific buffer concentrations provide a suitable chemical environment for the hybridisation to occur only between target and the barcode attached to the glass microarray and to prevent non-target with one or more mismatches to the barcode from binding. If there is a single base mismatch between target and non-target, the mismatch is placed in the middle of the barcode and a competitor barcode is designed to hybridise to rRNA with the single base mismatch. These can also be called mismatch probes (MM). Hierarchical probes refer to a suite of probes that follow the taxonomic hierarchy of a given species. The use of hierarchical probes prevents false positives in environmental samples because for a toxic species to be present, the genus, family, order or clade, class, phylum and kingdom probe must also hybridise to the species' RNA. If the entire hierarchy is not present, then the analysis package used to analyse the microarray (for example, GPR analyser, Simon and Edvardsen 2012) will reject the presence of any toxic algal species that does not pass the hierarchy test. GC content refers to the amount of guanine and cytosine ribonucleotide bases are in the barcode, a 50% GC content or more ensure a melting temperature of about 60° C. at which the barcode will not be able to bind to the target because of thermal hindrance.

DETAILED DESCRIPTION

A first aspect of the invention provides an array system comprising a microarray slide configured to simultaneously detect a plurality of organisms in a sample, wherein the microarray slide comprises nucleic acid probes having fragments of 18S or 28S RNA sequence unique to each organism or taxonomical group thereof.

Preferably the plurality of organisms comprise toxic algae organisms.

Microarray Slide

Any suitable microarray slide format may be used in conjunction with any aspect of the invention. For example, the probes may be spotted onto epoxy-coated Genetix or Schott slides using a pin printer VersArray ChipWriter Pro (Bio-Rad Laboratories GmbH, Munich, Germany) and split pins (Point Technologies, Inc., CO) with a spot size of ca. 80 µm.

Nucleic Acid Probes

Oligonucleotides probes including the positive and negative controls may be synthesized by using standard chemical techniques. They are preferably synthesised such that they are able to bind covalently at the 5' end to the microarray slide. For example, they may be synthesised with a MMT or DMS(O)MT amino-link (preferably a 6C amino link). The amino link enables the probe to bond covalently to the coated glass slide at 5' end.

According to certain preferred embodiments the microarray slide comprises:
a. at least one probe selected from the group consisting of positive and negative controls,
b. at least one probe capable of selectively detecting at eukaryotic organisms
c. at least one probe capable of selectively detecting the taxonomic phylum of the organism
d. at least one probe capable of selectively detecting the taxonomical class of the organism
e. at least one probe capable of selectively detecting a taxonomical clade of the organism at a taxonomical level intermediate between class and genus
f. at least one probe capable of selectively detecting the taxonomical genus of the organism, and
g. at least one probe capable of selectively detecting the taxonomical species of the organism.
h. at least one probe capable of selectively detecting the taxonomical strain of the organism.

The probes listed at point h. above apply especially to the detection of strains of organisms which have both a toxic and non-toxic strain.

The use of probes that are specific for multiple taxonomical levels allows all aspects of the invention to be arranged so that a positive identification of a specific algae species, or where applicable a positive identification of a specific algae strain is only achieved when the species specific probe, or where appropriate the strain specific probe, is bound by the target sequence together with binding of probes representing all higher-order taxons.

Positive and Negative Controls

Optionally positive controls are included and comprise TATA box sequence for example the sequence of SEQ ID NO: 1. Other controls, which may optionally be present include negative controls (for example those having the sequences of SEQ ID NOs: 2, 3 or 4).

Poly-T spotting controls (for example that having the sequence of SEQ ID NO: 5, poly-A blocking probes and internal controls (for example one or both of the *Dunadiella* genus internal controls having the sequences of SEQ ID NO: 7 and 8) may also be included.

Probe Characteristics

Preferably the probes are all of similar length, for example from 20 to 30 residues in length. More preferably they are all from 22 to 28, 23 to 27 or 24 to 26 residues in length (i.e. about 25 residues in length). Preferably the probes all have an approximately equal G/C content. Preferably the G/C content is from 40 to 60, more preferably 41 to 59, 42 to 58, 43 to 57, 44 to 56, 45 to 55, 46 to 54, 47 to 53, 48 to 52 or 49 to 51 percent. Providing probes of similar length and similar G/C content results in all probes having a similar hybridization temperature.

Poly-T-Tails

Preferably the probes have a poly-T tail 5' before the barcode sequence and after a six carbon linker. This tail is preferably at least 10 or more preferably at least 15 residues long (for example between 10 and 25 or between 15 and 30 residues or 15 and 20 residues long). It is hypothesised that the provision of this tail permits better access of the probes to the target RNA because they are able to "float" above the surface of the micro array slide and interact with the targets. If probes having poly-T tails are used, poly-A oligonucleotides must be added in to the hybridisation solution to bind to the poly-T tails and prevent the binding of false positives to the tail.

The invention also encompasses in all of its aspects any or all of the probes disclosed herein wherein the poly-T tail is replaced by an alternative linker or spacer element that performs essentially the same function as the poly-T tail.

Competitor Probes

Competitor probes with the single base mismatch to each of the specific probes included in the microarray are preferably included in the array to take out these non-targets and prevent them from binding to any barcode to which they have a single base mismatch.

Both of these optimisations produce superior and enhanced signals relative to those produced by the ALEX-chip in Gescher et al. (2008) who do not include these optimisations. (Gescher, G., Mettfies K. and Medlin, L. K. 2008. The ALEX Chip—Development of a DNA chip for identification and monitoring of *Alexandrium*. Harmful Algae, 7: 485-494).

Sample Preparation

Preferably the sample is an environmental sample, for example a sample of seawater or estuarine water.

The sample may optionally be prepared before being used. For example any organisms in it may be concentrated (for example by filtration) to increase their density and cells may be lysed, RNA extracted and prepared, for example by fragmentation into fragments of approximately 500 bp in length.

Universal Array

The invention presented here in all aspects is preferably a universal microarray for the detection of toxic algae. It is universal in the sense that it can be used to detect all known marine toxic algae presently known to occur in all oceans and estuaries and high conductivity continental lakes on Earth. It is universal in that it can detect 1) all species causing paralytic shellfish poisoning (PSP), e.g. species in the genus *Alexandrium, Gymnodinium catenatum*, and *Pyrodinium bahamense*, 2) all species causing amnesic shellfish poisoning (ASP), e.g. species in the genus *Pseudo-nitzschia*, 3) all species causing diarrheic shellfish poisoning (DSP), e.g. species in the genera *Prorocentrum, Dinophysis*, and *Volcanodinium*, 4) all species causing ciguatera poisoning (permanent reversal of hot and cold sensations), e.g. *Gambierdiscus, Coolia, Prorocentrum, Ostreopsis*, 5) all species causing Neurotoxic Shellfish Poisoning (NSP), e.g. species in the genera *Karenia, Karolodinium, Chloromorum* and 6) all species causing fish kills through lysis of the gill membranes, e.g. *Heterosigma, Chatonella, Pseudochatonella, Fibrocapsa, Lingulodinium* and *Gonyaulax spinifera*. It is universal in that all barcodes/probes for each toxic species, group of species, or higher taxonomic hierarchy have been designed to work under identical laboratory conditions. Excellent synopses of the state of the art of molecular tools in environmental studies to detect toxic algae can be found in:

Ebenezer, V., Medlin, L. K. and Kei, J-S. 2011. Molecular detection, quantification, and diversity evaluation of microalgae. Marine Biotechnology, 14:129-142, and Metfies, K., Töbe, K., Scholin, C. and Medlin, L. K. 2006. Novel Approaches to Study the Ecology of HA in situ chapter. In: Ecology of Harmful Algae. Edna Grandéli and Jefferson Turner (eds.) pp. 311-325.

According to certain preferred embodiments, the microarray consists of spots of artificially synthesised DNA regularly spotted onto a specially coated glass slide with at least 4 to 8 replicates (FIG. 1). The DNAs spotted are short oligonucleotides of at least 25 bases with a poly T tail of at least 15 thymine bases. These oligonucleotides are specific for or one of more species of toxic algae (see Table 1) and as such can be considered barcodes. Barcodes have been designed in a taxonomic hierarchical fashion such that for any species to be present, the barcodes for the genus, family or order, class, phylum and kingdom must also be present. This method ensures that no false positives are recorded. No other microarray in use for toxic algae or other eukaryotes using this method of internal control.

Preferably the following features apply:

a. the probes in group a. comprise at least one probe having a sequence selected from SEQ ID NO: 1 to SEQ ID NO: 4, SEQ ID NO:7 and SEQ ID NO:8, and b. the probes in group b. comprise at least both of the probes having sequences respectively given in SEQ ID NO:9 to SEQ ID NO: 10; and c. the probes in group c. comprise at least all of the probes having sequences respectively given in SEQ ID NO: 11 to SEQ ID NO: 13; and d. the probes in group d. comprise at least all of the probes having sequences respectively given in SEQ ID NO: 14 to SEQ ID NO: 16; and e. the probes in group e. comprise at least all of the probes having sequences respectively given in SEQ ID NO: 17 to SEQ ID NO: 41; and f. the probes in group f. comprise at least all of the probes having sequences respectively given in SEQ ID NO: 42 to SEQ ID NO: 69; and g. the probes in group g. and h. comprise at least all of the probes having sequences respectively given in SEQ ID NO: 70 to SEQ ID NO: 252.

Further Features

According to a first aspect of the invention, the microarray slide comprises fragments of 18S or 28S RNA unique to each organism and mismatch variants (for example single nucleotide mismatch variants) of said fragments wherein the level of confidence of specific detection derived from fragment matches is higher than 99%.

According to all aspects of the invention, the identification and quantification of a toxic algae species or strain is based on detected hybridization of the species-specific and/or the strain-specific probe and hybridisation of all higher taxon level probes. This hierarchical system permits greater confidence in results and also provides a useful indication of the presence of both known and unknown species for which a species specific probe is not includes in the array.

According to a second aspect the invention provides a method of detecting toxic algae in a sample comprising the steps of:

a) obtaining an environmental sample
b) extracting the RNA from algae cells present in the sample
c) fragmenting the RNA
d) labelling the RNA fragments with a fluorescent label
e) allowing the labelled RNA fragments to hybridise onto a microarray slide according to the first aspect of the invention
f) washing off un-hybridised labelled RNA fragments
g) scanning the microarray slide to detect labelled RNA fragments bound to the probe.

The signal strength obtained from the bound fragments may be used to provide an estimate of the concentration of algal cells in the sample.

Further optional features of each step of the method may be imported from the Examples.

The invention also provides a third aspect a method of fabricating a microarray slide, comprising the steps of identifying 18S or 28S RNA sequences corresponding to a plurality of toxic algae of interest; selecting fragments of 18S or 28S RNA sequence unique to each algae and creating nucleic acid probes corresponding to said sequences; creating variant RNA fragments corresponding to the fragments of 18S or 28S RNA unique to each non-target with a one nucleotide mismatch in order to capture a one nucleotide mismatch; creating probes having said sequences; and immobilising said probes onto a microarray slide.

The extraction protocol preferably is as described in the Examples that has been optimised to use Tri-Reagent (Sigma) to obtain high quantities and good quality of RNA. The quality of the RNA affects the degree of labelling and the quality and intensity of the signal achieved after hybridisation. Most existing microarrays for toxic algae use a PCR step prior to the hybridisation to obtain a target with a short length ca 500 bp. Examples of microarrays that include a PCR step are:

Galluzi L, Cegna A, Casabianca S, Penna A., Sunder N, Magnnai, M (2011) Development of an oligonucleotide microarray for the detection and monitoring of marine dinoflagellates. J Microbiol Meth 84: 234-242 and

Ki J-S, Han M-S (2006) A low-density oligonucleotide array study for parallel detection of harmful algal species using hybridization of consensus PCR products of LSU rDNA D2 domain. *Biosensors and Bioelectronics* 21: 1812-1821.

The inclusion of a PCR step in the method prevents the signal obtained from being quantitative. Because the microarray of the invention use only RNA, it is possible to make calibration curves to convert the hybridisation signal to cell numbers. Closure of the fisheries is currently based on cell numbers exceeding a trigger level and using any microarray method that includes a PCR step precludes that method from being quantitative.

Prior to hybridisation, the RNA is preferably fragmented into lengths of ca. 500 bp (FIG. 2), similar to the lengths obtained using a PCR step but without the exponential increase in target number that is obtained with PCR, thus still maintaining the microarray quantitative. In the hybridisation solution, there is preferably added a blocking reagent, for example Kreablock (Kreatech), which is normally used in gene expression microarrays. It is found that the addition of this blocking reagent not only enhances the signal up to 10× but also reduces the background so that we have a higher signal to noise ratio.

Figure 3:
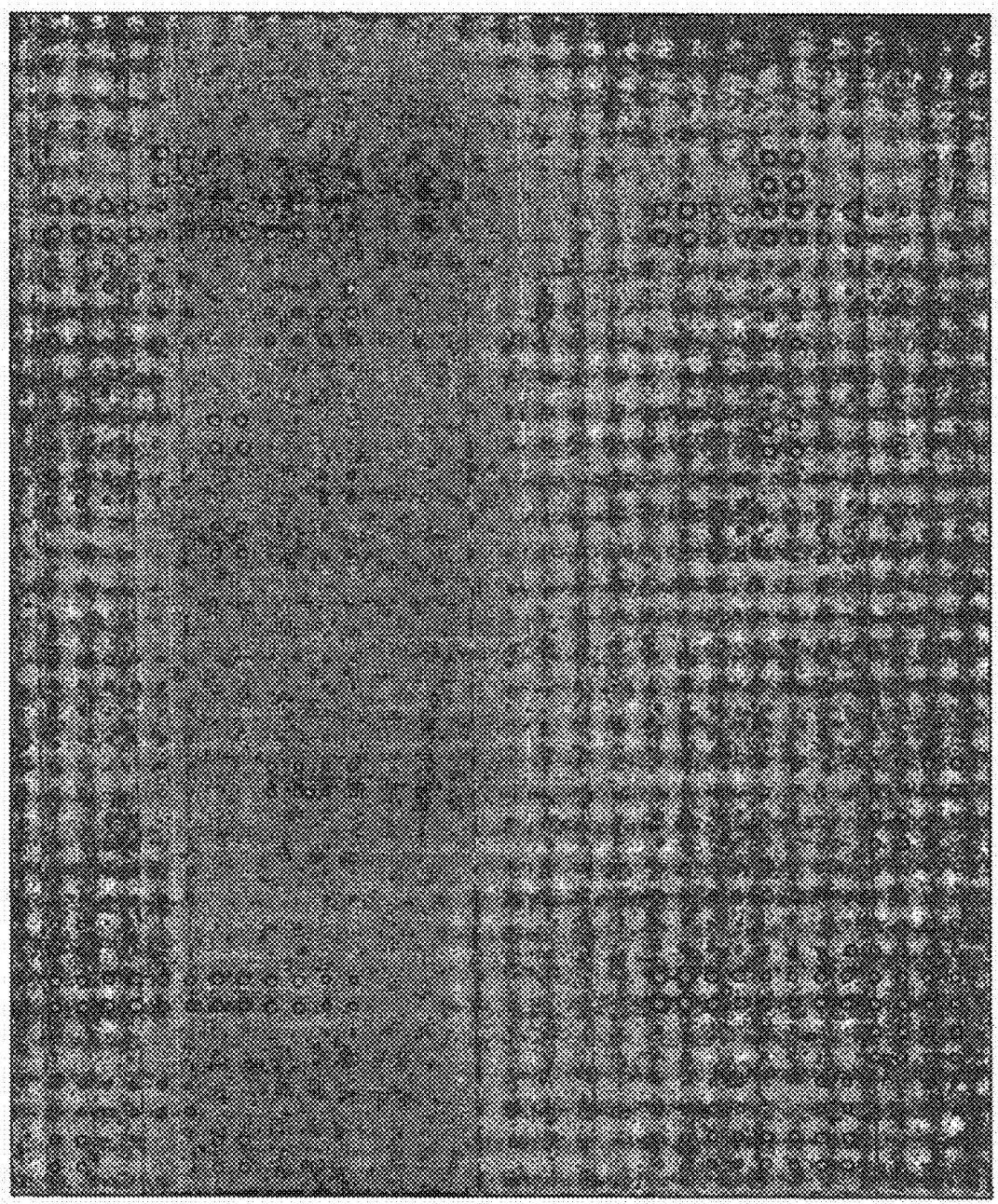
FIG. 3 is one of the super grids in the first generation MIDTAL microarray after hybridization with Cy5-labelled RNA extracted from a field sample collected in the Skagerrak coast (Gullmarnfjord, Sweden) in the beginning of August 2009.
Figure 4:
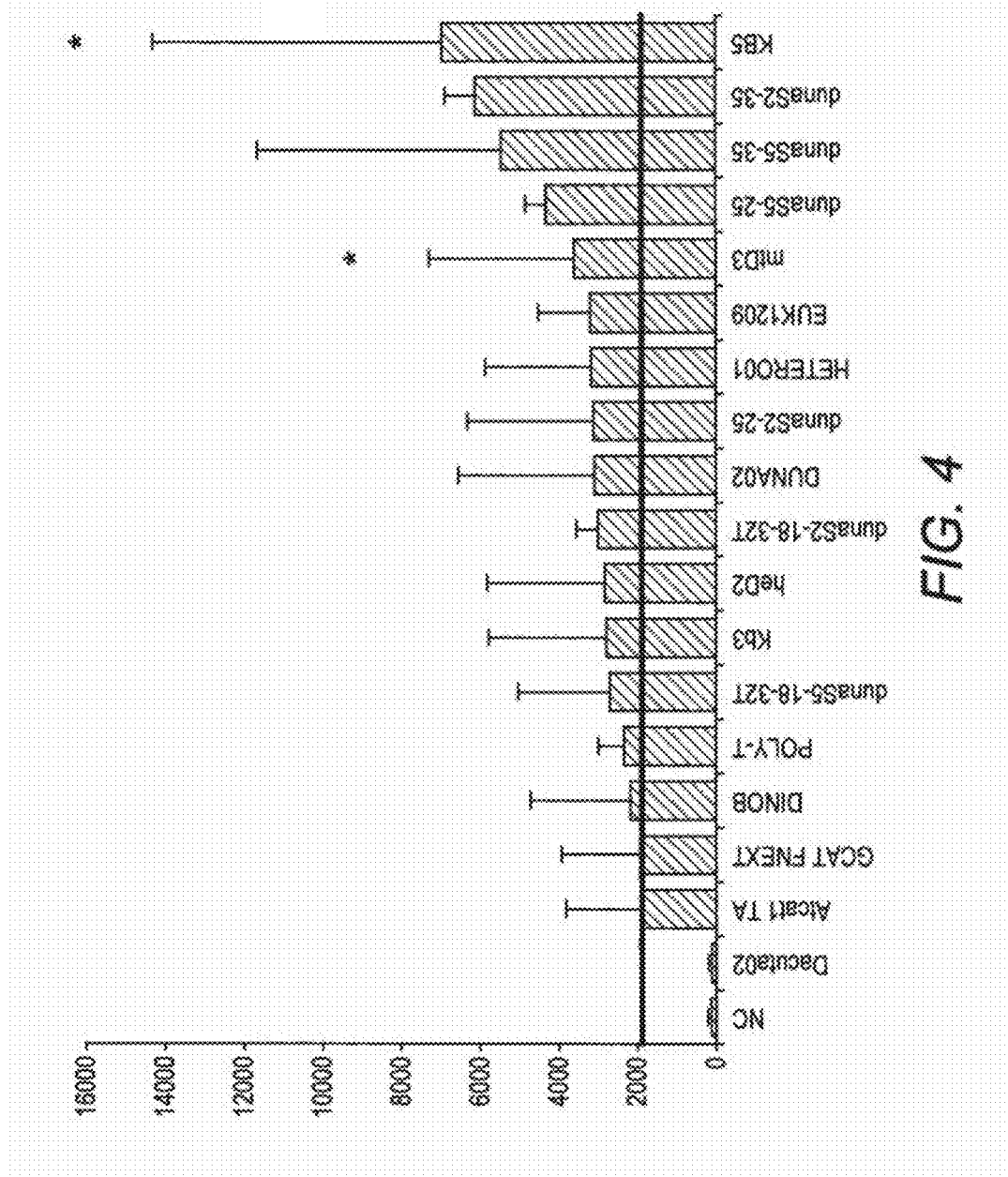
FIG. 4 provides the analysis of the hybridisation in FIG. 3 was performed with the Phylochip program, and a portion of this analysis is presented in the excel figure below the scan ranging from highest to lowest signal. Stars indicate a significant signal for the toxic species *Karenia brevis* (KB5) and *Pseudo-nitzschia multistriata* (mD3) present in the sample, seen both with the microarray and traditional counts. Other high signals are the probes for the positive control *Dunaliella*. The red line marks the threshold over which a positive signal is recorded.
Figure 5:
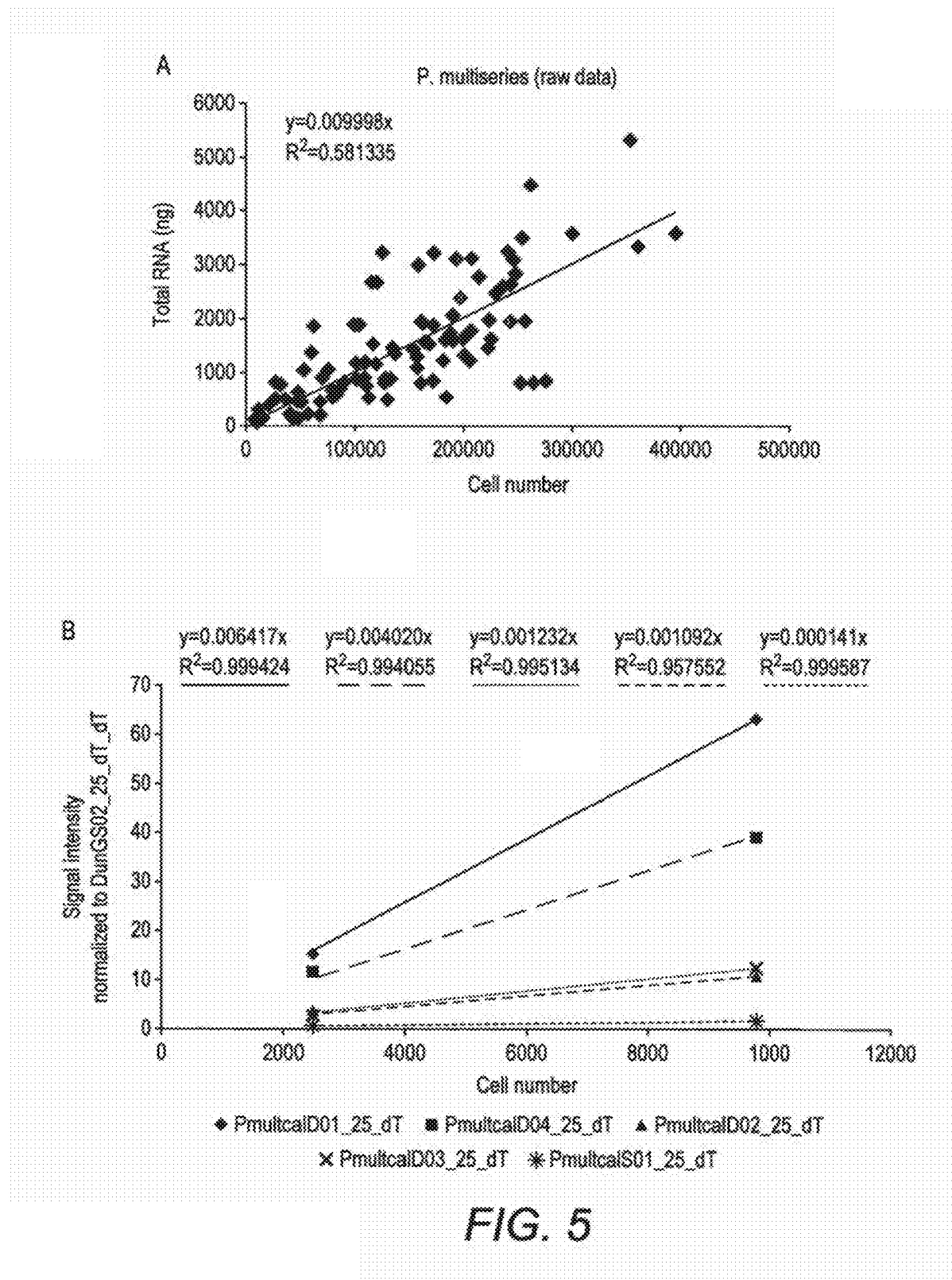
FIG. 5 shows the relationship of RNA to cell number and microarray signals for *P. multiseries*. A) Linear regression of total RNA extracted from each replicate in each stress experiment against cell numbers at the time of sampling, B) Calibration curve relating cell numbers to microarray signal hybridised with four different amounts of RNA on generation 2 array for each probe that targets *P. multiseries*, C) Calibration curve relating cell numbers to microarray signal with two different amounts of RNA on generation 3 array for each probe that targets *P. multiseries*.
Figure 5:
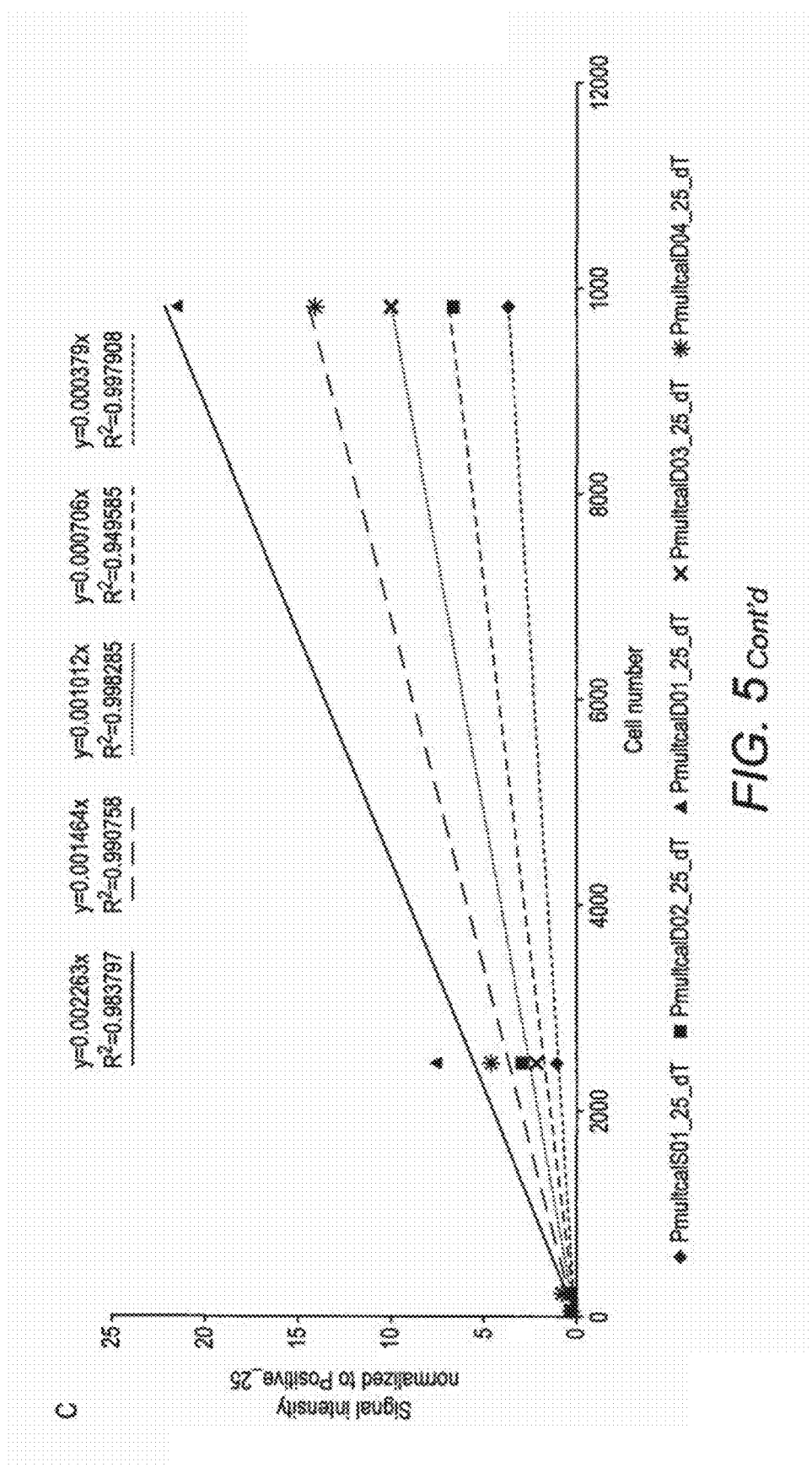

The signal obtained from our microarray is preferably a fluorescent one (FIG. 3) that is detected with a laser scanner and can be converted to cell numbers by use of calibration curves to relate signal to cell numbers (FIGS. 4 & 5). Monitoring for toxic algae and subsequent fisheries closure is based on cell numbers.

The inventors are aware of one microarray for toxic algae using total RNA as a target (Ahn S, Kulis D, Erdne, D D, Anderson, D M, Walt, D 2010. Fibre optic microarrays for the detection and enumeration of harmful algal bloom species. Afr J Mar Sci 28: 231-235). This system involves a fiber optic instrument, which is used to bind microspheres with one attached probe. The system is very expensive and is not in standard use. This microarray also uses a sandwich hybridisation detection system, which means that for each species, two probes/barcodes must be designed. One is a capture probe/barcode and this is the one that is immobilised on the microspheres to bind to the target RNA. A second probe with a fluorescent label then attaches to the bound RNA, hence the name sandwich hybridisation. The binding of this probe creates the signals that are recorded by a CCD camera. It has only been tested with three species and to test multiple species, it must be demonstrated in silico that none of the signal probes will bind with each other removing them from the hybridisation reaction. Thus from a practical and cost standpoint, the present invention is superior.

The inventors are also aware of one patent (WO 2003/053855 A2) for the use of quantitative PCR for the detection of harmful algae in ballast water. Multiplexing probes for use in quantitative PCR is limited to about 8 probes in one mixture so this methodology for detecting toxic algae using species-specific probes is limited in its ability to detect more than 8 species at a time.

Particular advantages of the present invention arise from the following features:
- the unique assemblage of barcodes for each species (SEQ ID NOs: 9 to 252),
- the design of 243 barcodes of near identical length and G/C content with a poly T tail so that they function under identical laboratory conditions to effect the binding of target RNA and only target to the barcodes spotted on the glass slide,
- the addition of poly A and optionally Kreablock to the hybridisation solution to maximize signal strength and minimise false positive,
- the construction of a hierarchical barcode arrangement so that the presence of any toxic species is dependent on a suite of nested probes that must also produce a signal, and
- the conversion of that signal to an estimate of cell numbers for monitoring purposes.

TABLE 1

Barcodes for toxic algae listed in a hierarchical fashion and the hybridisation controls

| Seq ID No. | Targeted Species | DNA Barcode: probe sequence with poly T-spacer Probe Sequences (5'-3') |
| --- | --- | --- |
| Group A | Controls | |
| Seq ID No. 1 | TATA box protein, as positive control | TTTTTTTTTTTTTTTTTTAATTATGGCCGATGAGGAACG |
| Seq ID No. 2 | Negative | TTTTTTTTTTTTTTTTTTTCCCCCGGGTATGGCCGC |
| Seq ID No. 3 | Negative | TTTTTTTTTTTTTTAGGAAGGAAGGAAGGAAGGAAGGAA |
| Seq ID No. 4 | Negative | TTTTTTTTTTTTTTAGAGAGAGAGAGAGAGAGAGAGAGA |
| Seq ID No. 5 | Poly-T (30)-CY5, as spotting control | TTTTTTTTTTTTTTTTTTTTTTTTTTTTTTTTTTTTTTT |
| Seq ID No. 6 | Poly-A as blocking probe | AAAAAAAAAAAAAAAAAAAAAAAAAAAAAA |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 7 | *Dunaliella* genus, as internal control | TTTTTTTTTTTTTTACCAAAGGCTGACCGCTACAACCCA |
| Seq ID No. 8 | *Dunaliella* genus, as internal control | TTTTTTTTTTTTTTGATACCGATCCAAACACTTCACCA |
| Group B | Higher Group Levels | |
| Seq ID No. 9 | Eukaryotes | TTTTTTTTTTTTTTGACTACTGGCAGGATCAACCAGGT |
| Seq ID No. 10 | Eukaryotes | TTTTTTTTTTTTTTAACATCTAAGGGCATCACAGACCTG |
| Group C | Phylum Levels | |
| Seq ID No. 11 | Prymnesiophyta | TTTTTTTTTTTTTTAAACATCCCTGGCAAATGCTTTCGC |
| Seq ID No. 12 | Dinophyta (incl. Apicomplexa) | TTTTTTTTTTTTTCTGTTATTGCCTCAAACTTCCTTGC |
| Seq ID No. 13 | Dinophyta (incl. Apicomplexa) | TTTTTTTTTTTTTGTCGGAAGCTGATAGGTCAGAAACT |
| Group D | Class Levels | |
| Seq ID No. 14 | Prymnesiophyceae | TTTTTTTTTTTTTTGTGTCAGGATTCGGGCAATTTACG |
| Seq ID No. 15 | Raphidophyceae | TTTTTTTTTTTTTCGAUUCGCACAGUUACUAUGAUUCACC |
| Seq ID No. 16 | Raphidophyceae class | TTTTTTTTTTTTTGCAAGAACCGGAUUGUCACCGUCCA |
| Group E | Clade Levels | |
| Seq ID No. 17 | *Dinophysiaceae* (*Dinophysis* + *Phalacroma*) not *D. acuta* | TTTTTTTTTTTTTTAGGCCAATACCGTACCGTCGGA |
| Seq ID No. 18 | *Dinophysiaceae* (*Dinophysis* + *Phalacroma*) | TTTTTTTTTTTTTCAATACCGTACCGTCGGAAGCTGAT |
| Seq ID No. 19 | *Prorocentrum planktonic* clade | TTTTTTTTTTTTTUCAAGGCGUAAGCCUGCUUGAAAC |
| Seq ID No. 20 | *Prorocentrum benthic* clade | TTTTTTTTTTTTTGAUGCCCAGAUCAAGCCAGAUGCUC |
| Seq ID No. 21 | *Prorocentrum benthic* clade | TTTTTTTTTTTTTCAACUAUCCCCAUUGACCAUUACC |
| Seq ID No. 22 | *Prymnesium* | TTTTTTTTTTTTTGGACTTCCGCCGATCCCTAGT |
| Seq ID No. 23 | all *Dinophysis* and *Phalacroma* | TTTTTTTTTTTTTGTAGGCCAATACCGTACCGTCGGAA |
| Seq ID No. 24 | *Prymnesium* B1 clade | TTTTTTTTTTTTTTACTCAGCACGCAACCGGCAAGCCGG |
| Seq ID No. 25 | *Chattonella antiqua/marina/ovata* clade | TTTTTTTTTTTTTCCCGAGAGUUAACUCGGCAUUGGUU |
| Seq ID No. 26 | *Chattonella antiqua/marina/ovata* clade | TTTTTTTTTTTTTTAAAGAUGGGGAGAAUCGCAACCCGU |
| Seq ID No. 27 | *Chattonella antiqua/marina/ovata* clade | TTTTTTTTTTTTTUGGGGAGAAUCGCAACCCGUAAGCG |
| Seq ID No. 28 | *Gambierdiscus carrpenteri* + *caribaeus* clade | TTTTTTTTTTTTTCCUCUUUCGUCCAGAAUUGGGCAAG |
| Seq ID No. 29 | *Gambierdiscus carrpenteri* + *caribaeus* clade | TTTTTTTTTTTTTUCCAGAAUUGGGCAAGUUGCGCGCC |
| Seq ID No. 30 | *Gambierdiscus carrpenteri* + *caribaeus* clade | TTTTTTTTTTTTTGGCAGAUUGCCCAACCUCUCCAGGG |
| Seq ID No. 31 | *Gambierdiscus carolinianus* + *polynesiensis* | TTTTTTTTTTTTTTCCAGAAUUGGGCAAGUUGCGCGCC |
| Seq ID No. 32 | *Gambierdiscus carolinianus* + *polynesiensis* | TTTTTTTTTTTTTTCCCUGUUUCACCUUUCCAGCUCCAG |
| Seq ID No. 33 | *Gambierdiscus carolinianus* + *carpenteri* | TTTTTTTTTTTTTCCUCUUUCGUCCAGAAUUGGGCAAG |
| Seq ID No. 34 | *Gambierdiscus carolinianus* + *carpenteri* | TTTTTTTTTTTTTCUGUGCUGCUCCAUGACUGGAUGCU |
| Seq ID No. 35 | *Gambierdiscus carolinianus* + *carpenteri* | TTTTTTTTTTTTTCCCUGUUUCACCUUUCCAGCUCCAG |
| Seq ID No. 36 | *Gambierdiscus toxicua* and *pacificus* | TTTTTTTTTTTTTGGCGGACCAGGCAUCCCCAGCAGAG |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 37 | Gambierdiscus toxicua and pacificus | TTTTTTTTTTTTTACCUGUCACAGCCACAGCAGGCCAC |
| Seq ID No. 38 | Gambierdiscus toxicua and pacificus | TTTTTTTTTTTTTGUCAAUCCCACUUGUGCCAGGACCU |
| Seq ID No. 39 | Ostreopsis ovata Clade | TTTTTTTTTTTTTGCAUGCAGCUUUGAUAGCACUGUGC |
| Seq ID No. 40 | Ostreopsis ovata Clade | TTTTTTTTTTTTTGGACAAAGCAGGCACACACACAUGA |
| Seq ID No. 41 | Ostreopsis ovata Clade | TTTTTTTTTTTTTGGACAAAGCUGGUGGGUACAUAAGG |
| Group F | Genus Levels | |
| Seq ID No. 42 | Pseudo-nitzschia | TTTTTTTTTTTTTAGTACAGCGCAATCACTCAAAGAGC |
| Seq ID No. 43 | Pseudo-nitzschia + Fragilariopsis | TTTTTTTTTTTTTCAGATTCCACCCAAACATGGCAGAC |
| Seq ID No. 44 | Pseudo-nitzschia + Fragilariopsis | TTTTTTTTTTTTTATTCCACCCAAACATGGCAGACCAG |
| Seq ID No. 45 | Pseudo-nitzschia no P. pungens | TTTTTTTTTTTTTATGCTGTGCTATTTGCAGGCAGGGG |
| Seq ID No. 46 | Pseudo-nitzschia + some Fragilariopsis | TTTTTTTTTTTTTGCAAAGGCCGACTGGACACACCAC |
| Seq ID No. 47 | P. fraudulenta, P. subfraudulenta, P calliantha + P. australis + P. delicatissima + P. galaxiae (clade1) + P. multiseries | TTTTTTTTTTTTTCTACCAGGCGGACGGGAGTTTCAC |
| Seq ID No. 48 | P. fraudulenta + P. subfraudulenta + P. multistriata + P. galaxiae (clade1) + P. australis + P. multiseries + P. delicatissima | TTTTTTTTTTTTTACGGGAGTTTCACCCTCTCAGCTGTC |
| Seq ID No. 49 | P. multistriata + P. calliantha + P. australis + P. mutliseries + P. fraudulenta + P. cf. delicatissima clade4 | TTTTTTTTTTTTTACAGCGCCCAAGCCACAAGTGG |
| Seq ID No. 50 | Karenia | TTTTTTTTTTTTTCAGTATCGCATCCAGATCAAAACCTG |
| Seq ID No. 51 | Alexandrium | TTTTTTTTTTTTTTACCACCCACTTTGCATTCCAATG |
| Seq ID No. 52 | Dinophysis in part | TTTTTTTTTTTTTACTTGCGTTGTGGCAGCAACCAAT |
| Seq ID No. 53 | Dinophysis | TTTTTTTTTTTTTTGCAGCCAGACAAACACTAAAGCT |
| Seq ID No. 54 | Pseudochattonella (genus) | TTTTTTTTTTTTTTAATGACCACCCTTCGAATCGCTTC |
| Seq ID No. 55 | Pseudochattonella (genus) | TTTTTTTTTTTTTCGTGAAAACGCCCGGCATTGTTATT |
| Seq ID No. 56 | Pseudochattonella (genus) | TTTTTTTTTTTTTACGACCCACGTTCACAGATTACCCA |
| Seq ID No. 57 | Dinophysis genus sensu stricto | TTTTTTTTTTTTTCACGATGTGATTTAACACAGATTACCC |
| Seq ID No. 58 | Dinophysis genus sensu stricto | TTTTTTTTTTTTTCGGAGTCGGATTGTTGGGCATGTAT |
| Seq ID No. 59 | all Dinophysis | TTTTTTTTTTTTTATCGCCAGTTGGTACCATGCAATTC |
| Seq ID No. 60 | Karlodinium genus | TTTTTTTTTTTTTGGAACGTGACTCTTAGAAAGCACAC |
| Seq ID No. 61 | Karenia genus | TTTTTTTTTTTTTTCGGTTGCTGGTGCAGATATCCCAG |
| Seq ID No. 62 | Azadinium Genus | TTTTTTTTTTTTTCAATCTCATCAAGAACACTGGTTCCAT |
| Seq ID No. 63 | Azadinium Genus | TTTTTTTTTTTTTAAGACAAGAAACACCACGCACATCT |
| Seq ID No. 64 | Azadinium Genus | TTTTTTTTTTTTTCCTTCCACAGAGTCGGGTATGG |
| Seq ID No. 65 | Azadinium Genus + Karenia. mikimoitoi | TTTTTTTTTTTTTAACCCTTCCACAGAGTCGGGTATG |
| Seq ID No. 66 | Prorocentrum | TTTTTTTTTTTTTCTCCATTGGCGATGCATCTCGAGAC |
| Seq ID No. 67 | Chattonella genus | TTTTTTTTTTTTTCUCCUUGCGAAGCCGACCGAUCACU |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 68 | *Chattonella* genus | TTTTTTTTTTTTTTTGCAGACUCCUUGCGAAGCCGACCG |
| Seq ID No. 69 | *Chattonella* genus | TTTTTTTTTTTTTTAAGCGCCUUCCCCAAGGAUGGCAAG |
| Group G | Species Level | |
| Seq ID No. 70 | *Alexandrium* NA, WE, TA, | TTTTTTTTTTTTTTGTATTCAAGGCCAAACACCTGCTTG |
| Seq ID No. 71 | *Alexandrium minutum* | TTTTTTTTTTTTTTCCTTTCCAGGCAAGGTTGCAAACTC |
| Seq ID No. 72 | *Alexandrium tamarense* (NA) | TTTTTTTTTTTTTCAAGTGCAACACTCCCACCAAGCAA |
| Seq ID No. 73 | *Alexandrium tamarense* (NA) | TTTTTTTTTTTTTAGTGCAACACTCCCACCAAGCAAAT |
| Seq ID No. 74 | *Alexandrium tamarense* (TA) | TTTTTTTTTTTTTGCAAGCACTACAATCTCACTGAGGA |
| Seq ID No. 75 | *Alexandrium ostenfeldii* | TTTTTTTTTTTTTCATTCCAATGCCCACAGGCAAATTA |
| Seq ID No. 76 | *Alexandrium ostenfeldii* | TTTTTTTTTTTTTGAATCACCAAGGTTCCAAGCAGAGC |
| Seq ID No. 77 | *Prymnesium* (=*Chrysochromulina*) *polylepis* | TTTTTTTTTTTTTTTATAGTTTCCCATAAGGTGCCGACG |
| Seq ID No. 78 | *Prymnesium parvum* | TTTTTTTTTTTTTTTCAG CCG ACG CCG AGC GCG |
| Seq ID No. 79 | *Prymnesium parvum* | TTTTTTTTTTTTTAAGAAGTGCTCGCCAACGAGGTGTT |
| Seq ID No. 80 | *Karenia mikimotoi* and some *Karenia brevis* | TTTTTTTTTTTTTAGCAGAAGATCGCAGGCAAGCACAC |
| Seq ID No. 81 | *Karenia brevis* | TTTTTTTTTTTTTAGCAGAAGATTGCAAGCAAGCACAC |
| Seq ID No. 82 | *Karenia brevis* | TTTTTTTTTTTTTACATGCTCCTGGCACTAGCAACCTT |
| Seq ID No. 83 | competitor *Karenia brevis* | TTTTTTTTTTTTTACATGCTCCTGGCACTAGCACCCTT |
| Seq ID No. 84 | *Karenia mikimotoi* | TTTTTTTTTTTTTCTTCATGCAGAGCAGAAGATCGCAG |
| Seq ID No. 85 | *Karlodinium veneficium* | TTTTTTTTTTTTTAATTCAAGCCCAGAGGGCCCAATTT |
| Seq ID No. 86 | *Karlodinium veneficium* | TTTTTTTTTTTTTGGAAATCAGTTTAGACATGAGTTCT |
| Seq ID No. 87 | *Karlodinium veneficium* | TTTTTTTTTTTTTTAGAGTTTTCCTCAAATCTGAACCG |
| Seq ID No. 88 | *Karlodinium veneficium* | TTTTTTTTTTTTTCAGAGGGCCCAATTTCCAAGCTGAG |
| Seq ID No. 89 | *Karlodinium veneficium* | TTTTTTTTTTTTTGCGACGAGTAACAGAAGCTACAAGC |
| Seq ID No. 90 | *Karlodinium veneficium* | TTTTTTTTTTTTTGAAAGACTACAATTCAAGCCCAGAG |
| Seq ID No. 91 | *Karenia brevis* | TTTTTTTTTTTTTCGTTCAGGATCTGAACACTGCGGCA |
| Seq ID No. 92 | *Karenia brevis* | TTTTTTTTTTTTTCAACGTTCAGGATCTGAACACTGCG |
| Seq ID No. 93 | *Karenia brevis* + *Karenia mikimotoi* | TTTTTTTTTTTTTGCAGTGCGACCAGACACACAGTGAG |
| Seq ID No. 94 | *Karenia brevis* + *Karenia mikimotoi* | TTTTTTTTTTTTTCGGAGCAGTGCGACCAGACACACAG |
| Seq ID No. 95 | *Prorocentrum planktonic* clade | TTTTTTTTTTTTTTGCAATCAGAACCCATCCTAGTCCT |
| Seq ID No. 96 | *Prorocentrum lima* | TTTTTTTTTTTTTTAGCTCTAGCATTTCCACGGGTATC |
| Seq ID No. 97 | *Prorocentrum lima* | TTTTTTTTTTTTTTACACCCCAATTGCCTCGTAGGCAG |
| Seq ID No. 98 | *Prorocentrum minimum* | TTTTTTTTTTTTTTCCGCAAATGAGTTCTGCCAAGGCT |
| Seq ID No. 99 | *Prorocentrum belizaneum* & *P. maculosum* | TTTTTTTTTTTTTAUUUAUCGCCAGCGGACGCCAUACG |
| Seq ID No. 100 | *Prorocentrum maculosum* | TTTTTTTTTTTTTUCCCCGUUCAUUCGCGCAUUACUG |
| Seq ID No. 101 | *Prororocentrum maculosum* 2 | TTTTTTTTTTTTTUGGUGCCCUUUAUCCAAGAGGCCCGC ACCUGC |
| Seq ID No. 102 | *Prorocentrum rathymum* and *P. mexicanum* | TTTTTTTTTTTTTGACAAGAAGCGCUGCAACCAGACAC |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 103 | *Prorocentrum rathymum* and *P. mexicanum* | TTTTTTTTTTTTTTTUGUGUCAGGGAAGCGCCCAGUCACC |
| Seq ID No. 104 | *Dinophysis acuminata* + *D. dens* + *D. sacculus* | TTTTTTTTTTTTTTATGCTCATCGCAACCACAGCAAAGC |
| Seq ID No. 105 | *Dinophysis acuta* + *D. fortii* | TTTTTTTTTTTTTTCATCGCAACCACAAGTCCTGCTTGA |
| Seq ID No. 106 | *Dinophysis acuminata* | TTTTTTTTTTTTTTTCACCAGACTTTCCACGGCAACGC |
| Seq ID No. 107 | *Dinophysis acuta* | TTTTTTTTTTTTTTCAGACTTTCCACGGCAACAATTAGG |
| Seq ID No. 108 | *Dinophysis norvegica* | TTTTTTTTTTTTTTTCCACGGCAACGTTCAGGAACTAAA |
| Seq ID No. 109 | *Phalacroma rotundatum* | TTTTTTTTTTTTTTGGCAACGCTCAGGAACTAAACACTG |
| Seq ID No. 110 | *Pseudo-nitzschia australis, P. seriata, P. multiseries* | TTTTTTTTTTTTTTGCUCUUCCAAAGGAUUCAACCAACC |
| Seq ID No. 111 | *P. australis* & *P. multistriata* | TTTTTTTTTTTTTTTGACAAATGACTCACTCCACCAGG |
| Seq ID No. 112 | *P. australis* & *P. seriata, P. delicatissima, P. calliantha, P. multiseries* | TTTTTTTTTTTTTTGACTGCGCTCTTCCAAAGGATTCAA |
| Seq ID No. 113 | *P. australis* & *P. seriata, P. calliantha* | TTTTTTTTTTTTTTGCCCAAACCACAAGTGGCCGGGGA |
| Seq ID No. 114 | *P. caciantha* + *P. australis* | TTTTTTTTTTTTTTTCGTCTGATAGAGTCAAACCCAGT |
| Seq ID No. 115 | *P. calliantha* | TTTTTTTTTTTTTTATTCGGCACCAAAAAGTGCAGATTT |
| Seq ID No. 116 | *P. calliantha* | TTTTTTTTTTTTTTGTCTACTCAAGTCAAACCCAGTGCT |
| Seq ID No. 117 | *P. mannii* + *P. australis* | TTTTTTTTTTTTTGGCGCTTAAACAGCGCAGATTTACA |
| Seq ID No. 118 | *P. mannii* | TTTTTTTTTTTTTTTAACGCCAAAGTCTTCAGACCACAA |
| Seq ID No. 119 | *P. mannii* + *P. australis* | TTTTTTTTTTTTTTCTTCAGACCACAATTCGGCGCTTAAA |
| Seq ID No. 120 | *P. mannii* | TTTTTTTTTTTTTTTATTTCGTCTGCTCGAGTCAAACCAG |
| Seq ID No. 121 | *P. delicatissima* + *P. austalis* | TTTTTTTTTTTTTTTCCAACCACTGTTACTTTCATTACG |
| Seq ID No. 122 | *P. cf. delicatissima* Clade4 + *P. galaxiae* (clade2) + *P. australis* | TTTTTTTTTTTTTTTGACAACGACTCACTCTACCAGGC |
| Seq ID No. 123 | *P. cf. delicatissima* Clade4 | TTTTTTTTTTTTTTGATTGTGCAAATATCCAACCACTGT |
| Seq ID No. 124 | *P. cf. delicatissima* Clade4 + *P. galaxiae* (clade2) + *P. australis* | TTTTTTTTTTTTTTTGACAACGACTCACTCTACCAGGC |
| Seq ID No. 125 | *P. dolorosa* + *P. micropora* | TTTTTTTTTTTTTTUAAUGUUAAAGUCUAUAGACCACAA |
| Seq ID No. 126 | *P. dolorosa* + *P. micropora* + *P. australis* | TTTTTTTTTTTTTTGACAAAACUCACUCUACCAGGCGG |
| Seq ID No. 127 | competitor *P. dolorosa* | TTTTTTTTTTTTTTGACAAGAACUCACUCUACCAGGCGG |
| Seq ID No. 128 | *P. arenysensis* + *P. multistriata* + *P. australis* + *P. galaxiae* (clade2) | TTTTTTTTTTTTTTTGACAACGACTCACTCCACCAGG |
| Seq ID No. 129 | *P. delicatissima* + *P calliantha* | TTTTTTTTTTTTTTCCACTGTTACTTTCATTACGCACCG |
| Seq ID No. 130 | *P. galaxiae*, all clades | TTTTTTTTTTTTTTCCACATCACAAGTGACAAGGGAAATA |
| Seq ID No. 131 | *P. galaxiae*, all clades | TTTTTTTTTTTTTTCCAAAGGAATCAACCAAAGCAAACC |
| Seq ID No. 132 | *P. galaxiae*, all clades | TTTTTTTTTTTTTTTCGTCTGCTTAAGTCAAAACCCAGT |
| Seq ID No. 133 | *Pseudo-nitzschia multiseries* + *P. australis* | TTTTTTTTTTTTTTTGATCCGTCGCCGCCAAAAGGCAT |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 134 | Pseudo-nitzschia multiseries + P. australis | TTTTTTTTTTTTTTTGACAAATGACTCACTCTGCCAGG |
| Seq ID No. 135 | P. multiseries + P. calliantha + P. australis | TTTTTTTTTTTTTTACCCAAACTCACGCAAGCCCACAG |
| Seq ID No. 136 | P. multiseries + P. calliantha | TTTTTTTTTTTTTTGCGCCCAAGCCACAAGTGGCTAGG |
| Seq ID No. 137 | P. multiseries + P. calliantha + P. australis | TTTTTTTTTTTTTTAAATGACTCACTCTGCCAGGCGGAC |
| Seq ID No. 138 | P. multistriata + P. australis | TTTTTTTTTTTTTTAACCCAAACTCACGAAAGCTCACAG |
| Seq ID No. 139 | P. pseudodelicatissima + P. cuspidata | TTTTTTTTTTTTTTTCCAAAGGGATCAACCAAGACAAA |
| Seq ID No. 140 | P. pseudodelicatissima + P. cuspidata | TTTTTTTTTTTTTTCCCGGCAGATAACGTCAAGGTCTAT |
| Seq ID No. 141 | Pseudo-nitzschia pungens + P. calliantha | TTTTTTTTTTTTTTATGGGCACCCTCAGTACGACAACT |
| Seq ID No. 142 | P. pungens + P. calliantha + P. multiseries + P. australis | TTTTTTTTTTTTTTCTCACGCAAGTCCACAGCGCCCA |
| Seq ID No. 143 | P. pungens + P. calliantha + P. australis | TTTTTTTTTTTTTTACTCACTTTACCAGGCGGACGGGA |
| Seq ID No. 144 | P. seriata, P. calliantha, P. multiseries, P. australis + P. multistriata | TTTTTTTTTTTTTTGACAAATGACTCACTCTACCAGGCG |
| Seq ID No. 145 | Chloromorum toxicum | TTTTTTTTTTTTTTACGAACAACACAATACACAATCCGCTAGG |
| Seq ID No. 146 | Chloromorum toxicum, Karenia mikimoitoi, Gymnodinium catenatum | TTTTTTTTTTTTTTGATGAGGATCGCAACACCAACAACCT |
| Seq ID No. 147 | Chloromorum toxicum | TTTTTTTTTTTTTTCTAGGAAAGGATCGGCGGCTCATAC |
| Seq ID No. 148 | Chloromorum toxicum | TTTTTTTTTTTTTTTCCACCGAAATGGTCAGGAGTTTATGCA |
| Seq ID No. 149 | Gymnodonium catenatum | TTTTTTTTTTTTTTGCATTTTAAAAGATTACCCAATCCTGTCG |
| Seq ID No. 150 | G. catenatum | TTTTTTTTTTTTTTCGTATAGTTAACGGCCTCCAATCTCTA |
| Seq ID No. 151 | G. catenatum | TTTTTTTTTTTTTTTACATCTACGCCCCTGCTGGCAG |
| Seq ID No. 152 | G. catenatum | TTTTTTTTTTTTTTCACCGCCCCGCTTTCGCTGGAATA |
| Seq ID No. 153 | Heterosigma akashiwo | TTTTTTTTTTTTTTTCGACCGAAGTCGATTCGCACAGTT |
| Seq ID No. 154 | H. akashiwo | TTTTTTTTTTTTTTCTTGAATGAACCATCGACCGAAGTC |
| Seq ID No. 155 | H. akashiwo | TTTTTTTTTTTTTTATGTTGAAACGCTCCAGGCCCCACG |
| Seq ID No. 156 | H. akashiwo | TTTTTTTTTTTTTTGGACCACGACTGAGCACGCACCTTT |
| Seq ID No. 157 | H. akashiwo | TTTTTTTTTTTTTTGGAGCAAAGGTCCTCCGTCCTAACC |
| Seq ID No. 158 | H. akashiwo | TTTTTTTTTTTTTTACCAGCATACCCGAGAGAGGAACGC |
| Seq ID No. 159 | H. akashiwo | TTTTTTTTTTTTTTGGACCCCAGGCAAGAACCGGATTGT |
| Seq ID No. 160 | H. akashiwo | TTTTTTTTTTTTTTACTCGTCGGAAACGGCTCGTACGC |
| Seq ID No. 161 | Pseudochattonella verruculosa | TTTTTTTTTTTTTTAAGCAACTCGACTCCATTAGCACGG |
| Seq ID No. 162 | Pseudochattonella farcimen | TTTTTTTTTTTTTTAAGCAACTCGACTCCACTAGGACGG |
| Seq ID No. 163 | Vulcanodinium rugosum | TTTTTTTTTTTTTTUUUACCCACCCGCGAACUCGCACAU |
| Seq ID No. 164 | Vulcanodinium rugosum | TTTTTTTTTTTTTTCAAUUCAGGGCCAAUGGCCCCAAUU |
| Seq ID No. 165 | Vulcanodinium rugosum | TTTTTTTTTTTTTTGGCAAGCGGGAUUGUCACCCUCGCU |
| Seq ID No. 166 | Fibrocapsa japonica | TTTTTTTTTTTTTTGGGUAACGAAACGCCACCCAGAUUU |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 167 | *Fibrocapsa japonica* | TTTTTTTTTTTTTCCGAACCACGACAUGCCACAGGGUU |
| Seq ID No. 168 | *Fibrocapsa japonica* | TTTTTTTTTTTTTUUGUCACCGUCCACGAUGCCCCGUU |
| Seq ID No. 169 | *Dino* New Genus | TTTTTTTTTTTTTGUACACACCUGAGUCCCUACAAGCACA |
| Seq ID No. 170 | *Dino* New Genus | TTTTTTTTTTTTTGAGCAACCCCGCGGAGAAGCGUCGU |
| Seq ID No. 171 | *Chattonella subsalsa* | TTTTTTTTTTTTTGGACGAGGAACCCUCAUCCAGAUUU |
| Seq ID No. 172 | *Chattonella subsalsa* | TTTTTTTTTTTTTGGGUUAUCACCGUCCAUGACACUGU |
| Seq ID No. 173 | *Chattonella subsalsa* | TTTTTTTTTTTTTCAGUCCAAGCCACGACAGAGAAUGU |
| Seq ID No. 174 | *Gambierdiscus* clade2 with *caribaeus, carpenteri, austalis* | TTTTTTTTTTTTTAUCCUCCGUCACCUGUCACUGCCAC |
| Seq ID No. 175 | *Gambierdiscus toxicua* and *pacificus, belizeanus* | TTTTTTTTTTTTTAUCCUCCGUCACCUGUCACAGCCAC |
| Seq ID No. 176 | *Alexandrium* spp. | TTTTTTTTTTTTTAUCCUCCGUCACCUGUCAUUGCCAC |
| Seq ID No. 177 | *Gambierdiscus polynesiensus* to use with clade probe | TTTTTTTTTTTTTAUCCUCCGUCACCUGUUACUGCCAC |
| Seq ID No. 178 | *Gambierdiscus polynesiensus* | TTTTTTTTTTTTTGGGCCAGGCAAUGCCUGCAUUGGUU |
| Seq ID No. 179 | *Gambierdiscus polynesiensus* | TTTTTTTTTTTTTACCAGCUGAUGCACCACAAGCCGUU |
| Seq ID No. 180 | *Gambierdiscus polynesiensus* | TTTTTTTTTTTTTAGGUUAGCCAGAUUGCCCAGCCCUU |
| Seq ID No. 181 | *Gambierdiscus* clade2 with *caribaeus, carpenteri, austalis, polynesiensis* | TTTTTTTTTTTTTGCAUUGAUCCAUCCCCAUCACGAC |
| Seq ID No. 182 | *Gambierdiscus belizeanus* | TTTTTTTTTTTTTGCCAUGCACAGCACCAUUGUGGGAU |
| Seq ID No. 183 | *Gambierdiscus belizeanus* | TTTTTTTTTTTTTGCCAUGCACAGCACCAUUGUGGGAU |
| Seq ID No. 184 | *Gambierdiscus belizeanus* | TTTTTTTTTTTTTGAAGAUGCUUCCAAGCAUUGCCUGC |
| Seq ID No. 185 | *Gambierdiscus austalis* | TTTTTTTTTTTTTCCACGACCCAGGUUGUGGCUGUUUU |
| Seq ID No. 186 | *Gambierdiscus austalis* | TTTTTTTTTTTTTCGGACCAGCAAUCUCCAGCAGAAAU |
| Seq ID No. 187 | *Gambierdiscus austalis* | TTTTTTTTTTTTTCAACAACCACAACUCACCACAGGUG |
| Seq ID No. 188 | *Gambierdiscus* new species clade | TTTTTTTTTTTTTAUUGCAACCAGGCAUCGCCUGCAUU |
| Seq ID No. 189 | *Gambierdiscus* new species clade | TTTTTTTTTTTTTGAAUGCUGCAACAGGGCCAAACUGU |
| Seq ID No. 190 | *Gambierdiscus* new species clade | TTTTTTTTTTTTTCCCCUCUGGAAAAGAAUGCUUGGGU |
| Seq ID No. 191 | *Gambierdiscus pacificus* | TTTTTTTTTTTTTACCAUCCCCUUUGGACACUGUCUUCACU |
| Seq ID No. 192 | *Gambierdiscus pacificus* | TTTTTTTTTTTTTGCCUUCGCCCUAGUUCAUCCUUGAC |
| Seq ID No. 193 | *Gambierdiscus pacificus* | TTTTTTTTTTTTTCCAUCACGGUGCAGAUUUCAAAGAU |
| Seq ID No. 194 | *Gambierdiscus carolinianus* | TTTTTTTTTTTTTGCUCCAGGCAUAGCCUGCGUUAGUU |
| Seq ID No. 195 | *Gambierdiscus carolinianus* | TTTTTTTTTTTTTGGACCAGCCAACCCCAGCAGAAAUU |
| Seq ID No. 196 | *Gambierdiscus carolinianus* | TTTTTTTTTTTTTGACCACAAUCCACAGCUGAACUGCU |
| Seq ID No. 197 | *Gambierdiscus yasumotoi + fuetzleri* | TTTTTTTTTTTTTCCCUCCAGAAAUAUGCUCAGGCUGU |
| Seq ID No. 198 | *Gambierdiscus yasumotoi + fuetzleri* | TTTTTTTTTTTTTCCAGCCAUUCCAGGCAAGAUGGAAU |
| Seq ID No. 199 | *Gambierdiscus yasumotoi + fuetzleri* | TTTTTTTTTTTTTGUGUUAUCCAAGAACUGAGUGCCACU |
| Seq ID No. 200 | *Gambierdiscus yasumotoi + fuetzleri* | TTTTTTTTTTTTTAAGGUGCCGAAGGAGUCAUCCGAGU |
| Seq ID No. 201 | *Gambierdiscus carpenteri* | TTTTTTTTTTTTTAAUAUGCUUAGGGUGCACCAGAUGCUC |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 202 | Gambierdiscus carpenteri | TTTTTTTTTTTTTAGUGGCACUCAGUUCUUGGAUAACAC |
| Seq ID No. 203 | Gambierdiscus carpenteri | TTTTTTTTTTTTTCAUGGGCGGACCGGCCAUCCUCUGC |
| Seq ID No. 204 | Gambierdiscus caribaeus | TTTTTTTTTTTTTGCGGACCAGGCAUCCUCUGCAGAAAUCCA |
| Seq ID No. 205 | Gambierdiscus caribaeus | TTTTTTTTTTTTTUUUAGGAAAUAUGCUCAGGCUGCACCAG |
| Seq ID No. 206 | Gambierdiscus caribaeus | TTTTTTTTTTTTTCUUCUGUAUGCACAGCACACACUUGC |
| Seq ID No. 207 | Gambierdiscus toxicus | TTTTTTTTTTTTTUCCAUGUGCAUCAACCAUCCACCU |
| Seq ID No. 208 | Gambierdiscus toxicus | TTTTTTTTTTTTTCCUAACGACGAAGUUUGCCAGCCAU |
| Seq ID No. 209 | Gambierdiscus toxicus | TTTTTTTTTTTTTCUUCUGCAUUCAAGGCAAAGCCUGC |
| Seq ID No. 210 | Ostreopsis siamensis | TTTTTTTTTTTTTAAAGCCAGUACGCACACUCAGUGGU |
| Seq ID No. 211 | Ostreopsis siamensis | TTTTTTTTTTTTTCAGUGCAUGAUCACAGUUGGUGCGU |
| Seq ID No. 212 | Ostreopsis siamensis | TTTTTTTTTTTTTCAGUGCACACAUGGAGCACACCAAU |
| Seq ID No. 213 | Ostreopsis lenticularis | TTTTTTTTTTTTTCAAGUUGGAUGCAGCUCCUCUGCUU |
| Seq ID No. 214 | Ostreopsis lenticularis | TTTTTTTTTTTTTGUGCUCAUUGGUAGCAGCAUGCCAU |
| Seq ID No. 215 | Ostreopsis lenticularis | TTTTTTTTTTTTTGACUCUCACAUUCCAUGCUCCUCUG |
| Seq ID No. 216 | Ostreopsis sp. cf. Ovata | TTTTTTTTTTTTTGGCAAUAGCCUGCCAAGAACGCUUU |
| Seq ID No. 217 | Ostreopsis sp. cf. Ovata | TTTTTTTTTTTTTCGGGUAGGUCUGGUCCUGGUAAUUU |
| Seq ID No. 218 | Ostreopsis sp. cf. Ovata | TTTTTTTTTTTTTGCAGUUUCCAGGUUGCCACACCAUU |
| Seq ID No. 219 | Ostreopsis sp. 24 | TTTTTTTTTTTTTAUUGGUGGGAGAUGCACCAGUGUGU |
| Seq ID No. 220 | Ostreopsis sp. 24 | TTTTTTTTTTTTTAACAUUGGUGGGAGAUGCACCAGUG |
| Seq ID No. 221 | Ostreopsis sp. 24 | TTTTTTTTTTTTTAGCAUGAGUCUGCCACACAGAAGUG |
| Seq ID No. 222 | Ostreopsis sp. Middle clade in Ost. Ovata | TTTTTTTTTTTTTGCAAGUGCAAGGACAAGCUUCACAG |
| Seq ID No. 223 | Ostreopsis sp. Middle clade in Ost. Ovata | TTTTTTTTTTTTTCUCCCAACCUGACGCAGUAUUCCAC |
| Seq ID No. 224 | Ostreopsis sp. Middle clade in Ost. Ovata | TTTTTTTTTTTTTCGGAUUCCCCUUUUGCGCUUCAGUU |
| Seq ID No. 225 | Ostreopsis sp. Middle clade in Ost. Ovata COMPTITOR | TTTTTTTTTTTTTCGGAUUCCCCUUUUGCGCUUCAGUU |
| Seq ID No. 226 | Ostreopsis sp. Middle bottom clade | TTTTTTTTTTTTTUAACGGUGUUUUCCACACAGAUGAA |
| Seq ID No. 227 | Ostreopsis sp. Middle bottom clade | TTTTTTTTTTTTTAACAACUGUUGUUGUGCAGGCCCGA |
| Seq ID No. 228 | Ostrepsis sp. Missing middle clade | TTTTTTTTTTTTTAAGUUGCCACAGCAAGCACCAGCAU |
| Seq ID No. 229 | Ostrepsis sp. Missing middle clade | TTTTTTTTTTTTTCCCGCUGAUCAACCCAAGCCCGUUC |
| Seq ID No. 230 | Ostrepsis sp. Missing middle clade | TTTTTTTTTTTTTCCCCGCUGAUCAACCCAAGCCCGUU |
| Seq ID No. 231 | ostreopsis sp. Subset of top & bottom clade, top only | TTTTTTTTTTTTTGCCACAGCAAACACUAGCAUCACAG |
| Seq ID No. 232 | Ostreopsis sp. Middle lower clade | TTTTTTTTTTTTTGCACUCUUUGCUAUGCAAGAGAGCC |
| Seq ID No. 233 | Ostreopsis sp. lower clade | TTTTTTTTTTTTTGCCCAACAACUGUUACUCUGCAGUC |
| Seq ID No. 234 | Coolia monotis | TTTTTTTTTTTTTCGCCACGGUAUGCCAAGACCAUACC |
| Seq ID No. 235 | Coolia monotis | TTTTTTTTTTTTTUCACCCGUCAACGCCACGGUAUGCC |

TABLE 1-continued

Barcodes for toxic algae listed in a hierarchical fashion and the hybridisation controls

| Seq ID No. | Targeted Species | DNA Barcode: probe sequence with poly T-spacer Probe Sequences (5'-3') |
|---|---|---|
| Seq ID No. 236 | *Coolia monotis* | TTTTTTTTTTTTTGGUCCAGCAUAAAGCUGGUGAUGGU |
| Seq ID No. 237 | *Coolia monotis* clade 3 sequences | TTTTTTTTTTTTTCAAAACAUACACAUGACACAUGGGAUU |
| Seq ID No. 238 | *Gonyaulaux spinfera* 2 spp | TTTTTTTTTTTTTCACUCACAGUAGGUUCAGGGCCUUU |
| Seq ID No. 239 | *Gonyaulaux spinfera* 2 spp | TTTTTTTTTTTTTACCAUAUCCCCCCAAAAGCAUGCAG |
| Seq ID No. 240 | *Gonyaulaux spinfera* 2 spp | TTTTTTTTTTTTTUGCAAAGGCACGCCAUCAGCAAACU |
| Seq ID No. 241 | *Gonyaulaux spinfera* 2 spp + *baltica* | TTTTTTTTTTTTTUCCCAAGAAGCACGACUCAGAGGUG |
| Seq ID No. 242 | *Gonyaulaux spinfera* 2 spp + *baltica* third spp | TTTTTTTTTTTTTUCCCAAGAAGCACGACUCAGGGGUG |
| Seq ID No. 243 | *Gonyaulaux spinifera* 3 spp | TTTTTTTTTTTTTAUUCCAAUCACAAGACACAGAUGCCCCA |
| Seq ID No. 244 | *Gonyaulaux spinifera* 3 spp | TTTTTTTTTTTTTAGGUACACACCCAAUGGGCAGACCA |
| Seq ID No. 245 | *Gonyaulaux spinifera* 3 spp | TTTTTTTTTTTTTGAACCUGGCAAUGCCAGGAAUGGUU |
| Seq ID No. 246 | *Gonyaulaux spinifera* 4 spp | TTTTTTTTTTTTTAGUUCUGGCAGGGCCAGCAUUGAUU |
| Seq ID No. 247 | *Lingulodinium polyhedrum* | TTTTTTTTTTTTTGGCAAACAGGACUGUCACCCUCAUU |
| Seq ID No. 248 | *Lingulodinium polyhedrum* | TTTTTTTTTTTTTGGACUGUCACCCUCAUUAGUGCUCU |
| Seq ID No. 249 | *Lingulodinium polyhedrum* | TTTTTTTTTTTTTCUGCACCCCCAUUGGCAACGCAUCU |
| Seq ID No. 250 | *Protoceratium reticulatum* | TTTTTTTTTTTTTCUCACCCUCGUUGAUGCUUUUUCCCAAAAG |
| Seq ID No. 251 | *Protoceratium reticulatum* | TTTTTTTTTTTTTAUACACCCGCUUCCUCUUCAGCAAU |
| Seq ID No. 252 | *Protoceratium reticulatum* | TTTTTTTTTTTTTCAUCUUCAAACUACAAUUCAAGGCCAGA |

EXAMPLES

Various aspects of the invention are described below with reference to the following non-limiting examples. The inventors contemplate incorporating any one or more specific feature of the examples into the claimed invention in its various aspects.

Introduction

The embodiments of the present disclosure encompass barcodes for toxic algae occurring universally in all marine and estuarine waters. The example below describes each step in the analysis of the microarray from its spotting to the inference of cell numbers from the microarray signal.

Materials and Methods

The present disclosure is a microarray slide for detecting different species of toxic algae comprising probes selected from the group of DNA barcodes from the barcodes listed in Table 1. Light grey-labelled cells SEQ ID NOs: 1 to 8 are the controls on the microarray. The taxonomic hierarchy levels are highlighted in darker grey. Probes were designed using the probe design function in the ARB programme (Ludwig et al. 2004), all with approximately the same GC content and melting temperature.

Basically the procedure for using the device is as follows: For monitoring purposes, a specific volume of water is taken and concentrated to perform an RNA extraction of the sample.

Preferably the extraction should take place in Tri-Reagent (Sigma) to optimise the quanitity and quality of the RNA.

The RNA is fragmented into smaller pieces for ease of access of the barcode to the target site and labelling with a fluorescent label (labelling done with Platinum Bright Labelling Kit, KREAtech). Following purification of the labelled RNA from unlabelled product, it is hybridised at 60° C. to the microarray, then washed and scanned with a laser to detect RNA with labels bound to the probes, then analysed with the GPR analyser program.

Preferably the hybridisation includes a solution that boosts the melting temperature of the probes. Preferably the washing is done at least once above 30 degrees C., e.g. up to 50 degrees C.

Preferably the washing includes 3 washes using the following:

| Washing Buffer 1 | 2x SSC/10 mM EDTA/0.05% SDS |
| Washing Buffer 2 | 0.5x SSC/10 mM EDTA |
| Washing Buffer 3 | 0.2x SSC/10 mM EDTA |

The hybridisation may be provided by a solution as defined below:
a) at least one buffer composed of one protein, a salt, a buffer, a soap, and water,
b) positive control artificial DNA to bond to a probe on a microarray slide,
c) a component to prevent binding to a probe spacer, and
d) a blocking agent to prevent unwanted reactions Preferably the hybridisation buffer for use with the invention contains at least one protein, salt, buffer, soap, and water. The buffer used in the examples was made up of the following:

| Components | 50 mL | Final Conc |
|---|---|---|
| BSA | 5.0 mL (20 µg/µL stock) | 2.0 mg/mL |
| Herring sperm DNA | 2 mL (10 µg/µL) | 0.4 µg/µL |
| NaCl (5M) | 40 mL | 4M |
| Tris-Cl, pH8.0 (1M) | 2 mL | 20 mM |
| Triton 100 (10%) | 100 µL (10%) | 0.02% |
| MilliQ | to 50 mL | |

Preferably the positive control artificial DNA is TBP positive control or TATA Box gene PCR product for hybridisation control.

Preferably the component to prevent binding is Poly-A (1 µM) to block poly T spacer on probes Preferably the blocking agent is KREAblock as sold by KREAtech.

Results

An example of the invention will now be described and the results from several hybridisations and their analyses will be illustrated.

A seawater sample was passed through a filter to concentrate the assemblage of cells in a known quantity of water, e.g., one liter. The RNA was extracted from the cells by known techniques, and the RNA was fragmented (Lewis et al 2012). The RNA was extracted using RNA Extraction solution having a TriReagent (Sigma), a Phase Lock Gel Heavy 2 mL (SPrime), a lyophilised *Dunaliella tertiolecta* cells for extraction control, BCP (1-bromo-3-chloropropane), Isopropanol, and Ammonium acetate (7.5M). The RNA was fragmented using a RNA fragmentation stop buffer (0.5M EDTA pH 8) (FIG. 3). The fragmented RNA was labelled with a fluorescent label, using KREATECH Platinum Bright 647 Nucleic Acid Labelling Kit.

RNA fragmentation buffer (100 mM ZnCl2 in 100 mM Tris-Hcl pH 7)

The fragmented fluorescent-labelled RNA was mixed with a hybridisation solution made up from:
1. 4× Hybridization Buffer*:

| Components | 50 mL | Final Conc |
|---|---|---|
| BSA | 5.0 mL (20 µg/µL stock) | 2.0 mg/mL |
| Herring sperm DNA | 2 mL (10 µg/µL) | 0.4 µg/µL |
| NaCl (5M) | 40 mL | 4 M |
| Tris-Cl, pH8.0 (1M) | 2 mL | 20 mM |
| Triton 100 (10%) | 100 µL (10%) | 0.02% |
| MilliQ | To 50 mL | |

2. TBP positive control or TATA Box gene PCR product for hybridisation control
3. Poly-A (1 µM) to block poly T spacer on probes
4. KREAblock (KREAtech)

The fragmented fluorescent labelled RNA was mixed with a hybridisation solution and applied to the slide and hybridised at 60° C. The slide was then washed three times above 30° C., e.g. up to 70° C., more typically at 50° C. The slide was then scanned with a laser to detect RNA with labels bound to the probes to identify the presence of toxic algae (FIG. 2). As shown in FIG. 1, the probes were arranged in groups of four identical probes on the microarray. The intensity of different colours representing different species of toxic algae can easily be interpreted to give a concentration value for a particular toxic alga in a water sample as shown in FIGS. 4 & 5.

DISCUSSION

The DNA codes defined above are a unique sequence specific to one or a group of species of toxic algae as shown. The probes each with their unique DNA code and length of spacer attached to a slide allow the all the different of types of toxic algae in all marine and estuarine waters as specified to be detected in one operation. The solution used for hybridisation boosts the melting temperature of the probes allowing good binding to occur between parts of RNA and the probes.

Microarrays are state of the art technology in molecular biology for the processing of bulk samples for detection of target RNA/DNA sequences and this microarray will develop the first commercially universal microarray (phylochip), capable of rapidly detecting the presence of specific harmful algal species, which reduces the need for the mouse bioassay. This phylochip for toxic species is expected to reduce the health risk for humans who eat farm-raised fish and shellfish and even those who collect shellfish personally because warning notices not to collect can be posted earlier.

The prime social objectives of such a microarray are:
To provide a reduction in the health risk caused by presence of algal biotoxins both in swimming waters and in seafood by predicting dangerous concentrations of algal cells thanks to the rapid in-situ detection and high sensitivity of the microarray before cell numbers reach a dangerous level, To promote the health, fitness and well-being of all members of the community by predicting levels of toxins irrespective of the cell numbers present, To contribute and support the economic well-being of small coastal fishing communities, which are under threat due to interruptions in fishing activity, by providing them with a cost-effective means of personal monitoring by individual fish farmers for levels of toxins and species, To prevent potential economic losses in aquaculture and tourist industry, and To reduce the need for the mouse bioassay, which is ethically undesirable, by improving the current European monitoring systems.

The purpose of this microarray is to support the common fisheries policy and to aid national monitoring agencies by providing new rapid tools for the identification of toxic algae and their toxins so that they can comply with EC directive 2004/41/EC reducing the need for the mouse bioassay, which was phased out by the EU in 2012.

The invention may take a form different to that specifically described.

Further modifications will be apparent to those skilled in the art without departing from the scope and spirit of the present invention.

REFERENCES

Anderson D M, Kaoru Y, A. W. White A M (2000). Estimated Annual Economic Impacts from Harmful Algal Blooms (HABs) in the United States. Woods Hole Oceanographic Institution Technical Report WHOI-2000-11, 97 pp.

Browne R, Deegan, B, O'Carrol T, Norman M, O'Cinneide M (2007) Status of Irish Aquaculture 2006. Marine Institute, Dublin.

Dittami, S. M., Edvardsen, B. (2012). GPR-Analyzer, a simple tool for quantitative analysis of hierarchical multispecies microarrays. Environ. Sci. Pollut. Res. doi, 10.1007/s11356-012-1051-5.

FAO, 2004. Marine Biotoxins. FAO Food and Nutrition Paper 80, Food and Agriculture Organization Of The United Nations, Rome.

Lewis, J., Medlin, L. K., Raise, R. (2012). MIDTAL (Microarrays for the Detection of Toxic Algae), A Protocol for a Successful Microarray Hybridisation and Analysis. Koeltz Publishing.

Ludwig W. S O, Westram R., Richter L, Meler H., Yadhukumar, Buchner A., Lal T., Steppi S., Jobb G., Förster W., Brettske I., Gerber S., Ginhart A. W., Gross O., Grumaan S., Hermann S., Joest R., König A., Liss T., Lüßmann R., May M., Nonhoff B., Reichel B., Streblow R., Stamatakis A., Stuckmsan N., Villbig A., Leake M., Ludwig T., Bode A., and Schleifer K.-H. (2004). ARB, a software environment for sequence data. Nucleic Acids Research 32:1363-71.

Medlin L K, Koolstra, WHCF (2010). Methods to estimate the diversity in the marine photosynthetic protist community with illustrations from case studies: a review. Special Issue of Diversity "Biological Diversity Assessed by Molecular Methods", 2: 973-1014.

Touzet N, Franco J M, R R. Raise R (2008) PSP toxin analysis and discrimination of the naturally co-occurring *Alexandrium tamarense* and *A. minutum* in Cork Harbour, Ireland. Aq Micro Ecol, 51: 285-299.

Various Further Aspects of the Present Invention are Described in the Passages which Follow:

The present invention relates to a microarray slide for detecting toxic algae, barcodes of DNA, hybridisation solution and method of detecting toxic algae.

It is often desirable to detect toxic algae in seawater to prevent the consumption of fish or shellfish contaminated by the toxic algae. Hitherto this has been done by examining natural seawater samples, detecting and identifying the toxic algal cells under a microscope, enumerating the different species and then extrapolating the results to estimate the concentration (as cells·$L^{-1}$) of different toxic species in a water sample. This is an extremely time consuming process and requires a skilled operator. Often the results are available up to 5 days after taking the sample making mitigation strategies almost impossible.

The invention seeks, inter alia, to provide a solution to this problem.

According to one aspect of the present invention there is provided a microarray slide for detecting different species of toxic algae comprising at least one probe each in equal number selected from the group of DNA barcodes disclosed in the sequence listing filed herewith.

According to a further aspect of the present invention there is provided one or more DNA barcodes selected from the group of DNA barcodes disclosed in the sequence listing filed herewith.

According to a further aspect of the present invention there is provided a method of identifying the presence of different species of toxic algae comprising:
a) collecting algae cells from a sample of water,
b) extracting the RNA from at least some of the cells,
c) fragmenting the RNA,
d) Labelling the RNA with a fluorescent label,
e) Hybridising RNA fragments to be detected to probes on a slide
f) Washing the slide, and
e) Scanning the slide with a laser to detect RNA with labels bound to the probes.

Preferably the hybridisation includes a solution that boosts the melting temperature of the probes.

Preferably the washing is done at least once above 30 degrees C., e.g. up to 50 degrees C.

Preferably the washing includes 3 washes using the following:

| | |
|---|---|
| Washing Buffer 1 | 2x SSC/10 mM EDTA/0.05% SDS |
| Washing Buffer 2 | 0.5x SSC/10 mM EDTA |
| Washing Buffer 3 | 0.2x SSC/10 mM EDTA |

The hybridisation may be provided by a solution as defined below.

According to a further aspect of the present invention there is provided a hybridisation solution comprising:
a) at least one protein, a salt, a buffer, a soap, and water,
b) Positive control artificial DNA to bond to a probe on a microarray slide
c) A component to prevent binding to a probe spacer
d) a blocking agent to prevent unwanted reactions Preferably the at least one protein, salt, buffer, soap, and water is made up of the following:

| Components | 50 mL | Final Conc |
|---|---|---|
| BSA | 5.0 mL (20 µg/µL stock) | 2.0 mg/mL |
| Herring sperm DNA | 2 mL (10 µg/µL) | 0.4 µg/µL |
| NaCl (5M) | 40 mL | 4M |
| Tris-Cl, pH8.0 (1M) | 2 mL | 20 mM |
| Triton 100 (10%) | 100 µL (10%) | 0.02% |
| MilliQ | to 50 mL | |

Preferably the positive control artificial DNA is TBP positive control TATA Box gene PCR product for hybridisation control.

Preferably the component to prevent binding is Poly-dA (1 µM) to block poly T spacer on probes Preferably the blocking agent is KREAblock as sold by KREAtech.

An example of the invention will now be described.

A sea water sample was passed through a filter to extract a mass algae cells.

The RNA was extracted from the cells by known techniques, and the RNA was fragmented. The RNA was extracted using RNA Extraction solution having a TriReagent (Sigma), a Phase Lock Gel Heavy 2 mL (SPrime), a Lypholised *Dunaliella tertiolecta* cells for extraction control, BCP (I-bromo-3-chloropropane), Isopropanol, and Ammonium acetate (7.5M). RNA fragmentation buffer (100 mM ZnCl2 in 100 mM Tris-Hcl pH 7). The RNA was fragmented using a RNA fragmentation stop buffer (0.5M EDTA pH 8).

The fragmented RNA was labeled with a fluorescent label, using KREATECH Platinum Bright 647 Nucleic Acid Labelling Kit.

A microarray slide for detecting different species of toxic algae comprising different probes each in equal number selected from the group or DNA codes disclosed in the sequence listing filed herewith.

The probes were arranged in groups of four identical probes.

The fragmented fluorescent labelled RNA was mixed with a hybridisation solution made up from:
1. 4× Hybridization Buffer*:

| Components | 50 mL | Final Conc |
|---|---|---|
| BSA | 5.0 mL (20 µg/µL stock) | 2.0 mg/mL |
| Herring sperm DNA | 2 mL (10 µg/µL) | 0.4 µg/µL |
| NaCl (5M) | 40 mL | 4M |
| Tris-Cl, pH8.0 (1M) | 2 mL | 20 mM |

-continued

| Components | 50 mL | Final Conc |
|---|---|---|
| Triton 100 (10%) | 100 µL (10%) | 0.02% |
| MilliQ | To 50 mL | |

2. TBP positive control TATA Box gene PCR product for hybridisation control
3. Poly-dA (1 µM) to block poly T spacer on probes
4. KREAblock (KREAtech)

The fragmented fluorescent labelled RNA was mixed with a hybridisation solution and applied to the slide and hybridised at 60 degrees C.

The slide was then washed three times above 30 degrees C., e.g. up to 70 degrees C., more typically at 50 degrees C.

The slide was then scanned with a laser to detect RNA with labels bound to the probes to identify the presence of toxic algae. The intensity of different colours representing different species of toxic algae can easily be interpreted to give a concentration value for a particular toxic alga in a water sample.

The DNA codes defined above are a unique sequence specific to one or a group of species of toxic algae as shown. The probes each with their unique DNA code and length of spacer attached to a slide allow the all the different of types of toxic algae as specified to be detected in one operation. The solution used for hybridisation boosts the melting temperature of the probes allowing good bonding to occur between parts of RNA and the probes.

may take a form different to that specifically described.

The invention claimed is:

1. An array system comprising a microarray slide configured to detect simultaneously a plurality of organisms in a sample,
   wherein the microarray slide comprises nucleic acid probes having fragments of 18S or 28S RNA sequence unique to each organism or taxonomical group thereof,
   wherein each of the nucleic acid probes has a poly-T tail or an alternative linker or a spacer element,
   wherein some of the nucleic acid probes are specific for detection of the species of each organism to be detected and other nucleic acid probes are specific for detection of at least one higher-level taxon to which each of the organisms to be detected belongs, said microarray slide comprising:
   a. at least one probe selected from the group consisting of positive and negative controls: wherein the probes in group a) comprise at least one probe having a sequence selected from SEQ ID NO: 1 to SEQ ID NO: 4, SEQ ID NO:7 and SEQ ID NO: 8, and
   b. at least one probe capable of selectively detecting at least one of eukaryotic organisms; wherein the probes in group b) comprise at least all of the probes having sequences respectively given in SEQ ID NO:9 to SEQ ID NO: 10; and
   c. at least one probe capable of selectively detecting the taxonomical phylum of the organism: wherein the probes in group c) comprise at least all of the probes having sequences respectively given in SEQ ID NO: 11 to SEQ ID NO: 13; and
   d. at least one probe capable of selectively detecting the taxonomical class of the organism; wherein the probes in group d) comprise at least all of the probes having sequences respectively given in SEQ ID NO: 14 to SEQ ID NO: 16; and
   e. at least one probe capable of selectively detecting a taxonomical clade of the organism at a taxonomical level intermediate between class and genus; the probes in group e) comprise at least all of the probes having sequences respectively given in SEQ ID NO: 17 to SEQ ID NO: 41; and f. at least one probe capable of selectively detecting the taxonomical genus of the organism: wherein the probes in group f) comprise at least all of the probes having sequences respectively given in SEQ ID NO: 42 to SEQ ID NO: 69; and g. at least one probe capable of selectively detecting the taxonomical species of the organism; and h. at least one probe capable of selectively detecting the taxonomical strain of the organism where both toxic and non-toxic strains of the same species exist, wherein the probes in group g) and/or h) comprise at least all of the probes having sequences respectively given in SEQ ID NO: 70 to SEQ ID NO: 252.

2. An array system comprising a microarray slide configured to detect simultaneously a plurality of organisms in a sample, wherein the microarray slide comprises nucleic acid probes having fragments of 18S or 28S RNA sequence unique to each organism or taxonomical group thereof, wherein each of the nucleic acid probes has a poly-T tail or an alternative linker or a spacer element, wherein some of the nucleic acid probes are specific for detection of the species of each organism to be detected and other nucleic acid probes are specific for detection of at least one higher-level taxon to which each of the organisms to be detected belongs, said microarray slide comprising:

a. at least one probe selected from the group consisting of positive and negative controls, wherein the probes in group a) comprise at least one probe having a sequence selected from SEQ ID NO: 1 to SEQ ID NO: 4, SEQ ID NO:7 and SEQ ID NO: 8; and b. at least one probe capable of selectively detecting at least one of eukaryotic organisms: wherein the probes in group b) comprise at least one of the probes having sequences respectively given in SEQ ID NO:9 to SEQ ID NO: 10; and c. at least one probe capable of selectively detecting the taxonomical phylum of the organism: wherein the probes in group c) comprise at least one of the probes having sequences respectively given in SEQ ID NO: 11 to SEQ ID NO: 13; and d. at least one probe capable of selectively detecting the taxonomical class of the organism: wherein the probes in group d) comprise at least one of the probes having sequences respectively given in SEQ ID NO: 14 to SEQ ID NO: 16; and e. at least one probe capable of selectively detecting a taxonomical clade of the organism at a taxonomical level intermediate between class and genus: the probes in group e) comprise at least one of the probes having sequences respectively given in SEQ ID NO: 17 to SEQ ID NO: 41; and f. at least one probe capable of selectively detecting the taxonomical genus of the organism; wherein the probes in group f) comprise at least one of the probes having sequences respectively given in SEQ ID NO: 42 to SEQ ID NO: 69; and g. at least one probe capable of selectively detecting the taxonomical species of the organism; and h. at least one probe capable of selectively detecting the taxonomical strain of the organism where both toxic and non-toxic strains of the same species exist, wherein the probes in group g) and/or h) comprise at least one of the probes having sequences respectively given in SEQ ID NO: 70 to SEQ ID NO: 252.

3. A method of fabricating the array system of claim 2, the method comprising a step of immobilizing by chemical bonding the nucleic acid probes of claim 2 onto a microarray slide.

4. A method of fabricating the array system of claim 1, the method comprising a step of immobilizing by chemical bonding the nucleic acid probes of claim 1 onto a microarray slide.

* * * * *